US009545414B2

(12) United States Patent
Dahl et al.

(10) Patent No.: US 9,545,414 B2
(45) Date of Patent: *Jan. 17, 2017

(54) UNITARY PHARMACEUTICAL DOSAGE FORM

(71) Applicant: BRISTOL-MYERS SQUIBB & GILEAD SCIENCES, LLC, Foster City, CA (US)

(72) Inventors: Terrence C. Dahl, Sunnyvale, CA (US); Munir A. Hussain, Belle Mead, NJ (US); Robert A. Lipper, Pennington, NJ (US); Robert L. Jerzewski, Belle Mead, NJ (US); Mark M. Menning, San Francisco, CA (US); Reza Oliyai, Burlingame, CA (US); Taiyin Yang, Monte Sereno, CA (US)

(73) Assignee: BRISTOL-MYERS SQUIBB & GILEAD SCIENCES, LLC, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/640,825

(22) Filed: Mar. 6, 2015

(65) Prior Publication Data
US 2015/0174147 A1 Jun. 25, 2015

Related U.S. Application Data

(60) Continuation of application No. 14/050,714, filed on Oct. 10, 2013, now Pat. No. 9,018,192, which is a division of application No. 11/453,122, filed on Jun. 13, 2006, now Pat. No. 8,598,185.

(60) Provisional application No. 60/771,279, filed on Feb. 7, 2006, provisional application No. 60/690,010, filed on Jun. 13, 2005.

(51) Int. Cl.
| | | |
|---|---|---|
| *A61K 31/683* | (2006.01) | |
| *A61K 31/536* | (2006.01) | |
| *A61K 31/513* | (2006.01) | |
| *A61K 9/24* | (2006.01) | |
| *A61K 9/20* | (2006.01) | |
| *A61K 31/522* | (2006.01) | |
| *A61K 31/535* | (2006.01) | |
| *A61K 31/551* | (2006.01) | |
| *A61K 31/675* | (2006.01) | |

(52) U.S. Cl.
CPC ............ *A61K 31/683* (2013.01); *A61K 9/209* (2013.01); *A61K 9/2054* (2013.01); *A61K 9/2077* (2013.01); *A61K 31/513* (2013.01); *A61K 31/522* (2013.01); *A61K 31/535* (2013.01); *A61K 31/536* (2013.01); *A61K 31/551* (2013.01); *A61K 31/675* (2013.01)

(58) Field of Classification Search
None
See application file for complete search history.

(56) References Cited

U.S. PATENT DOCUMENTS

| | | |
|---|---|---|
| 3,524,846 A | 8/1970 | Moffatt et al. |
| 3,622,677 A | 11/1971 | Short et al. |
| 3,682,930 A | 8/1972 | Bourquin et al. |
| 3,994,974 A | 11/1976 | Murakami et al. |
| 4,003,878 A | 1/1977 | Skaar et al. |
| 4,258,062 A | 3/1981 | Jonas et al. |
| 4,355,032 A | 10/1982 | Verheyden et al. |
| 4,384,005 A | 5/1983 | McSweeney |
| 4,430,343 A | 2/1984 | Iemura et al. |
| 4,476,248 A | 10/1984 | Gordon et al. |
| 4,724,233 A | 2/1988 | De Clercq et al. |
| 4,808,716 A | 2/1989 | Holy et al. |
| 4,816,570 A | 3/1989 | Farquhar |
| 4,879,288 A | 11/1989 | Warawa et al. |
| 4,935,507 A | 6/1990 | Takaya et al. |
| 4,957,924 A | 9/1990 | Beauchamp |
| 4,968,788 A | 11/1990 | Farquhar |
| 5,047,407 A | 9/1991 | Belleau et al. |
| 5,075,445 A | 12/1991 | Jarvest et al. |
| 5,142,051 A | 8/1992 | Holy et al. |
| 5,151,426 A | 9/1992 | Belleau et al. |
| 5,155,268 A | 10/1992 | Hester |
| 5,177,064 A | 1/1993 | Bodor |
| 5,179,104 A | 1/1993 | Chu et al. |
| 5,204,466 A | 4/1993 | Liotta et al. |
| 5,208,221 A | 5/1993 | Kim et al. |
| 5,210,085 A | 5/1993 | Liotta et al. |
| 5,386,030 A | 1/1995 | Kim et al. |
| 5,432,172 A | 7/1995 | Kashman et al. |
| 5,453,503 A | 9/1995 | Aikins et al. |
| 5,466,806 A | 11/1995 | Belleau et al. |
| 5,476,938 A | 12/1995 | Vemishetti et al. |
| 5,486,520 A | 1/1996 | Belleau et al. |
| 5,506,347 A | 4/1996 | Erion et al. |
| 5,512,596 A | 4/1996 | Kim et al. |
| 5,514,557 A | 5/1996 | Moghaddam |
| 5,514,798 A | 5/1996 | Bischofberger et al. |
| 5,519,021 A | 5/1996 | Young et al. |
| 5,538,975 A | 7/1996 | Dionne |
| 5,587,480 A | 12/1996 | Belleau et al. |
| 5,618,820 A | 4/1997 | Dionne |

(Continued)

FOREIGN PATENT DOCUMENTS

| | | |
|---|---|---|
| EP | 0 182 024 A2 | 5/1986 |
| EP | 0 206 459 A2 | 12/1986 |

(Continued)

OTHER PUBLICATIONS

"Anti-HIV Drug Updates—Three Drugs on the Near Horizon," Project Inform Perspective 35:4-7 (2003).

(Continued)

*Primary Examiner* — Dennis Heyer
(74) *Attorney, Agent, or Firm* — Cooley LLP

(57) ABSTRACT

In accordance with this invention a novel pharmaceutical product containing efavirenz, emtricitabine and tenofovir DF are provided as a multicomponent unitary oral dosage form, component 1 comprising tenofovir DF (and, optionally, emtricitabine) and component 2 comprising efavirenz, wherein components 1 and 2 are in a stabilizing configuration. In preferred embodiments component 1 is made by dry granulation.

19 Claims, No Drawings

(56) References Cited

U.S. PATENT DOCUMENTS

| | | |
|---|---|---|
| 5,618,964 A | 4/1997 | Cheng et al. |
| 5,627,186 A | 5/1997 | Cameron et al. |
| 5,663,159 A | 9/1997 | Starrett, Jr. et al. |
| 5,696,254 A | 12/1997 | Mansour et al. |
| 5,733,788 A | 3/1998 | Bischofberger |
| 5,744,596 A | 4/1998 | Mansour et al. |
| 5,756,706 A | 5/1998 | Mansour et al. |
| 5,763,606 A | 6/1998 | Mansour et al. |
| 5,792,756 A | 8/1998 | Starrett, Jr. et al. |
| 5,798,340 A | 8/1998 | Bischofberger et al. |
| 5,814,639 A | 9/1998 | Liotta et al. |
| 5,859,021 A | 1/1999 | Cameron et al. |
| 5,905,082 A | 5/1999 | Roberts et al. |
| 5,914,331 A | 6/1999 | Liotta et al. |
| 5,922,695 A | 7/1999 | Arimilli et al. |
| 5,935,946 A | 8/1999 | Munger, Jr. et al. |
| 5,977,089 A | 11/1999 | Arimilli et al. |
| 6,043,230 A | 3/2000 | Arimilli et al. |
| 6,057,305 A | 5/2000 | Holy et al. |
| 6,069,249 A | 5/2000 | Arimilli et al. |
| 6,069,252 A | 5/2000 | Liotta et al. |
| 6,113,920 A | 9/2000 | Maye et al. |
| 6,114,343 A | 9/2000 | Liotta et al. |
| 6,121,315 A | 9/2000 | Nair et al. |
| 6,180,639 B1 | 1/2001 | Coates et al. |
| 6,194,391 B1 | 2/2001 | Schinazi et al. |
| 6,238,695 B1 | 5/2001 | Makooi-Morehead et al. |
| 6,312,662 B1 | 11/2001 | Erion et al. |
| 6,417,191 B1 | 7/2002 | Barry et al. |
| 6,639,071 B2 | 10/2003 | Thompson et al. |
| RE38,333 E | 11/2003 | Arimilli et al. |
| 6,642,245 B1 | 11/2003 | Liotta et al. |
| 6,703,396 B1 | 3/2004 | Liotta et al. |
| 6,812,233 B1 | 11/2004 | Liotta |
| 6,939,964 B2 | 9/2005 | Thompson et al. |
| 7,094,413 B2 | 8/2006 | Buelow et al. |
| 7,795,217 B2 | 9/2010 | Adra |
| 7,851,165 B2 | 12/2010 | Fuhrmann et al. |
| 8,067,473 B2 | 11/2011 | Alchanati et al. |
| 8,592,397 B2 | 11/2013 | Dahl et al. |
| 8,598,185 B2 * | 12/2013 | Dahl ................ A61K 9/2054 514/221 |
| 8,716,264 B2 | 5/2014 | Dahl et al. |
| 8,871,271 B2 | 10/2014 | Dahl et al. |
| 9,018,192 B2 * | 4/2015 | Dahl ................ A61K 9/2054 424/464 |
| 2001/0012518 A1 | 8/2001 | Makooi-Morehead et al. |
| 2001/0014352 A1 * | 8/2001 | Batra ................ A61K 9/2018 424/464 |
| 2003/0203969 A1 | 10/2003 | Bevec et al. |
| 2004/0180089 A1 * | 9/2004 | Plachetka ........ A61K 9/2009 424/472 |
| 2004/0224917 A1 | 11/2004 | Dahl et al. |
| 2004/0253218 A1 | 12/2004 | Eisenbach-Schwartz et al. |
| 2005/0197320 A1 | 9/2005 | Chen et al. |
| 2006/0128692 A1 | 6/2006 | Chen et al. |
| 2006/0246130 A1 | 11/2006 | Dahl et al. |
| 2007/0036861 A1 | 2/2007 | Oury et al. |
| 2007/0077295 A1 | 4/2007 | Dahl et al. |
| 2007/0099902 A1 | 5/2007 | Dahl et al. |
| 2009/0036408 A1 | 2/2009 | Dahl et al. |
| 2009/0143314 A1 | 6/2009 | Dahl et al. |
| 2014/0037732 A1 | 2/2014 | Dahl et al. |
| 2014/0213556 A1 | 7/2014 | Dahl et al. |
| 2014/0370102 A1 | 12/2014 | Dahl et al. |
| 2015/0111855 A1 | 4/2015 | Dahl et al. |
| 2015/0111856 A1 | 4/2015 | Dahl et al. |

FOREIGN PATENT DOCUMENTS

| | | | |
|---|---|---|---|
| EP | 0 269 947 A1 | 6/1988 | |
| EP | 0 369 409 A1 | 5/1990 | |
| EP | 0 382 526 A2 | 8/1990 | |
| EP | 0 481 214 A1 | 4/1992 | |
| EP | 0 482 657 A2 | 4/1992 | |
| EP | 0 595 635 | 5/1994 | |
| EP | 0 632 048 A1 | 1/1995 | |
| EP | 0 647 649 A1 | 4/1995 | |
| EP | 0 694 547 A2 | 1/1996 | |
| EP | 1 256 585 A1 | 11/2002 | |
| EP | 1 332 757 A1 | 8/2003 | |
| GB | 942 152 A | 11/1963 | |
| GB | 1 523 865 A | 9/1978 | |
| GB | 2 111 043 A | 6/1983 | |
| WO | WO 88/05438 | 7/1988 | |
| WO | WO 91/19721 A1 | 12/1991 | |
| WO | WO 92/01698 | 2/1992 | |
| WO | WO 92/09611 A1 | 6/1992 | |
| WO | WO 92/13869 | 8/1992 | |
| WO | WO 92/14743 | 9/1992 | |
| WO | WO 93/03027 | 2/1993 | |
| WO | WO 94/03466 | 2/1994 | |
| WO | WO 94/03467 | 2/1994 | |
| WO | WO 95/07919 | 3/1995 | |
| WO | WO 95/07920 | 3/1995 | |
| WO | WO 95/32957 | 12/1995 | |
| WO | WO 96/18605 | 6/1996 | |
| WO | WO 98/04569 | 2/1998 | |
| WO | WO 99/25352 | 5/1999 | |
| WO | WO 99/61026 A1 | 12/1999 | |
| WO | WO 00/16755 | 3/2000 | |
| WO | WO 00/25797 A1 | 5/2000 | |
| WO | WO 0064427 A2 | 11/2000 | |
| WO | WO 01/64221 A1 | 9/2001 | |
| WO | WO 02/08241 A2 | 1/2002 | |
| WO | WO 02/062123 A2 | 8/2002 | |
| WO | WO 02/068058 A2 | 9/2002 | |
| WO | WO 02/070518 A1 | 9/2002 | |
| WO | WO 03/045327 A2 | 6/2003 | |
| WO | WO 03/059327 | 7/2003 | |
| WO | WO 2004/052296 | 6/2004 | |
| WO | WO 2004/064845 * | 8/2004 | ........... A61K 31/675 |
| WO | WO 2004/064845 A1 | 8/2004 | |
| WO | WO 2005/021001 A1 | 3/2005 | |
| WO | WO 2006/135932 A2 | 12/2006 | |
| WO | WO 2006/135933 A2 | 12/2006 | |
| WO | WO 2006/135993 A1 | 12/2006 | |
| WO | WO 2007/068934 A2 | 6/2007 | |
| WO | WO 2010/017343 A2 | 2/2010 | |
| WO | WO 2012/003413 A1 | 1/2012 | |
| WO | WO 2012/068535 | 5/2012 | |

OTHER PUBLICATIONS

"Atripla Fact Sheet", www.fda.gov, [Online], Jul. 12, 2006, pp. 1-2 retrieved from the internet www.fda.gov/cder/drug/inforpage/atripla/factsheet.htm retrieved on Jan. 31, 2007.

"Gilead Buys Triangle in $464M Deal" Pharma Marketletter, 1 page (Dec. 9, 2002).

"Gilead Captures Triangle for $464 Million," Chemical Market Reporter 262(21):1 page (Dec. 9, 2002).

"Gilead set to acquire Triangle for $464m," BT Catalyst 17(1):1 page (Jan. 1, 2003).

"Graph," and "convolute of graphs,", cited as documents D54 and D55 in opposition proeedings of EP 04701819.7, Statement of Appeal Grounds filed Jun. 24, 2011.

"HIV Treatment Information," Project Inform, (on line), Jan. 2006, pp. 1-3, retrieved from http://www.projinf.org/bn/news_013006.html [retrieved on Jan. 31, 2007].

"Lactose Anhydrous," p. 373 in Analytical Profiles of Drug Substances, vol. 20, Ed. Klaus Florey, Academic Press, Inc. (1990).

"Lactose," Handbook of Pharmaceutical Excipients, 3rd ed. pp. 276-285 (2000).

"New Uses for Tenofovir; More Questions about d4T," Project Inform Perspective 35:15-16 (2003).

Pill Encarta Dictionary, 2 pages (2009), retrieved from encarta.msn.com on Mar. 16, 2009.

"Rescriptor," Patient Prescribing Information Leaflet, 7 pages (2001).

(56) References Cited

OTHER PUBLICATIONS

"Scientific Discussion," EMEA, pp. 1/28-3/28, European Medicines Agency: (Feb. 2005).
"Time-Release," Compact Oxford English Dictionary, 1 page (2009), retrieved from www.askoxford.com/concise_oed on Mar. 12, 2009.
Adis Data Information, "Emtricitabine/Tenofovir Disoproxil Fumarate," Drugs in R & D 5(3):160-161 (2004).
Affirmation of Andrew W. Williams in Support of Plaintiffs Merck, Sharp & Dohme Corp and Bristol-Myers Squib Company Co's Opening Claim Construction Brief and Exhibits Case No. 10-CV-01851 (Dec. 2, 2011).
AIDS, Monthly Index of Medical Specialities, pp. 194-198 (2002).
Ait-Khaled, et al., "Zidovudine appears to prevent selection of K65R and L74V mutations normally selected by abacavir mono- or combination therapies not containing zidovudine" Antiviral Therapy, 2002, 7:S107 (Abstract).
Alexander et al., "Investigation of (Oxodioxolenyl)methyl carbamates as nonchiral bioreversible prodrug moieties for chiral amines," J. Med. Chem. 39:480-486, 1996.
Amended Answer and Counterclaim filed by Teva Pharmaceuticals USA, Inc and Teva Pharmaceuticals Industries, Ltd. Case No. 08-CV-10838 (Jul. 20, 2009).
Anderson, "Antiviral dynamics and sex differences of zidovudine and lamivudine triphosphate concentrations in HIV-infected individuals," AIDS 17:2159-2168 (2003).
Ansel et al., "Pharmaceutical Dosage Forms and Rug Delivery Systems," 7$^{th}$ Edition, Lippincott Williams & Wilkins, pp. 209-213 (1999).
Answer and Counterclaim against Gilead Sciences, Inc. filed by Teva Pharmaceuticals USA, Inc and Teva Pharmaceuticals Industries, Ltd. Case No. 08-CV-10838 (Feb. 5, 2009).
Answer and Counterclaim filed by Teva Pharmaceuticals USA, Inc and Teva Pharmaceuticals Industries, Ltd. Case No. 09-CV-04463 (Aug. 10, 2009).
Answer filed by Teva Pharmaceuticals USA, Inc and Teva Pharmaceuticals Industries, Ltd. Case No. 10-CV-01796 (May 10, 2010).
Answer filed by Teva Pharmaceuticals USA, Inc and Teva Pharmaceuticals Industries, Ltd. Case No. 10-CV-01851 (May 17, 2010).
Answer to Amended Complaint filed by Teva Pharmaceuticals USA, Inc and Teva Pharmaceuticals Industries, Ltd. Case No. 10-CV-01796 (Jun. 29, 2011).
Arimilli et al., "Nucleotide Analogues," U.S. Appl. No. 60/022,708, 40 pages (filed Jul. 26, 1996).
Arimilli et al., "Orally bioavailable acylic nucleoside phosphonate prodrugs: Adefovir, Dipivoxil and Bis(POC)PMPA," vol. 3 (accepted for publication), Adv. Antiviral Drug Design, 1998.
Arimilli et al., "Synthesis, in vitro biological evaluation and oral bioavailability of 9-[2-(phosphonomethoxy)propyl]adenine (PMPA) prodrugs," Antiviral Chem. & Chemo. 8(6):557-567, 1997.
Arribas et al., "Tenofovir Disoproxil Fumarate, Entricitabine and Efavirenz Compared with Zidovudine/Lamivudine and Efavirenz in Treatment-Naive Patients 144-Week Analysis," JAIDS 47(1):74-78 (2008).
Arzneiformenlehre. Ein Lehrbuch für Pharmazeuten, List et al., Eds., Wissenschaftliche Verlagsgesellschaft mbH, pp. 79 and 477 (1985).
Balzarini et al, "Differential antiherpesvirus and antiretrovirus effects of the (S) and (R) enantiomers of acyclic nucleoside phosphonates: potent and selective in vitro and in vivo antiretrovirus activities of (R)-9-(2-phosphonomethoxypropyl)-2,6-diaminopurine." Antimicrob Agents Chemother. Feb. 1993; 37(2): 332-338.
Banker, Modern Pharmaceutics, Drugs and the Pharmaceutical Sciences, p. 340, Mercel Dekker, Inc. 1996.
Bartlett et al., "Overview of the effectiveness of triple combination therapy in antiretroviral-naive HIV-1 infected adults," AIDS 15:1369-1377 (2001).

Beauchamp et al., "Amino acid ester prodrugs of acyclovir," Antivir. Chem. and Chemoth. 3(3):157-64, 1992.
Benzaria et al., "New prodrugs of 9-(2-phosphonomethoxyethyl)adenine (PMEA): Synthesis and stability studies," Nucls. & Nuclt. 14(3-5):563-565, 1995.
Benzaria et al., "Synthesis, in Vitro Antiviral Evaluation, and Stability Studies of Bis(S-acyl-2-thioethyl) Ester Derivatives of 9-[2-(Phosphonometyoxy)ethyl]adenine (PMEA) as Potential PMEA Prodrugs with Improved Oral Bioavailability," J. Med. Chem. 39:4958-4965 (1996).
Berge et al., "Pharmaceutical salts," J. Pharm. Sci. 66(1):1-19, 1977.
BioWorld Today, "About BioWorld," 1 page, http://www.bioworld.com/servlet/com.accumedia.web.Dispatcher?next=aboutUs (2010).
Blackburn et al., "DNA and RNA structure," pp. 15-81, Nucleic Acids in Chemistry and Biology, 1996.
Bloor S., Kemp S.D., Hertogs K., Alcorn T., Larder B.A. Patterns of HIV drug resistance in routine clinical practice; a survey of almost 12000 samples from the USA in 1999.—Antiviral Therapy, 5 (Suppl. 3): 132.
Borroto-Esoda et al., "In vitro evaluation of the anti-HIV activitiy and metaboloc interactions of tenofovir and emtricitabine," Antiviral Therapy 11:377-384 (2006).
Brief Communication from EPO for Application No. 067731595.0 dated Nov. 10, 2013.
Bristol Myers Squibb "Sustiva®," http://www.fda.gov/medwaTCH/SAFETY/2005/Sustiva_PI61005.pdf, pp. 3-40 (retrieved Jan. 31, 2007).
Brogan et al., "Cost-Effectiveness of Nucleoside Revers Transcriptase Inhibitor Pairs in Efavirenz-Based Regimens for Treatment-Naïve Adults with HIV Infection in the United States," Value in Health 14:657-664 (2011).
Bundgaard et al., "Design and Application of Prodrugs," pp. 113-191, Textbook of Drug Design and Development, 1991.
Byrn (editor), Solid State Chemistry of Drugs, 2nd Edition, p. 22, 1999.
Carpenter, C.C.J., et al., "Antiretroviral Therapy for HIV Infection in 1997: Updated Recommendations of the International AIDS Society—USA Panel," The Journal of the American Medical Association, Jun. 25, 1997, vol. 277, No. 24, pp. 1962-1969.
Cherry, et al., "Mutations at codon 184 in simian immunodeficiency virus reverse transcriptase confer resistance to the (−) enantiomer of 2„3'-dideoxy-3,-thiacytidine.-Antimicrob.," Agents Chemother. 41:2763-2765, 1997 (retrieved from http://aac.asm.org/content/41/12/2763.full.pdf+html retrieved on Jan. 30, 2014).
Cipla Ltd. (Opponent), Pre-Grant Opposition against Indian patent application 3383/DELNP/2005A (Dec. 11, 2007).
Colla et al., "Synthesis and antiviral activity of water-soluble esters of acyclovir [9-[(2-Hydroxyethoxy)methyl]guanine]," J. Med. Chem. 26:602-04, 1983.
Communication about intention to grant a European patent for Patent Publication EP 1583542 (Application No. 04701819.7) issued by the European Patent Office (Nov. 5, 2007).
Communication and Annex for Patent Publication EP 1583542 (Application No. 04701819.7) issued by the European Patent Office (Jul. 17, 2007).
Communication and Annex for Patent Publication EP 1583542 (Application No. 04701819.7) issued by the European Patent Office (Jul. 26, 2006).
Communication and Annex for Patent Publication EP 1583542 (Application No. 04701819.7) issued by the European Patent Office (Oct. 24, 2005).
Communication and Annex issued by the European Patent Office for Application No. 067731595.0 dated Jul. 9, 2013, 12 pages.
Communication concerning Correction of the EP Specification for Patent Publication EP 1583542 (Application No. 04701819.7) issued by the European Patent Office (Jul. 22, 2008).
Communication from EPO for Application No. 067731595.0 dated Nov. 15, 2013.
Communication from EPO for Application No. 067731595.0 dated Dec. 4, 2013.
Communication from the Examining Division of the EPO for EP 1890681 B1 (Application No. 06773194.3) (May 13, 2009).

(56) References Cited

OTHER PUBLICATIONS

Communication of further notices of opposition pursuant to Rule 79(2) EPC for EP 1583542 B1 (Application No. 04701819.7) and Request to File Observations (Apr. 23, 2009).
Communication of Intent to Grant EP 1890681 B1 (Application No. 06773194.3) and Druckexemplar issued by the European Patent Office (Jul. 15, 2008).
Communication of Notice of Opposition of EP 1583542 B1 (Application No. 04701819.7)—first information to the patent proprietor (Mar. 24, 2009).
Communication of Notice of Opposition of EP 1583542 B1 (Application No. 04701819.7)—first information to the patent proprietor (Mar. 26, 2009).
Communication of notices of opposition pursuant to Rule 79(2) EPC for EP 1890681 B1 (Application No. 06773194.3) and Request to File Observations (Nov. 12, 2009).
Communication pursuant to Article 94(3) EPC for Patent Publication EP 1923063 (Application No. 08152527.1) issued by the European Patent Office (Mar. 26, 2012).
Communication pursuant to Article 94(3) EPC for Patent Publication EP 1923063 (Application No. 08152527.1) issued by the European Patent Office (Sep. 4, 2009).
Complaint for Patent Infringement against Teva Pharmaceuticals USA, Inc and Teva Pharmaceuticals Industries, Ltd. filed by Gilead Sciences, Inc. and Emory University Case No. 10-CV-01798 (Mar. 5, 2010).
Complaint for Patent Infringement against Teva Pharmaceuticals USA, Inc and Teva Pharmaceuticals Industries, Ltd. filed by Gilead Sciences, Inc. Case No. 09-CV-04463 (May 8, 2009).
Complaint for Patent Infringement against Teva Pharmaceuticals USA, Inc and Teva Pharmaceuticals Industries, Ltd. filed by Gilead Sciences, Inc. Case No. 10-CV-01796 (Mar. 5, 2010).
Complaint for Patent Infringement against Teva Pharmaceuticals USA, Inc and Teva Pharmaceuticals Industries, Ltd. filed by Merck, Sharp & Dohme Corp and Bristol-Myers Squib Company. Case No. 10-CV-01851 (Mar. 9, 2010).
Conference Call Transcript—Gilead Sciences Conference call to Discuss Triangle Pharmaceuticals Acquistion. Event Date/Time Dec. 4, 2002/ 9:00 AM ET (11 pages).
Correction of an Error in the Decision According to Rule 140 EPC for EP 1890681 B1 (Application No. 06773194.3) (Jul. 5, 2011).
Crowley, "Drug-Excipient Interactions," Pharm. Tech., 6 pages (2001).
Dahl et al., Amended Transmittal of U.S. Appl. No. 10/540,794, Compositions and methods for combination antiviral therapy, filed Mar. 20, 2006.
Dando et al., "Emtricitabine/Tenofovir Disoproxil Fumarite," Drugs 64(18):2075-2082 (2004).
Davidsen et al., "N-(Acyloxyalkyl)pyridinium salts as soluble prodrugs of a potent platelet activating factor antagonist," J. Med. Chem. 37(26):4423-4429, 1994.
De Clercq et al., "(S)-9-(2,3-dihydroxypropyl)adenine: An aliphatic nucleoside analog with broad spectrum antiviral activity," Science 200:563-565, 1978.
De Clercq et al., "New Developments in Anti-HIV Chemotherapy," Curr. Med. Chem. 8(13):1543-1572 (2001).
De Clercq et al., "New developments in anti-HIV chemotherapy," Farmaco 56(1-2):3-12 (2001).
De Clercq, "Antiviral drugs: current state of the art," J. Clin. Virol. 22:73-89 (2001).
De Clercq, "Highlights in the Development of New Antiviral Agents," Mini-Rev. Med. Chem. 2(2):163-175 (2002).
De Clercq, "New Anti-HIV Agents and Targets," Medicinal Research Reviews 22(6):531-565 (2002).
De Clercq, "New developments in anti-HIV chemotherapy," Biochem Biophys Acta 1587(2-3):158-175 (2002).
De Lombaert et al., "N-Phosphonomethyl Dipeptides and their Phosphonate Prodrugs, a New Generation of Neutral Endopeptidase (NEP, EC 3.4.24.11) Inhibitor," J. Med. Chem. 37:498-511 (1994).

Decision to Refuse a European Patent Application issued by the European Patent Office for Application No. 08152527.1, dated Jan. 7, 2016, 12 pages.
Decision of Hearing of the Indian Patent Office for Patent Application No. 3383/DELNP/2005 (Mar. 25, 2009).
Decision of Rejection for Application No. 7000806/1999 issued by the Korean Intellectual Property Office (Jan. 20, 2006) (translation).
Decision of Rejection for Patent Application No. 7000636/2000 issued by the Korean Intellectual Property Office (May 10, 2006) (translation).
Decision of Rejection for Patent Application No. 7007002/2008 issued by the Korean Intellectual Property Office (Jan. 7, 2009) (translation).
Decision of Rejection for Patent Application No. 86110757 issued by the Intellectual Property Office of Taiwan (Nov. 11, 1999) (translation).
Decision of Rejection for Patent Application No. 87112168 issued by the Taiwanese Intellectual Property Office (Apr. 6, 2001) (translation).
Decision of the Opposition Division for EP Patent EP 1583542 B1 (Application No. 04701819.7), Claims, Grounds for the Decision and Provision of the minutes (Jan. 31 and Feb. 14, 2011).
Decision to grant a European patent for EP Appln No. 04701819.7 and Druckexemplar (May 23, 2008).
Decision to Grant Patent Application No. 06773194.3 (EP 1890681B1 ) issued by the European Patent Office (Dec. 11, 2008).
Declaration of Robin D. Rogers, Ph.D. in Support of Teva's Claim Constructions and Exhibits Case No. 10-CV-01851 (Jan. 13, 2012).
Declaration of Adam C. LaRock in Support of Plaintiffs' Claim Constructions and Exhibits filed by Gilead Sciences, Inc., Emory University Case No. 08-CV-10838 (Nov. 4, 2011).
Declaration of Adam C. LaRock in Support of Plaintiffs' Rebuttal Claim Constructions and Exhibits filed by Gilead Sciences, Inc., Emory University Case No. 08-CV-10838 (Dec. 16, 2011).
Declaration of Allan S. Myerson in Support of Plaintiffs' Claim Constructions and Exhibits filed by Gilead Sciences, Inc. Case No. 10-CV-01796 (Dec. 2, 2011).
Declaration of Andrew W. Williams in Support of Plaintiffs Merck, Sharp & Dohme Corp and Bristol-Myers Squib Company Co's Rebuttal Claim Construction Brief and Exhibits Case No. 10-CV-01851 (Jan. 13, 2012).
Declaration of Colleen Tracy in Support of a Motion for Leave to File Amended Complaint Case No. 10-CV-01796 (Apr. 11, 2011).
Declaration of Daniel P. Margolis in Support of Teva's Opening Claim Construction Brief and Exhibits filed by Teva Pharmaceuticals USA, Inc and Teva Pharmaceuticals Industries, Ltd. Case No. 10-CV-01796 (Dec. 2, 2011).
Declaration of Daniel P. Margolis in Support of Teva's Rebuttal Claim Construction Brief and Exhibits filed by Teva Pharmaceuticals USA, Inc and Teva Pharmaceuticals Industries, Ltd. Case No. 10-CV-01796 (Jan. 13, 2012).
Declaration of Daniel P. Margolis in Support of Teva's Rebuttal Claim Construction Brief and Exhibits filed by Teva Pharmaceuticals USA, Inc and Teva Pharmaceuticals Industries, Ltd. Case No. 08-CV-10838 (Dec. 16, 2011).
Declaration of James Galbraith in Opposition of a Motion for Leave to File Amended Complaint Case No. 10-CV-01796 (Apr. 25, 2011).
Declaration of Karen C. Shen in Support of Teva's Opening Claim Construction Brief and Exhibits Case No. 10-CV-01851 (Dec. 2, 2011).
Declaration of Michael J. Freno in Support of Teva's Opening Claim Construction Brief and Exhibits filed by Teva Pharmaceuticals USA, Inc and Teva Pharmaceuticals Industries, Ltd. Case No. 08-CV-10838 (Nov. 4, 2011).
Declaration of Natalie Lieber and Exhibits filed by Gilead Sciences, Inc. Case No. 10-CV-01796 (Dec. 2, 2011).
Declaration of Natalie Lieber in Support of Plaintiffs' Rebuttal Claim Constructions and Exhibits filed by Gilead Sciences, Inc. Case No. 10-CV-01796 (Jan. 13, 2012).
Declaration of Paul A. Bartlett in Support of Plaintiffs' Claim Constructions and Exhibits filed by Gilead Sciences, Inc., Emory University Case No. 08-CV-10838 (Nov. 4, 2011).

(56) References Cited

OTHER PUBLICATIONS

Declaration of Slaven Jesic in Support of Teva's Rebuttal Claim Construction Brief and Exhibits Case No. 10-CV-01851 (Jan. 13, 2012).
Defendants' Memorandum in Opposition to Plaintiff's Pretrial Memorandum filed by Teva Pharmaceuticals USA, Inc and Teva Pharmaceuticals Industries, Ltd. Case No. 10-CV-01796 (Jan. 28, 2013).
Defendants' Memorandum in Opposition to Plaintiff's Pretrial Memorandum filed by Teva Pharmaceuticals USA, Inc and Teva Pharmaceuticals Industries, Ltd. Case No. 10-CV-01851 (May 24, 2013).
Defendants' Notice Pursuant to 35 U.S.C. § 282 filed by Merck, Sharp & Dohme Corp and Bristol-Myers Squib Company Co. Case No. 10-CV-01851 (May 22, 2013).
Defendants' Pretrial Memorandum filed by Teva Pharmaceuticals USA, Inc and Teva Pharmaceuticals Industries, Ltd. Case No. 10-CV-01796 (Jan. 14, 2013).
Defendants' Pretrial Memorandum filed by Teva Pharmaceuticals USA, Inc and Teva Pharmaceuticals Industries, Ltd. Case No. 10-CV-01851 (May 10, 2013).
Defendants' Proposed Findings of Fact and Conclusions of Law filed by Teva Pharmaceuticals USA, Inc and Teva Pharmaceuticals Industries, Ltd. Case No. 10-CV-01796 (Jan. 14, 2013).
Defendants' Proposed Findings of Fact and Conclusions of Law filed by Teva Pharmaceuticals USA, Inc and Teva Pharmaceuticals Industries, Ltd. Case No. 10-CV-01851 (May 10, 2013).
Delehanty et al. Slides from the oral presentation for "A Randomized Study of Three Doses of FTC Versus 3TC in HIV-Infected Patients," 6th CROI (Jan. 31-Feb. 4, 1999) Chicago.
Delehanty et al., "A Phase I/II Randomized, Controlled Study of FTC Versus 3TC in HIV-Infected Patients," 6th CROI (Jan. 31-Feb. 4, 1999) Chicago, Session 5, Abstract 16.
Delehanty J., et al., "Selection of FTC dose based on viral kinetics and pharmacokinetics in an accelerated clinical trial design," *12th World AIDS Conference*, Geneva, Switzerland, Jul. 1998, abstract No. 12208 retrieved from http://www.aegis.org/DisplavContent/print.aspx?Section1D=341007 on Jan. 30, 2014.
Department of Health and Human Services, "Guidelines for the Use of Antiretroviral Agents in HIV-1-1nfected Adults and Adolescents," pp. 1, 33-49 (Nov. 3, 2008).
Gibson, Mark (editor) Drugs and the Pharmaceutical Sciences, Pharmaceutical Preformulation and Formulation, vol. 199, p. 60 (2009).
Endorsed Letter to Judge Richard J. Sullivan Case No. 10-CV-01796 (Jan. 13, 2012).
Engel, R., "Phosphonates as analogues of natural phosphates," Chem. Rev. 77(3):349-367, 1977.
European Search Report, EP 2386294 (Application No. 11167101.2), 15 pages (Dec. 29, 2011).
Examination Report for Patent Application No. 540728 issued by the Intellectual Property Office of New Zealand (Apr. 24, 2007).
Examination Report Patent Application No. 564045 issued by the Intellectual Property Office of New Zealand (Oct. 6, 2009).
Examiner's First Report on Patent Application No. 2009200414 issued by the Australian Patent Office (Feb. 24, 2010).
Examiner's First Report on Patent Application No. 85827/98 issued by the Australian Patent Office (Feb. 28, 2001).
Examiner's First Report Patent Application No. 20026257795 issued by the Australian Patent Office (Sep. 29, 2009).
Examiner's Remarks for patent Application No. a 2008 00493 issued by the Ukranian Patent Office (2010).
Examiner's Second Report on Patent Application No. 2009200414 issued by the Australian Patent Office (Aug. 29, 2011).
Examiner's Second Report on Patent Application No. 85827/98 issued by the Australian Patent Office (Mar. 27, 2002).
Examiner's First Report on Patent Application No. 2004206821 issued by the Australian Patent office (Aug. 28, 2007).
Examiner's Remarks for Patent Application No. 200501134/28 issued by the Eurasian Patent Office (translation).
Examiner's Second Report on Patent Application No. 2004206821 issued by the Australian Patent office (Aug. 20, 2008).
Excerpt of the Merck Veterinary Manual (Clarence M. Fraser et al. eds., 7th ed., 1991).
Excerpts from Daniel S. Kemp & Frank Vellaccio, Organic Chemisty (Worth Publishers, Inc. 1980)x.
Excerpts from K. Peter C. Vollhardt, Organic Chemistry (W.H. Freeman and Company 1987).
Excerpts of "Teva Pharmaceuticals USA, Inc.'s Detailed Statement of the Factual and Legal Bases for Its Opinion That U.S. Pat. No. 5,814,639, U.S. Pat. No. 5,914,331, U.S. Pat. No. 5,922,695, U.S. Pat. No. 5,935,946, U.S. Pat. No. 5,977,089, and U.S. Pat. No. 6,043,230 are Invalid, Unenforceable or Not Infringed by the Manufacture, Use or Sale Oflts Emtricitabine & Tenofovir Disoproxil Fumarate Tablets, 200 mg/300 mg" dated Jan. 28, 2010 ("2010 Detailed Statement").
Teva Pharmaceuticals USA, Inc.'s Detailed Statement of the Factual and Legal Bases for Its Opinion That U.S. Pat. No. 5,922,695, U.S. Pat. No. 5,935,946, U.S. Pat. No. 5,977,089, and U.S. Pat. No. 6,043,230 are Invalid, Unenforceable or Not Infringed by the Manufacture, Use or Sale OfTenofovir Disoproxil Fumarate Tablets, 300 mg dated Jan. 25, 2010 ("2010 Detailed Statement"), 3 pages.
Excerpts of "Teva Pharmaceuticals USA, Inc.'s Detailed Statement of the Factual and Legal Bases for Its Opinion That U.S. Pat. No. 6,642,245 and U.S. Pat. No. 6,703,396 are Invalid, Unenforceable or Not Infringed by the Manufacture, Use or Sale of Its Emtricitabine & Tenofovir Disoproxil Fumarate Tablets, 200 mg/300 mg" dated Nov. 3, 2008 ("2008 Detailed Statement"); "Teva Pharmaceuticals USA, Inc.'s Detailed Statement of the Factual and Legal Bases for Its Opinion That U.S. Pat. No. 6,642,245 and U.S. Pat. No. 6,703,396 Are Invalid, Unenforceable or Not Infringed by the Manufacture, Use or Sale of Its Efavirenz/Emtricitabine/Tenofovir Disoproxil Fumarate Tablets, 600 mg/200 mg/300 mg" dated Mar. 30, 2009 ("2009 Detailed Statement"); and "Teva Pharmaceuticals USA, Inc.'s Detailed Statement of the Factual and Legal Bases for Its Opinion That U.S. Pat. No. 5,814,639, U.S. Pat. No. 5,914,331, U.S. Pat. No. 5,922,695, U.S. Pat. No. 5,935,946, U.S. Pat. No. 5,977,089 and U.S. Pat. No. 6,043,230 are Invalid, Unenforceable or Not Infringed by the Manufacture, Use or Sale of Its Emtricitabine & Tenofovir Disoproxil Fumarate Tablets, 200 mg/300 mg" dated Jan. 28, 2010 ("2010 Detailed Statement").
Excerpts of Panel on Antiretroviral Guidelines for Adults and Adolescents, Department of Health and Human Services, Guidelines for the use of antiretroviral agents in HIV-1-infected adults and adolescents 1-167 (2011 ), 3 pages.
Excerpts of the Gilead Sciences, Inc., Q2, 2011 Earnings Results Conference Call and Webcast presentation pp. 16 & 19 (Jul. 26, 2011).
Excerpts of the Gilead Sciences, Inc., Q2, 2011 Earnings Results Conference Call and Webcast presentation, p. 16-18 (Jul. 26, 2011).
Extended European Search Report for Patent Publication EP 1923063 (Application No. 08152527.1) issued by the European Patent Office (Mar. 10, 2009).
Eyjolfsson, "Lisinopril-Lactose Incompatibility," Drug Devel. Indust. Pharm. 24(8):797-798 (1998).
Farquhar et al., "Biologically Reversible Phosphate-Protective Groups," J. Pharm. Sci. 72:324-325 (1983).
Farquhar et al., "Synthesis and antitumor evaluation of Bis[(pivaloxy)methyl] 2'-deoxy-5-fluorouridine 5'-monophosphate (FdUMP): a strategy to introduce nucleotides into cells," *J Med. Chem.* 37(23):3902-03, 1994.
Fasman et al., pp. 385-394, Practical Handbook of Biochem. and Molec. Biol., 1989.
FDA: "Guidance for industry fixed dose combination and co-packaged drug products for treatment of HIV" www.fda.org. [on line], May 2004, pp. 1-17, (retrieved from http://www.fda.gov/oc/initiatives/hiv/hivguidance.html>[retrieved on Jan. 31, 2007].
Fell et al., "The tensile strength of lactose tablets" J. Pharm. Pharmacol. 20:657-659 (1968).

(56) References Cited

OTHER PUBLICATIONS

Feng et al. 2009 "The triple combination of tenofovir, emtricitabine and efavirenz show synergistic anti-HIV-1 activity in vitro: a mechanism of action study," Retrovirology 6:44, http://www.retrovirology.com/content/6/1/44.

Feng, J. et al, "Mechanistic studies show that 9-)-FTC-TP is a better inhibitor of HIV-1 reverse transcriptase than 3TC-TP," FASEB 13:1511-1517 (1999).

Final Office Action for Patent Application No. 86110757 issued by the Intellectual Property Office of Taiwan (Sep. 5, 2000) (translation).

Final Office Action for Patent Application. No. 89123708 issued by the Intellectual Property Office of Taiwan (Apr. 12, 2001) (translation).

First Amended Complaint for Patent Infringement filed by Gilead Sciences, Inc. Case No. 10-CV-01796 (Jun. 15, 2011).

First Amended Complaint for Patent Infringement against Teva Pharmaceuticals USA, Inc and Teva Pharmaceuticals Industries, Ltd. filed by Gilead Sciences, Inc., Emory University Case No. 08-CV-1083 8 (Jul. 1, 2009).

First Examination Report for Application No. 564102 Issued by the Intellectual Property Office of New Zealand (Oct. 6, 2009).

First Examination Report for Patent Application No. 3383/DELNP/2005 from the Indian Patent Office (Jul. 31, 2007).

First Examination Report for Patent Application No. 602/DEL/2007 issued by the Indian Patent Office (Nov. 18, 2009).

First Examination Report for Patent Application No. 6665/DELNP/2008 issued by the Indian Patent Office (Jun. 30, 2011).

First Office Action for Patent Application No. 200410046290.X issued by the Chinese Patent Office (Jun. 17, 2005) (translation).

First Office Action for Patent Application No. 200480002190.5 issued by the Patent Office of the People's Republic of China (Aug. 4, 2006).

First Office Action for Patent Application No. 200510099916.8 issued by the Chinese Patent Office (Jun. 15, 2007) (translation).

First Office Action for Patent Application No. 97197460.8 issued by the Chinese Patent Office (Jan. 16, 2004) (translation).

First Official Action for Patent Application No. a 2008 00555 issued by the Ukrainian Patent Office (2011) (translation).

Fischl, Margaret A. et al., Prolonged Zidovudine Therapy in Patients with AIDS and Advanced AIDS-Related Complex, 262 J.A.M.A. 2405 (1989).

Fiske et al., "Pharmacokinetics, safety and tolerability of single escalating doses of DMP 266, an HIV non-nucleoside reverse transcriptase inhibitor, in healthy volunteers," Pharm. Res. 14(11 Suppl.):S609 (1997).

Flaherty et al., "Synthesis and selective monoamine oxidase B-inhibiting properties of 1-Methyl-1,2,3,6-tetrahydropyrid-4-yl carbamate derivatives: potential prodrugs of (R)- and (S)-Nordeprenyl," J. Med. Chem. 39:4759-4761, 1996.

Flexner, C., "HIV-Protease Inhibitors," the New England Journal of Medicine, Apr. 30, 1998, vol. 338, No. 18, pp. 1281-1292.

Folkmann et al., "Acyloxymethyl carbonochloridates. New intermediates in prodrug synthesis," Synthesis, pp. 1159-1166, 1990.

Fourth Amended Answer filed by Teva Pharmaceuticals USA, Inc and Teva Pharmaceuticals Industries, Ltd. Case No. 08-CV-10838 (Oct. 17, 2011).

Fourth Amended Complaint for Patent Infringement against Teva Pharmaceuticals USA, Inc and Teva Pharmaceuticals Industries, Ltd. and Exhibits filed by Gilead Sciences, Inc., Emory University Case No. 08-CV-10838 (Oct. 3, 2011).

Frampton et al., "Emtricitabine: A Review of Its Use in the Management of HIV Inspection," Drugs 65(10):1427-1448 (2005).

Freeman et al., "3 Prodrug Design for Phosphate and Phosphonates," Progress in Medicinal Chemistry 34:112-147 (1997).

Fridland, "Tenofovir," Curr. Opin. Anti-Infect. Invest. Drugs 2(3):295-301 (2000).

FTC 101 Virology analysis, TPI Document No. 14022 (2002), 10 pages.

Fung et al., "Tenofovir Disoproxil Fumarate: A Nucleotide Reverse Transcriptase Inhibitor for the Treatment of HIV Infection," Clin. Therapeutics 24(10):1515-1548 (2002).

Further Examination Report for Patent Application No. 540728 issued by the Intellectual Property Office of New Zealand (Feb. 11, 2008).

Further Examination Report for Patent Application No. 540728 issued by the Intellectual Property Office of New Zealand (Jun. 18, 2008).

Gallant, et al., "Early Non-Response to Tenofovir DF (TDF) + Abacavir (ABC) and Lamivudine (3TC) in a Randomized Trial Compared to Efavirenz (EFV) + ABC and 3TC: ESS30009 Unplanned Interim Analysis" Abstr Intersci Conf Antimicrob Agents Chemother Intersci Conf Antimicrob Agents Chemother, 2003, Abstract No. H-1722a.

Generics [UK] Limited, Notice of Opposition of EP Patent EP 1583542B1 (Application No. 04701819.7) (Mar. 18, 2009).

Generics [UK] Limited, Written Submission in preparation for Oral Proceedings for EP Patent EP 1583542 B1 (Application No. 04701819.7) (Sep. 17, 2010).

Gilead "Truvada®," http://www.fda.gov/medwatch/SAFETY/2005/Oct_PI/Truvada_PI.pdf, pp. 1-29 (retrieved Jan. 31, 2007).

Gilead Sciences Inc., Appeal Grounds against the Decision of the Opposition Division for EP 1890681 B1 (Application No. 06773194.3) (Oct. 17, 2011).

Gilead Sciences Inc., Notice of Appeal against the Decision of the Opposition Division for EP 1890681 B1 (Application No. 06773194.3) (Aug. 16, 2011).

Gilead Sciences Inc., Written Submission in preparation for Oral Proceedings for the Opposition of EP 1890681 B1 (Application No. 06773194.3) (Feb. 4, 2011).

Gilead Sciences Inc., Written Submission in preparation for Oral Proceedings for the Opposition of EP 1890681 B1 (Application No. 06773194.3) (Mar. 2 & 4, 2011).

Gilead Sciences Inc., Written Submission in preparation to/during Oral Proceedings for EP Patent EP 1583542 B1 (Application No. 04701819.7) (Sep. 17, 2010).

Gilead Sciences, Inc., "Data Comparing Viread (R) and Emtriva (R) to Combivir (R) as Part of Combination HIV Therapy Published in New England Journal of Medicine," p. 1-5, Press Release, 2006.

Gilead Sciences, Inc., "Gilead Sciences to Acquire Triangle Pharmaceuticals for $464 Million; Gilead to Launch Coviracil in 2003; Will Develop Co-Formulation of Viread and Coviracil," 2 pages, Press Release (2002).

Gilead Sciences, Inc., "U.S. FDA Approves Gilead Sciences' Emtriva A one-capsule, Once-Daily Medication for the Treatment of HIV," pp. 3-7, Press Release, 2003.

Gilead Sciences, Inc., Physician Insert for Truvada, pp. 1-30 (2007).

Gilead, Bristol-Myers Squibb "Atripla™,"http://www.fda.gov/cder/foi/;abe;/2006/021937lbl.pdf, pp. 4-53 (retrieved Jan. 31, 2007).

Gilead: "Bristol-Myers Squibb and Gilead announce data supporting bioequivalence for single PIII fixed dose regimen of Sustiva® (efavirenz) and Truvada® (emtricitabine and tenofovir fumarate)" Gilead Press Release (online Jan. 9, 2006), pp. 1-5, retrieved from http://www.gilead.com/press.

Gilead: "Gilead provides update on development of fixed-dose regimen of Truvada (emtricitabine and tenofovir disoproxil fumarate) and Sustiva (efavirenz)," Gilead Press Release, [on line], Apr. 26, 2005, pp. 1-3, retrieved from http://www.gilead.com/press.

Giron, "Applications of thermal analysis in the pharmaceutical industry," J. Pharm. Biomed. Anal. 4(6):755-770 (1986).

Glaxo Marketing Material, Epivir + Ziagen, 6 pages (2003).

Gosselin, et al., "Anti-human immunodeficiency virus activities of the (3-L enantiomer of 2',3'-dideoxycytidine and its 5-fluoro derivative in vitr," Antimicrob Agents Chemother 38: 1292-1297, 1994 retrieved from http://aac.asm.org/content/38/6/1292.full.pdf on Jan. 30, 2014.

Hammer et al., "Ether, carbonate and urethane deoxynucleoside derivatives as prodrugs," Acta Chemica Scandinavia 50:609-622, 1996.

Harada, Shinji et al., Infection of HTLV-IIIILAV in HTLV-I-Carrying Cells MT-2 and MT-4 and Application in a Plaque Assay, 229 Science 563 (1985).

(56) References Cited

OTHER PUBLICATIONS

Harrigan, P.R., et al., "Phenotypic susceptibilities to tenofovir in a large panel of clinically derived human immunodeficiency virus type 1 isolates," *Antimicrob Agents Chemother.* 46:1067-1072, 2002 (retrieved from http://aac.asm.Org/content/46/4/1067.full.pdf+html on Jan. 30, 2014.
Harris et al., "Genotypic Analysis of HIV-1 Infected ART Naive Patients Receiving Emtricitabine (FTC) or Lamivudine (3TC) in a Double Blind Equivalence Trial," 5[th]International Workshop on Drug Resistance and Treatment Strategies, Jun. 4-8, No. 104 (2001).
Havlir et al., "In Vivo Antagonism with Zidovudine plus Stavudine Combination Therapy," J. Infect. Disease 182:321-325 (2000).
Hazen et al., "Relative Anti-HIV-1 Efficacy of Lamivudine and Emtricitabine In Vitro Is Dependent on Cell Type," J. AIDS 32:255-258 (2003).
Hoong, Lee K. et al., Enzyme-Mediated Enantioselective Preparation of Pure Enantiomers of the Antiviral Agent 2',3'-Dideoxy-5-.fluoro- 3'-thiacytidine (FTC) and Related Compounds, 57 J. Organic Chemistry 5563 (1992).
Hostetler et al., "Greatly Enhanced Inhibition of Human Immunodeficiency Virus Type 1 Replication in CEM and HT 4-6C Cells by 3'-Deoxythymidine Diphosphate Dimyristoylglycerol, a Lipid Prodrug of 3'-Deoxythymidine," Antimicro. Agent Chemo. 36(9):2025-2029 (1992).
Hostetler et al.., "Synthesis and Antiretroviral Activity of Phospholipid Analogs of Azidothymidine and Other Antiviral Nucleosides," J. Biol. Chem. 265(11):6112-6117 (1990).
Huff, "Five New Drugs Enter the Homestretch," The Body: The Complete HIV/AIDS Resource, 3 pages (2002).
Ibbotson et al., Drugs 2003, 63(11), 1089-1096.
Ikeda et al., "Studies of prodrugs III. A convenient and practical preparation of Amphicillin prodrugs," Chem. Pharm. Bull. 32:4316-4322, 1984.
Information about the Results of Oral Proceedings for EP Patent EP 1583542 B1 (Application No. 04701819.7), Claims, Amended Claims and Minutes of the Oral Proceeding (Nov. 19, 2010).
Information About the Results of the Oral Proceedings for EP 1890681 B1 (Application No. 06773194.3) (Apr. 5, 2011).
International Preliminary Report on Patentability for PCT/US2004/000832 (Dec. 29, 2004).
International Preliminary Report on Patentability for PCT/US2006/023222 (Oct. 8, 2007).
International Preliminary Report on Patentability for PCT/US2006/023223 (Oct. 8, 2007).
International Search Report and Written Opinion mailed Jul. 12, 2004 for PCT/US2004/000832, Int'l. Filing Date Jan. 13, 2004.
International Search Report for PCT/US1997/013244 (Oct. 20, 1997).
International Search Report for PCT/US1998/015254 (Nov. 25, 1998).
International Search Report for PCT/US2006/023222 (Feb. 23, 2007).
International Search Report for PCT/US2006/023223 (Feb. 23, 2007).
Ishida and Asao, "Self-association and unique DNA binding properties of the anti-cancer agent TAS-103, a dual inhibitor of topoisomerases I and II," Biochem. Biophys. Acta 1587(2-3):155-163 (2002).
Iyer et al., "Synthesis of acyloxyalkyl acylphosphonates as potential prodrugs of the antiviral Trisodium phosphonoformate (Foscarnet sodium)," Tet. Lett. 30(51): 7141-7144, 1989.
Jamsek, et al. "Poor Virological Responses and Early Emergence of Resistance in Treatment Naïve, HIV-infected Patients Receiving a Once Daily Triple Nucleoside Regimen of Didanosine, Lamivudine, and Tenofovir DF" 11th Conf Retrovir Oppor Infect, 2004, Abstract No. 51.
Jones et al.., "Minireview: nucleotide prodrugs," Antiviral Res. 27:1-17 (1995).

Kearney et al., "Effect of Demographic Variables on the Pharmacokinetics of Tenofovir DF in HIV-Infected Patients and Healthy Subjects," 41st ICAAC Abstracts, Chicago, IL, Sep. 22-25, 2001, Abstract A-504.
Khamnei et al., "Neighboring Group Catalysis in the Design of Nucleotide Prodrugs," J. Med. Chem. 39:4109-4115 (1996).
King et al. "Potency of Nonnucleoside Reverse Transcriptase Inhibitors (NNRTIs) Used in Combination with Other Human Immunodeficiency Virus NNRTIs, NRTIs, or Protease Inhibitors," Antimicrobial Agents and Chemotherapy 46(6):1640-1646 (2002).
Kleinebudde et al. European journal of Pharmaceutics and Biopharmaceutics, 2004, 58, 317-326.
Krise et al., "Prodrugs of phosphates, phosphonates, and phosphinates," Advanced Drug Delivery Reviews 19:287-310, 1996.
Kucera et al., "Novel Membrane-Interactive Ether Lipid Analogs That Inhibit Infectious HIV-1 Production and Induce Defective Virus Formation," AIDS Res. & Hum. Retro. 6:491-501 (1990).
Kusmierek et al., "Kinetics and Mechanisms of Hydrolytic Reactions of Methylated Cytidines under Acidic and Neutral Conditions," Acta Chem. Scand. 43:196-202 (1989).
Lachman, et al. (1987) "The Theory and Practice of Industrial Pharmacy", Varghese Publishing House, Dadar Bombay, pp. 330-331.
Landgrebe, J. A., "Crystallization and filtration," Theory and Practice in the Organic Laboratory, 3rd Edition, pp. 65-77, 1982.
Lanier, et al. "Prediction of NRTI Optins by Linking Reverse Transcriptase Genotype to Phenotypic Breakpoints" 10th Conf Retrovir Oppor Infect , 2003, Abstract No. 586.
Larder, Brendan A. et al., HIV with Reduced Sensitivity to Zidovudine (AZT) Isolated During Prolonged Therapy, 243 Science 1731 (1989).
Letter Regarding the Opposition Procedure for EP Patent EP 1583542 B1 (Application No. 04701819.7) (Mar. 11, 2010).
Lieberman et al., "," Pharmaceutical Dosage Forms 1:177-178 (1989).
Lindahl et al., "Synthesis of an acyloxymethyl prodrug of the Inositol phosphate alpha-Trinositol," J. Carbohydrate Chemistry 15(5):549-554, 1996.
Lindahl, "Instability and decay of the primary structure of DNA," Nature 362:709-715 (1993).
Litigation.
Liu et al., "Thymidylate synthase as a translational regulator of cellular gene expression," Biochem. Biophys. Acta 1587(2-3):174-182 (2002).
Loveday, "Nucleoside reverse transcriptase inhibitor resistance," JAIDS 26:S10-S24 (2001).
Lu, et al., "Determination of Clinical Cut-Offs for Reduced Response to Tenofovir DF therapy in Antiretroviral-Experienced Patients" Antiviral Therapy, 2002, vol. 7(Suppl 1), S104, Abstract No. 125.
Maillard et al., "Adenosine receptor prodrugs: Synthesis and biological activity of derivatives of potent A1-selective agonists," J. Pharm. Sci. 83(1):46-53, 1994.
Marcelin et al., "Resistance profiles of emtricitabine and lamivudine in tenofovir-containing regimens," J. Antimicrob. Chemother. 67:1475-1478 (2012).
Margot et al., "Development of HIV-1 Drug Resistance Through 144 Weeks in Antiretroviral-Naive Subjects on Emtricitabine, Tenofovir Disoproxil Fumarate, and Efavirenz Compared with Lamivudine/Zidovudine and Efavirenz in Study GS-01-934," JAIDS 52(2):209-221 (2009).
Margot et al., "Genotypic and phenotypic analyses of HIV-1 in antiretroviral-experienced patients treated with tenofovir DF," AIDS 16:1227-1235 (2002).
Margot et al., "In Vitro Human Immunodeficiency Virus Type 1 Resistance Selections with Combinations of Tenofovir and Emtricitabine or Abacavir and Lamivudine," Antimicrobial Agents and Chemotherapy 50(12):4087-4095 (2006).
Margot et al., "Resistance development over 144 weeks in treatment-naive patients receiving tenofovir disoproxil fumarate or stavudine with lamivudine and efavirenz in Study 903," HIV Medicine 7:442-450 (2006).

(56) References Cited

OTHER PUBLICATIONS

Masho et al., "Review of Tenofovir-Emtricitabine," Ther. Clin. Risk Manag. 3(6):1097-1104 (2007).
McColl et al., "Pooled Analysis of Recent Emtricitabine and Lamivudine Clinical Trials Reveals Differences in Rates of Development of the M184V/I Mutation," Poster No. PE7.3/17, 10th European AIDS Conference (EACS) Nov. 17-20, 2005, Dublin Ireland.
McIntee et al., "Probing the mechanism of action and decomposition of amino acid phosphomonoester amidates of antiviral nucleoside prodrugs," *J. Med. Chem.* 40(2):3323-31, 1997.
Memorandum of Law in Opposition of a Motion for Leave to File Amended Complaint Case No. 10-CV-01796 (Apr. 25, 2011).
Merck Index, 13th Edition, p. ONR-65 (2001).
Merck, Sharp & Dohme Corp and Bristol-Myers Squib Company Co's Opening Claim Construction Brief Case No. 10-CV-01851 (Dec. 2, 2011).
Merck, Sharp & Dohme Corp and Bristol-Myers Squib Company Co's Opening Claim Construction Brief Case No. 10-CV-01851 (Jan. 13, 2012).
Miller et al., Sixth International Congress on Drug Therapy in HIV Infection, Nov. 17-21, 2002 (1 page).
Miller M.D., et al., Human Immunodeficiency Virus Type 1 Expressing the Lamivudine-Associated M184V Mutation in Reverse Transcriptase Shows Increased Susceptibility to Adefovir and Decreased Replication Capability In Vitro, *The Journal of Infectious Diseases* 179:92-100 (1999) retrieved from http://jid.oxfordjournals.org/content/179/1/92.full.pdf on Jan. 30, 2014.
Miller, Margot N.A., et al., "Antiviral activity of tenofovir (PMPA) against nucleoside-resistant clinical HIV samples," Nucleosides Nucleotides Nucleic Acids,; 20:1025-1028 (2001).
Mills et al., "Artemis: Efficacy and Safety of Darunavir/ritonavir (DRV/r) 800/100mg Once-daily vs Lopinavir/ritonavir (LPV/r) in Treatment-naive, HIV-1-infected Patients at 96 wks," 48th Annual ICAAC/IDSA, 46th Annual Meeting, Washington, D.C. Oct. 25-28, 2008, Presentation No. H-1250c.
Minutes of Oral Proceedings from EPO for Application Application No. 067731595.0 dated Nov. 25, 2013.
Minutes of the Oral Proceedings before the Opposition Division for EP 1890681 B1 (Application No. 06773194.3) and Appendices (Apr. 5, 2011).
Molina et al., "A Lopinavir/Ritonavir-Based Once-Daily Regimen Results in Better Compliance and Is Non-inferior to a Twice-Daily Regimen Through 96 Weeks," AIDS Research and Human Retroviruses 23(12):1505-1514 (2007).
Molina et al., "Castle: Atazanavir-Ritonavir vs Lopinavir-Ritonavir in Antiretroviral-Naïve HIV-1 Infected Patients: 96 Week Efficacy & Safety," 48th Annual ICAAC/IDSA 46th Annual Meeting, Washington, D.C., Oct. 25-28, 2008, Presentation No. H-1250d.
Molina et al., "Once-Daily Combination Therapy with Emtricitabine, Didanosine, and Efavirenz in Human Immunodeficiency Virus-Infected Patients," J. Infect. Dis. 182:599-602 (2000).
Mulato et al., "Anti-HIV activity of adefovir (PMEA) and PMPA in combination with antiretroviral compounds: in vitro analyses," Antiviral Res. 36(2):91-97 (1997).
Murry et al., "Reversion of the M184V Mutation in Simian Immunodeficiency Virus Reverse Transcriptase is Selected by Tenofovir, Even in the Presence of Lamivudine," J. Virol. 77(2):1120-1130 (2003).
Naesens et al., "Antiretroviral activity and pharmacokinetics in mice of oral Bis(Pivaloyloxymethyl)-9-(2-phosphonylmethoxyethyl)adenine, the Bis(Pivaloyloxymethyl)ester prodrug of 9-(2-Phosphonylmethoxyethyl)adenine," Antimicro AG & Chemo. 40(1)22-28, 1996.
National Institutes of Health, "Guidelines for the Use of Antiretroviral Agents in HIV-1-Infected Adults and Adolescents," 9 pages (2011/2012).
Newman and Byrn, "Solid-state analysis of the active pharmaceutical ingredient in drug products" Drug Discovery Today, 8(19) 898-905 (2003).
Norton, Terry M. et al., Efficacy of Acyclovir Against Herpesvirus Infection in Quaker Parakeets, 52(12) Am. J. Vet. Res. Sep. 2007 (Dec. 1991).
Notari, "Prodrug Design," *Pharmaceutical Therapy*, 14:25-53, 1981.
Notice of Allegation and Detailed Statement in respect of Tenofovir Disoproxil Fumarate and Emtricitabine (Truvada®) and Canadian Patent Nos. 2,261,619 and 2,298,059, 56 pages (Nov. 22, 2011).
Notice of Allegation and Detailed Statement in respect of Truvada and Canadian Patent No. 2,512,475, 37 pages (Nov. 22, 2011).
Notice of Appeal of the Decision of the Opposition Division for EP Patent EP 1583542 B1 (Application No. 04701819.7) (Mar. 29, 2011).
Office Action for Korean Patent Application No. 7013069/2005 issued by the Korean Intellectual Property Office (Jan. 23, 2008).
Office Action for Korean Patent Application No. 7013069/2005 issued by the Korean Intellectual Property Office (May 22, 2007).
Office Action for Patent Application No. 10-2000-7000636 issued by the Korean Intellectual Property Office (Aug. 19, 2005) (translation).
Office Action for U.S. Appl. No. 08/900,752 issued by the United States Patent and Trademark Office (Apr. 16, 1998).
Office Action for Patent Application No. 11-510067 issued by the Japanese Patent Office (Dec. 11, 2007) (translation).
Office Action for Patent Application No. 2,261,619 issued by the Canadian Patent Office (Dec. 22, 2004).
Office Action for Patent Application No. 2,298,059 issued by the Canadian Intellectual Property Office (Apr. 25, 2007).
Office Action for Patent Application No. 2,512,475 issued by the Canadian Patent Office (Jan. 10, 2008).
Office Action for Patent Application No. 2,611,520 issued by the Canadian Patent Office (Jun. 7, 2010).
Office Action for Patent Application No. 2006-500939 issued by the Japanese Patent Office (Mar. 25, 2010).
Office Action for Patent Application No. 2006-500939 issued by the Japanese Patent Office (Nov. 9, 2009).
Office Action for Patent Application No. 200680026180.4 issued by the Chinese Patent Office (May 29, 2013) (translation).
Office Action for Patent Application No. 7007002/2008 issued by the Korean Intellectual Property Office (Jun. 11, 2008) (translation).
Office Action for Patent Application No. 7009376/2009 issued by the Korean Intellectual Property Office (Oct. 9, 2009) (translation).
Office Action for Patent Application No. 87112168 issued by the Taiwanese Intellectual Property Office (Mar. 1, 2004) (translation).
Office Action for Patent Application No. 87112168 issued by the Taiwanese Intellectual Property Office (May 6, 2002) (translation).
Office Action for Patent Application No. 87112168 issued by the Taiwanese Intellectual Property Office (Oct. 20, 2000) (translation).
Office Action for Patent Application No. 93112403 issued by the Taiwanese Intellectual Property Office (Apr. 27, 2005) (translation).
Office Action, 10 pages, from U.S. Appl. No. 12/195,161 (mailed May 7, 2010).
Office Action, 10 pages, from U.S. Appl. No. 12/204,174 (mailed Oct. 1, 2009).
Office Action, 7 pages, from U.S. Appl. No. 10/540,794 (mailed Sep. 21, 2006).
Office Action, 8 pages, from U.S. Appl. No. 10/540,794 (mailed Oct. 31, 2007).
Office Action, 8 pages, from U.S. Appl. No. 12/204,174 (mailed Jun. 4, 2010).
Office Action, 9 pages, from U.S. Appl. No. 10/540,794 (mailed May 16, 2007).
Official Action and Preliminary Notice of Allowance from the Eurasian Patent Office for Application No. 200501134/28 (May 14, 2010).
Official Action for Application No. 095120445 issued by the Taiwanese Intellectual Property Office (Nov. 29, 2011) (translation), 6 pages.
Official Action for Application No. 2008-517083 issued by the Japanese Patent Office (Aug. 2, 2011) (translation), 17 pages.
Official Action for Application No. 2008-517083 issued by the Japanese Patent Office (Mar. 23, 2012) (translation).

(56) References Cited

OTHER PUBLICATIONS

Official Action for Ex Parte Reexamination of U.S. Pat. No. 5,922,695 (Dec. 11, 2007).
Official Action for Ex Parte Reexamination of U.S. Pat. No. 5,935,946 (Jan. 16, 2008).
Official Action for Ex Parte Reexamination of U.S. Pat. No. 5,977,089 (Jan. 16, 2008).
Official Action for Ex Parte Reexamination of U.S. Pat. No. 6,043,230 (Dec. 11, 2007).
Official Action for Patent Application No. 10-1999-7000806 issued by the Korean Intellectual Property Office (Apr. 28, 2005) (translation).
Official Action for Patent Application No. 10-508318 issued by the Japanese Patent Office (Apr. 10, 2007) (translation).
Official Action for Patent Application No. 200501134/28 issued by the Eurasian Patent Office (Dec. 25, 2008).
Official Action for Patent Application No. 200501134/28 issued by the Eurasian Patent Office (Oct. 15, 2006).
Official Action for Patent Application No. 333687 issued by the Intellectual Property Office of New Zealand (Mar. 2, 1999).
Official Action for Patent Application No. 7001077/2008 issued by the Korean Intellectual Property Office (Sep. 13, 2010).
Official Action for Patent Application No. 93100813 issued by the Taiwanese Intellectual Property Office (Jun. 22, 2005) (translation).
Official Action for Patent Application No. 93100813 issued by the Taiwanese Intellectual Property Office (Mar. 16, 2011) (translation).
Official Action for Patent Application No. 200800033/27 issued by the Eurasian Patent Office (2010) (translation).
Official Action for Patent Application No. 200800033/27 issued by the Eurasian Patent Office, dated May 17, 2011, 3 pages (including Agent's Summary).
Official Action (Allowance) for Patent Application No. 200800033/27 issued by the Eurasian Patent Office, dated Nov. 22, 2011, 6 pages (including Agent's comments and allowed claims), 6 pages.
Official Action, 2 pages, from JP appl. No. 2010-175808 (mailed Nov. 6, 2012) translation attached.
Official Communication for Patent Application No. 2100/DEL/2007 issued by the Indian Patent Office (Jan. 16, 2013).
Opinion on Patent Application No. 1-2005-00812 issued by the Vietnamese Patent Office (Jul. 27, 2008).
Opponents Comments to the Reply Statement by the Applicant relating to Patent Application No. 3383/DELNP/2005 (Aug. 14, 2008).
Opposition filed in Indian Patent Appl. No. 9661/DELNP/2007 by Cipla Limited (Jun. 30, 2009).
Order Granting Request for Ex Parte Reexamination of U.S. Pat. No. 5,922,695 (Jul. 13, 2007).
Order Granting Request for Ex Parte Reexamination of U.S. Pat. No. 5,935,946 (Jul. 13, 2007).
Order Granting Request for Ex Parte Reexamination of U.S. Pat. No. 5,977,089 (Jul. 13, 2007).
Order Granting Request for Ex Parte Reexamination of U.S. Pat. No. 6,043,230 (Jul. 13, 2007).
Order signed by Judge Richard J. Sullivan Case No. 10-CV-01796 (Apr. 26, 2012).
Order signed by Judge Richard J. Sullivan Case No. 10-CV-01796 (Dec. 5, 2011).
Order signed by Judge Richard J. Sullivan Case No. 10-CV-01796 (Jan. 17, 2013).
Order signed by Judge Richard J. Sullivan Case No. 10-CV-01796 (Jan. 18, 2013).
Order signed by Judge Richard J. Sullivan Case No. 10-CV-01796 (Jan. 30, 2013).
Order signed by Judge Richard J. Sullivan Case No. 10-CV-01798 (May 26, 2010).
Order signed by Judge Richard J. Sullivan Case No. 08-CV-10838 (Dec. 19, 2011).
Order signed by Judge Richard J. Sullivan Case No. 08-CV-10838 (May 26, 2010).
Order signed by Judge Richard J. Sullivan Case No. 10-CV-01851 (Jul. 19, 2013).
Order signed by Judge Richard J. Sullivan Case No. 10-CV-01851 (Jun. 5, 2013).
Order signed by Judge Richard J. Sullivan Case No. 10-CV-01851 (May 14, 2013).
Order signed by Judge Richard J. Sullivan Case No. 10-CV-01851 (May 24, 2013).
Osborne, "Gilead plans $300M notes sale to recoup some merger costs. (Gilead Sciences Inc.)," Bioworld Today, 13(239), 1 page (Dec. 16, 2002).
Osborne, "Gilead, Triangle Plan Merger: $464 Deal Pairs HIV Drugs," Bioworld Today 13(233):1,6 (2002).
Osol et al., Editor, Remington's Pharmaceutical Sciences, Sixteenth Edition, pp. 1554-1557, 1980.
Pallella et al., J. Med. Chem. 338:853-860 (1998).
Parikh, Handbook of Pharmaceutical Granulation Tech., NY, Marcel Dekker Inc., 1996.
Patent Examination Report No. 1, Australia patent appl. No. 2011253996, 2 pages (Nov. 15, 2012).
Pharmaceutical Dosage Forms and Drug Delivery Systems, 6th Ed. pp. 171-174 (1995).
Pharmaceutical Dosage Forms. Tablets. $2^{nd}$ Ed., revised and expanded, Lieberman et al., eds., pp. 93 and 98 (1990).
Pharmaceutical Technology (2005), Big Pharma Companies Team Up to Develop Once-Daily Triple-Combination HIV Drug,vol. 29, No. 4.
Piantadosi et al., "Synthesis and Evaluation of Novel Ether Lipd Nucleoside Conjugates for Anti-HIV-1 Activity," J. Med. Chem. 34:1408-1414 (1991).
Plaintiff's Opening Claim Construction Brief filed by Gilead Sciences, Inc. Case No. 10-CV-01796 (Dec. 2, 2011).
Plaintiff's Opposition to Defendants' Pretrial Memorandum by Gilead Sciences, Inc. Case No. 10-CV-01796 (Jan. 28, 2013).
Plaintiff's Pretrial Memorandum filed by Gilead Sciences, Inc. Case No. 10-CV-01796 (Jan. 14, 2013).
Plaintiff's Proposed Findings of Fact and Conclusions of Law filed by Gilead Sciences, Inc. Case No. 10-CV-01796 (Jan. 14, 2013).
Plaintiffs' Opening Claim Construction Brief filed by Gilead Sciences, Inc., Emory University Case No. 08-CV-10838 (Nov. 4, 2011).
Plaintiffs' Opening Pretrial Brief filed by Merck, Sharp & Dohme Corp and Bristol-Myers Squib Company Co. Case No. 10-CV-01851 (May 10, 2013).
Plaintiffs' Proposed Findings of Fact and Conclusions of Law filed by Merck, Sharp & Dohme Corp and Bristol-Myers Squib Company Co. Case No. 10-CV-01851 (May 10, 2013).
Plaintiffs' Rebuttal Claim Construction Brief filed by Gilead Sciences, Inc., Emory University Case No. 08-CV-10838 (Dec. 16, 2011).
Plaintiffs' Rebuttal Claim Construction Brief filed by Gilead Sciences, Inc., Emory University Case No. 10-CV-01796 (Jan. 13, 2012).
Plaintiffs' Reply to Teva USA's Counterclaim filed by Gilead Sciences, Inc., Emory University Case No. 09-CV-04463 (Aug. 31, 2009).
Plaintiff's Reply to Teva USA's Amended Counterclaim, filed by Gilead Sciences, Emory University, Case No. 08-CV-10838 (Aug. 10, 2009).
Plaintiff's Reply to Teva USA's Second Amended Counterclaim, filed by Gilead Sciences, Emory University,Case No. 08-CV-10838 (Oct. 15, 2009).
Plaintiff's Reply to Teva's Counterclaim, filed by Gilead Sciences, Inc., Emory University Case No. 08-CV-10838 (Feb. 25, 2009).
Plaintiffs' Response to Defendants' Pretrial Memorandum filed by Merck, Sharp & Dohme Corp and Bristol-Myers Squib Company Co. Case No. 10-CV-01851 (May 24, 2013).
Pozniak et al., "Tenofovir Disoproxil Fumarate, Emtricitabine, and Efavirenz Versus Fixed-Dose Zidovudine/Lamivudine and Efavirenz in Antiretroviral-Naive Patients," JAIDS 43(5):535-540 (2006).
Pre-Grant Opposition Petition against Brazilian Patent Application PI 0406760-6 (Aug. 20, 2010).

(56) References Cited

OTHER PUBLICATIONS

Project Inform, "Perspective," pp. 1-28 (2003).
Puech et al., "Intracellular delivery of nucleoside monophosphates through a reductase-mediated activation process," Antiviral Res. 22:155-174 (1993).
Pujari et al., "Safety and long term effectiveness of generic fixed-dose formulations of nevirpine-based HAART amongst antiretroviral-naïve HIV-infected patients in India," World Health Organization, [on line], Dec. 16, 2003, pp. 99-116; (Retrieved from: http://libdoc.who.int/publications/2003/a86263.pdf.
Quan et al., "Endogenous Reverse Transcriptase Assays Reveal Synergy between Combinations of the M184V and other Drug-Resistance-conferring Mutations in Interactions with Nucleoside Analog Triphosphates," J. Mol. Biol. 277:237-247 (1998).
Rejection Decision for Patent Application No. 200480002190.5 issued by the Patent Office of the People's Republic of China (Jan. 15, 2010).
Rejection of Patent Application No. 93100813 issued by the Taiwanese Intellectual Property Office (Feb. 22, 2006) (translation).
Reply of the Patent Proprietor to the Notice of Opposition of EP 1890681 B1 (Application No. 06773194.3) (Jun. 22, 2010).
Reply of the Patent Proprietor to the Notices of Opposition of EP Patent EP 1583542 B1 (Application No. 04701819.7) (Jan. 4, 2010).
Reply to the statement of appeal grounds, EP 1583542 B1 (Application No. 04701819.7), 50 pages (Oct. 18, 2011).
Request for Correction of EP Appln No. 04701819.7 (Jul. 8, 2008).
Request for Correction of EP Appln No. 04701819.7 (Jun. 27, 2008).
Request for Ex Parte Reexamination of U.S. Pat. No. 5,922,695 (submitted Apr. 30, 2007).
Request for Ex Parte Reexamination of U.S. Pat. No. 5,935,946 (submitted Apr. 30, 2007).
Request for Ex Parte Reexamination of U.S. Pat. No. 5,977,089 (submitted Apr. 30, 2007).
Request for Ex Parte Reexamination of U.S. Pat. No. 6,043,230 (submitted Apr. 30, 2007).
Request for Leave to Submit Supplemental Expert Witness Affidavit of Jerry L. Atwood, Ph.D. on behalf of Plaintiffs filed by Merck, Sharp & Dohme Corp and Bristol-Myers Squib Company Co. Case No. 10-CV-01851 (May 24, 2013).
Response to Summons and Annex rom EPO for Application No. 067731595.0 dated Sep. 25, 2013.
Response to the Noting of Loss of Rights pursuant to Rule 112(1) EPC dated Sep. 3, 2012, Patent Publication EP 2386294 (Application No. 11167101.2) (Nov. 13, 2012).
Response to the noting of loss of rights pursuant to Rule 112(1)EPC dated Nov. 14, 2012, Patent Publication EP 1923063 (Application No. 08152527.1) (Jan. 24, 2013).
Response to the reply letter of Teva Pharmaceutical Industries Ltd. dated Oct. 18, 2011, EP 1583542 B1 (Application No. 04701819.7), 35 pages (Aug. 9, 2012).
Response to the Written Opinion of the ISA (May 10, 2007) PCT/US2006/023222.
Response to the Written Opinion of the ISA (May 10, 2007) PCT/US2006023223.
Reversal of Rejection Decision for Application No. 200480002190.5 by the Patent Rexamination Board (Patent Office of the People's Republic of China) (Jun. 10, 2010).
Revised International Search Report for PCT/US2004/000832 (Aug. 5, 2004).
Revocation of European Patent EP 1890681 B1 (Application No. 06773194.3) (Jun. 8, 2011).
Riaz and Ami, "Stability of Aminophylline," Pak. J. Pharm. Sci. 6(1):35-44 (1993).
Richman, "Antiretroviral activity of emtricitabine, a potent nucleoside reverse transcriptase inhibitor," Antivir. Ther. 6(2):83-88 (2001).
Richman, "HIV Chemotherapy," Nature 410:995-1001 (2001).
Ristig et al., "Tenofovir Disoproxil Fumarate Therapy for Chronic Hepatitis B in Human Immunodeficiency Virus/Hepatitis B Virus—Coinfected Individuals for Whom Interferon-α and Lamivudine Therapy Have Failed," J. Infect. Dis.186:1844-1847 (2002).
Robinson B.S., et al. BMS-232632, a Highly Potent Human Immunodeficiency Virus Protease Inhibitor That Can Be Used in Combination with Other Available Antiretroviral Agents.—Antimicrobial Agents and Chemotherapy, vol. 44, No. 8, Aug. 2000, pp. 2093-2099, retrieved from http://www.ncbi.nlm.nih.gov/pmc/articles/PMC90019/pdf/acQ02093.pdf on Jan. 30, 2014.
Robinson et al., "Discovery of the Hemifumarate and (alpha-L-Alanyloxy)methylester as prodrugs of an antirheumatic oxindole: Prodrugs for enolic OH group," J. Med. Chem. 39:10-18, 1996.
Rousseau et al., "Prototype trial design for rapid dose selection of antiretroviral drugs: an example using emtricitabine (Coviracil)," Journal of Antimicrobial Chemotherapy 48:507-513 (2001).
Safadi et al., "Phosphoryloxymethyl carbamates and carbonates—Novel water soluble prodrugs for amines and hindered alcohols," Pharm. Res. 10(9):1350-1355, 1993.
Sakamoto et al., "Studies on prodrugs II. Preparation and characterization of (5-substituted 2-oxo-1, 3-dioxolen-4-yl)methyl esters of Ampicillin," Chem. Pharm. Bull. 32(6):2241-2248, 1983.
Samara et al., "Pharmacokinetic analysis of Diethylcarbonate prodrugs of Ibuprofen and Naproxen," Biopharmaceutics & Drug Disposition 16:201-210, 1995.
Sanne et al., "Genotypic Analysis of HIV-1 Infected ART-Naive Patients Receiving Emtricitabine (FTC) or Lamivudine (3TC) in a Double Blind Equivalence Trial," Poster No. 4433, presented at the XIV International AIDS Conference Jul. 7-12, 2002, Barcelona, Spain.
Sanne et al., "Two Randomized, Controlled, Equivalence Trials of Emtricitabine (FTC) to Lamivudine (3TC)," Poster 4432 presented at the XIV International AIDS Conference, Jul. 7-12, 2002, Barcelona, Spain.
Schinazi et al., "Characterization of Human Immunodeficiency Viruses Resistant to Oxathiolane-Cytosine Nucleosides," Antimicrobial Agents and Chemotherapy 374:875-881 (1993).
Schinazi et al., "Selective Inhibition of Human Immunodeficiency Viruses by Racemates and Enantiomers of cis-5-Fluoro-1-[2-(Hydroxymethyl)-1,3-Oxathiolan-5-yl]Cytosine," Antimricobial Agents and Chemotherapy 36(11):2423-2431(1992).
Schinazi et al., Letter to the Editor "Assessment of the Relative Potency of Emtricitabine and Lamivudine," J. AIDS 34(2)243-245 (2003).
Scrip, "Gilead Acquires Triangle for $464 Million," 2 pages (Dec. 6, 2002).
Search and Examination Report for Appln No. AP/P/2005/003348 issued by the African Regional Intellectual Property Organization, 5 pages (Apr. 10, 2008).
Second Amended Complaint for Patent Infringement against Teva Pharmaceuticals USA, Inc. and Teva Pharmaceuticals Industries, Ltd. filed by Gilead Sciences, Inc., Emory Univesity Case No. 08-CV-10838 (Sep. 25, 2009).
Second Amended Answer and Counterclaim against Gilead Sciences, Inc. filed by Teva Pharmaceuticals USA, Inc and Teva Pharmaceuticals Industries, Ltd. Case No. 08-CV-10838 (Filed Oct. 9, 2009).
Second Office Action for Application No. 200680026180.4 issued by the State Intellectual Property Office of the People's Republic of China (Oct. 20, 2011) (translation).
Second Office Action for Patent Application No. 200480002190.5 issued by the Patent Office of the People's Republic of China (May 11, 2011).
Second Office Action for Patent Application No. 200510099916.8 issued by the Chinese Patent Office (Nov. 16, 2007) (translation).
Second Office Action for Patent Application No. 97197460.8 issued by the Chinese Patent Office (Aug. 5, 2005) (translation).
Second Official Action for Patent Application No. a 2005 07947 issued by the Ukrainian Patent Office (2006) (translation).
Serafinowska et al., "Synthesis and in vivo Evaluation of prodrug of 9-{2-(Phosphonomethoxy) ethoxy} adenine," J. Med. Chem. 38:1372-1379, 1995.
Shaw et al., "Metabolism and pharmacokinetics of novel oral prodrugs of 9[(R)-2-(phosphonomethoxy)propyl]adenine (PMPA) in dogs," Pharm. Res. 14(12):1824-1829, 1997.

(56) References Cited

OTHER PUBLICATIONS

Siddiqui et al., "Design and Synthesis of Lipophilic Phosphoramidate D4T-MP Prodrugs Expressing High Potency Against HIV in Cell Culture: Structural Determinants for In Vitro Activity and QSAR," J. Med. Chem. 42(20):4122-4128 (1999).
Smirnov et al., "A Comparative Study of the Kinetics of Cytarabine Hydrolytic Deamination in Aqueous Solutions," Pharm. Chem. J. 34(8):451-454 (2000).
Smith et al., "Randomized, double-blind, placebo-matched, multicenter trial of abavacir/lamivudine or tenofovir/emtricitabine with lopinavir/ritonavir for inital HIV treatment," AIDS 23:1547-1556 (2009).
Srinivas R.V. et al., "Antiviral Activities of 9-R-2-Phosphonomethoxypropyl Adenine (PMPA) and Bis(isopropyloxymethylcarbonyl)PMPA against Various Drug-Resistant Human Immunodeficiency Virus Strains," *Antimicrob. Agents Chemother.* Jun. 1998, vol. 42, No. 6, pp. 1484-1487 retrieved from at:http://aac.asm.org/content/42/6/1484.full.pdf+html on Jan. 30, 2014.
Srinivas et al., "Metabolism and in vitro antiretroviral activities of Bis(Pivaloyloxymethyl) prodrugs of acyclic nucleoside phosphonates," Antimicro AG & Chemo. 37(10):2247-2250, 1993.
Srivastva et al., "Bioreversible phosphate protective groups: Synthesis and stability of model acyloxymethyl phosphates," Bioorg. Chem. 12:118-129, 1984.
Starrett et al., "Synthesis and in vitro evaluation of a phosphonate prodrug:bis(pivaloyloxymethyl) 9-(2-phophonylmethoxyethyl)adenine," Antiviral Res. 19:267-273, 1992.
Starrett et al., "Synthesis, oral bioavailability determination, and in vitro evaluation of prodrugs of the Antiviral agent 9-[2-(phosphonomethoxy)ethyl]adenine (PMEA)," J. Med. Chem. 37:1857-1864, 1994.
Staszewski et al., NEJM, 1999, 341 5,1865-1873.
Staszewski S., et al., "Efficacy and safety of tenofovir disoproxil fumarate (TDF) versus stavudine (d4T) when used in combination with lamivudine (3TC) and efavirenz (EFV) in HIV-1 infected patients naive to antiretroviral therapy (ART): 48-week interim results," XIV International AIDS Conference, Barcelona, Spain, Jul. 7-12, 2002, Abstracts, No. 9804; retrieved from http://www.iasocietv.org/Default.aspx?page1d=12&abstract1d=9804 on Jan. 30, 2014.
Stella, Valentino J. et al., Prodrugs and Site-Specific Drug Delively, 23 Journal of Medicinal Chemistty 1275 (1980).
Stipulation and Agreement Regarding U.S. Pat. No. 5,922,965, U.S. Pat. No. 5,935,946, U.S. Pat. No. 5,977,089, and U.S. Pat. No. 6,043,230 Case No. 10-CV-01796 (Oct. 9, 2012).
Substantive Examination Report for Patent Application No. W00 2005 02145 from the Indonesian Patent Office (2010).
Sueoka et al., "Pharmacokinetics of Alkoxycarbonyloxy ester prodrugs of PMPA in dogs," Abstract, American Association of Pharmaceutical Science, Western Regional Meeting, Apr. 24-25, 1997.
Summons to Attend Oral Proceedings and Annex to the Communication for EP Patent EP1583542B1 (Application No. 04701819.7) (May 21, 2010).
Summons to Attend Oral Proceedings and Annex to the Communication for the Opposition of EP 1890681 B1 (Application No. 06773194.3) (Oct. 14, 2010).
Summons to attend Oral Proceedings EPO for Application No. 067731595.0 dated Jul. 9, 2013.
Tamari, "A Decade in HIV Treatment: What Is the State of the Art and How Did We Arrive," Clinical Excellence for Nurse Practitioners 5(1):4-12 (2001).
Teva Pharmaceutical Industries Ltd., Notice of Opposition of EP Patent EP1583542B1 (Application No. 04701819.7) (Mar. 13, 2009).
Teva Pharmaceutical Industries Ltd., Written Submission in preparation for Oral Proceedings for EP Patent EP1583542B1 (Application No. 04701819.7) (Sep. 16, 2010).
Teva Pharmaceutical Industries, Ltd, (Opponent), Opposition Brief against Israel Patent No. 169243 (dated Jul. 26, 2009).
Teva Pharmaceuticals Industries Ltd., Notice of Opposition of EP 1890681B1 (Application No. 06773194.3) (Oct. 7, 2009).
Teva Pharmaceuticals Industries Ltd., Written Submission in preparation for Oral Proceedings for the Opposition of EP 1890681B1 (Application No. 06773194.3) (Mar. 17, 2011).
Teva Pharmaceuticals USA, Inc and Teva Pharmaceuticals Industries, Ltd.'s Opening Claim Construction Brief Case No. 10-CV-01851 (Dec. 2, 2011).
Teva Pharmaceuticals USA, Inc and Teva Pharmaceuticals Industries, Ltd.'s Rebuttal Claim Construction Brief Case No. 10-CV-01851 (Jan. 13, 2012).
Teva's Opening Claim Construction Brief filed by Teva Pharmaceuticals USA, Inc and Teva Pharmaceuticals Industries, Ltd. Case No. 08-CV-10838 (Nov. 4, 2011).
Teva's Opening Claim Construction Brief filed by Teva Pharmaceuticals USA, Inc and Teva Pharmaceuticals Industries, Ltd. Case No. 10-CV-01796 (Dec. 2, 2011).
Teva's Rebuttal Claim Construction Brief filed by Teva Pharmaceuticals USA, Inc and Teva Pharmaceuticals Industries, Ltd. Case No. 10-CV-01796 (Jan. 13, 2012).
Teva's Rebuttal Claim Construction Brief filed by Teva Pharmaceuticals USA, Inc and Teva Pharmaceuticals Industries, Ltd. Case No. 08-CV-10838 (Dec. 16, 2011).
Teva's Response to Patentee's Appeal, 5 pages, EP Pat. No. 1890681, EP Appl. No. 06773194.3 (mailed May 3, 2012).
Theory and Practice of Industrial Pharmacy, 3rd Edition, Lachman et al., Eds., Lea & Febiger, pp. 324-329 (1986).
Third Amended Answer filed by Teva Pharmaceuticals USA, Inc and Teva Pharmaceuticals Industries, Ltd. Case No. 08-CV-10838 (Filed Aug. 6, 2010).
Third Amended Complaint for Patent Infringement against Teva Pharmaceuticals USA, Inc and Teva Pharmaceuticals Industries, Ltd. filed by Gilead Sciences, Inc., Emory University Case No. 08-CV-10838 (Jul. 6, 2010).
Third Office Action for Patent Application No. 97197460.8 issued by the Chinese Patent Office (Jun. 9, 2006) (translation).
Third Official Action for Patent Application No. a 2005 07947 issued by the Ukrainian Patent Office (2007) (translation).
Thoithi et al., "Investigation of the Kinetics of Degradation of Hexopyranosylated Cytosine Nucleosides Using Liquid Chromatography," Nucleosides, Nucleotides & Nucleic Acids 19(1 &2):189-203 (2000).
Thornber "Isosterism and Molecular Modification in Drug Design" Chem. Soc. Reviews 18: 563-580, 1979.
Tisdale et al., "Rapid in vitro selection of human immunodeficiency virus type 1 resistant to 3'-thiacytidine inhibitors due to a mutation in the YMDD region of reverse transcriptase," Proc. Natl. Acad. Sci. USA 90:5653-5656 (1993).
Transcript of Proceedings held on Apr. 26, 2012 Case No. 10-CV-01796.
Transcript of Proceedings held on Oct. 3, 3012, 2012 Case No. 10-CV-01796.
Truvada Patient Information Leaflet, 33 pages (2008).
Tsai et al., "Effects of (R)-9-(2-phophonylmethoxypropyl)adenine monotherapy on chronic SIV infection in macaques," Aids Res. & Hum. Retro. 13(8):707-712, 1997.
Tsai et al., "Prevention of SIV infection in macaques by (R)-9-(2-phosphonylmethoxypropyl)adenine," Science 270:1197-1199, 1995.
U.S. Department of Health and Human Services (2004) "Guidance for Industry Fixed Dose Combination and Co-Packaged Drug Products for Treatment of HIV—Draft Guidance" pp. 1-21.
Ueda et al., "Vinyl compounds of nucleic acid bases I. Synthesis of N-vinyluracil, N-vinylthymine, and N-vinyladenine," Die Makromolekulare Chemie 120:13-20, 1968.
USP 24 The United States Pharmacopeia (2000).
Van Rompay et al., "9-[2-(Phosphonomethoxy)propyl]adenine therapy of established simian immunodeficiency virus infection in infant rhesus macaques," *Antimicrob. Agents Chemother.* 40:2586-2591, (1996) retrieved from http://www.ncbi.nlm.nih.gov/pmc/articles/PMC163581/pdf/402586.pdf on Jan. 31, 2014.

(56) References Cited

OTHER PUBLICATIONS

Van Rompay, K. K., et al., "Virulence and reduced fitness of simian immunodeficiency virus with the M184V mutation in reverse transcriptase," J. Virology, 76(12):6083-6092 (2002) http://www.ncbi.nlm.nih.gov/pmc/articles/PMC136201/pdf/0196.pdf retrieved on Jan. 30, 2014.
Viread (Tenofovir Disoproxil Fumarate Tablets) Summary of Product Characteristics, EMEA, SmPC, 37 pages (Feb, 5, 2002).
Viread Label pp. 1-44 (2001).
Viread Patient Information Leaflet, 21 pages (2002).
Virji-Jeganathan, "BVV Stock Table Highlights," Bioventure View, 17(25): pp. 6-7 (Dec. 10, 2002).
Wainberg et al. "In vitro selection and characterization of HIV-1 with reduced susceptability to PMPA," Antiviral Therapy 4:87-94 (1999).
Walmsley et al., "Gemini: A Noninferiority Study of Saquinavir/Ritonavir Versus Lopinavir/Ritonavir as Initial HIV-1 Therapy in Adults," J. Acquir. Immune Defic. Syndr. 50(4):367-374 (2009).
Wang "FTC: A Potent and Selective Anti-HIV and Anti-HBV Agent Demonstrating Desirable Pharmacokinetic (PK Characteristics," Abstracts of the IDSA, 36th Annual Meeting, Session 58, Poster 415, Hepatits A, B, and C in HIV-Infected Persons Friday, 4-6 pm (1998).
Wang et al. "Lack of Significant Pharmacokinetic Interactions between Emtricitabine and Other Nucleoside Antivirals in Healthy Volunteers," $41^{st}$ ICAAC Abstracts, Chicago, IL, Sep. 22-25, 2001, Abstract A-505.
Wang et al. "Pharmacokinetic and pharmacodynamic characteristics of emtrictabine support its once daily dosing," Int. Conf. AIDS, Jul. 7-12 14:abstract TUPeB4546 (2002).
Weller et al., "Orally active Fibrinogen receptor antagonists. 2. Amidoximes as prodrugs of amidines," J. Med. Chem. 39:3139-3147, 1995.
Wirth et al., "Maillard Reaction of Lactose and Fluoxetine Hydrochloride, a Secondary Amine," J. Pharm. Sci. 87(1):31-39 (1998).
Written Opinion issued by the ISA for PCT/US2006/023223 (Feb. 23, 2007).
Written Opinion of the ISA for PCT/US2006/023222 (Feb. 23, 2007).
Yeni et al., "Antiretroviral Treatment for Adult HIV Infection in 2002," JAMA 288(2):222-235 (2002).
Yuan et al., "Degradation Kinetics of Oxycarbonyloxymethyl Prodrugs of Phosphonates in Solution," Pharm. Res. 18(2):234-237 (2001).
Zalac et al., "Paracetamol-Propyphenazone Interaction and Formulation Difficulties Associated with Eutectic Formation in Combination Solid Dosage Forms," Chem. Pharm. Bull. 47(3):302-307 (1999).
Zao, Biokad Objection against the application of Eurasian Patent No. 015145 in the Russian Federation dated Jul. 10, 2013.
Zhang et al. "Phase transformation considerations during process development and manufacture of solid oral dosage forms" Adv Drug Del Reviews 56(30), 371-390 (2004).
"Annex I. Summary of Product Characteristics," for Epivir, 9 pages (1997).
"Annex I. Summary of Product Characteristics," for Truvada film-coated tablets, 14 pages.
Castello and Mattocks, "Discoloration of Tablets Containing Amines and Lactose," J. Pharm. Sci. 106-108 (1962).
Excerpts from the Reexamination of U.S. Pat. No. 6,043,230, 6 pages.
Gerhartz (editor) Ullmann's Encyclopedia of Industrial Chemistry vol. B2, Unit Operations I, $5^{th}$ Edition, p. 3-7 (1988).
Complaint for Patent Infringement. Document filed by Emory University, Gilead Sciences, Inc, Case No. 1:12-cv-06293-RJS (Filed: Aug. 16, 2012), 14 pages.
Lupins Limited'S Answer, Separate Defenses, and Counterclaims to Plaintiffs' Complaint. Document filed by Lupin Limited, Case No. 1:12-cv-06293-RJS (Filed Oct. 22, 2012), 21 pages.
Plaintiffs' Reply to Defendant's Counterclaims. Document filed by Emory University, Gilead Sciences, Inc., Case No. 1:12-cv-06293-RJS (Filed: Nov. 9, 2012), 10 pages.
Letter to Judge Richard J. Sullivan from Peter J. Curtin dated Sep. 3, 2013 Case No. 1:12-cv-06293-RJS (Filed: Sep. 4, 2013), 1 page.
Stipulation and Agreement Regarding U.S. Pat. No. 6,703,396, U.S. Pat. No. 6,642,245, U.S. Pat. No. 5,814,639 and U.S. Pat. No. 5,914,331: Case No. 1:12-cv-06293-RJS (Dated: Sep. 3, 2013), 6 pages.
Letter to Judge Richard J. Sullivan from David B. Bassett dated Sep. 16, 2014 re: Settlement. Document filed by Emory University, Gilead Sciences, Inc., Case No. 1:12-cv-06293-RJS (Filed: Sep. 16, 2014), 1 page.
Exhibit A to Letter addressed to Judge Richard J. Sullivan from David B. Bassett dated Sep. 16, 2014 re: Settlement. Document filed by Emory University, Gilead Sciences, Inc., Case No. 1:12-cv-06293-RJS (Filed: Sep. 16, 2014).
Order on Stipulation for Dismissal of Plaintiffs, Gilead Sciences, Inc. ("Gilead") and Emory University ("Emory"), and Defendant, Lupin Limited ("Lupin"), Case No. 1:12-cv-06293-RJS (Dated: Sep. 17, 2014), 2 pages.
Complaint for Patent Infringment. Document filed by Gilead Sciences, Inc., Case No. 1:12-cv-07910-RJS (Filed: Oct. 24, 2012),19 pages.
Lupins Limited's Answer, Separate Defenses, and Counterclaims to Plaintiff's Complaint. Document filed by Lupin Limited, Case No. 1:12-cv-07910-RJS (Filed: Dec. 20, 2012), 23 pages.
Plaintiff's Reply to Defendant's Counterclaims. Document filed by Gilead Sciences, Inc., Case No. 1:12-cv-07910-RJS (Filed: Jan. 9, 2013), 9 pages.
Order Case No. 1:12-cv-07910-RJS (Dated: Jul. 23, 2013), 1 page.
Complaint for Patent Infringment. Document filed by Gilead Sciences, Inc. Case No. 2:14-cv-00796-JRG-RSP (Filed: Jul. 24, 2014), 14 pages.
Joint Motion for Order on Stipulation for Dismissal. Case No. 2:14-cv-00796-JRG-RSP (Filed: Sep. 16, 2014), 3 pages.
Attachment 1 to Stipulation of Dismissal by Gilead Sciences, Inc., Lupin Ltd., Case No. 2:14-cv-00796-JRG-RSP (Filed: Sep. 16, 2014), 1 page.
Order on Stipulation for Dismissal. Signed by Magistrate Judge Roy S. Payne on Sep. 23, 2014. (nkl, ) Case No. 2:14-cv-00796-JRG-RSP (Dated: Sep. 23, 2014).
Complaint for Patent Infringment. Document filed by Gilead Sciences, Inc. Case No. 1:12-cv-06351-RJS. (Filed:Aug. 20, 2012), 23 pages.
First Amended Complaint for Patent Infringment. Document filed by Gilead Sciences, Inc., Case No. 1:12-cv-06351-RJS (Filed: Sep. 11, 2012), 47 pages.
Cipla Limited's Answer and Separate Defenses to Plaintiff's First Amended Complaint. Document filed by Cipla Limited, Case No. 1:12-cv-06351-RJS) (Filed: Dec. 10, 2012), 30 pages.
Second Amended Complaint for Patent Infringement. Document filed by Gilead Sciences, Inc., Case No. 1:12-cv-06351-RJS (Filed: Oct. 17, 2013), 24 pages.
Defendant Cipla's Unneccesary Opening Claim Construction Brief. Document filed by Cipla Limited, Case No. 1:12-cv-06351-RJS) (Filed: Oct. 25, 2013), 25 pages.
Declaration of Aaron M. Johnson in Support of Defendant Cipla's Opening Claim Construction Brief. Case No. 1:12-cv-06351-RJS (Filed: Oct. 25, 2013), 3 pages.
Exhibit 8 to Declaration of Aaron M. Johnson in Support re: 46 Claim Construction Statement. Document filed by CIPLA Limited, Case No. 1:12-cv-06351-RJS (Filed: Oct. 25, 2013), 20 pages.
Exhibit 10 to Declaration of Aaron M. Johnson in Support re: 46 Claim Construction Statement. Document filed by CIPLA Limited, Case No. 1:12-cv-06351-RJS (Filed: Oct. 25, 2013), 3 pages.
"Prophylaxis" Stedman's Medical Dictionary (1995), 26th Edition (1995) 3 pages.
Plaintiff's Opening Claim Construction Brief. Document filed by Gilead Sciences, Inc., Case No. 1:12-cv-06351-RJS, (Filed: Oct. 25, 2013), 18 pages.
Declaration of Jason Johnson. Document filed by Gilead Sciences, Inc., Case No. 1:12-cv-06351-RJS (Filed: Oct. 25, 2013), 3 pages.

(56) References Cited

OTHER PUBLICATIONS

Exhibit A to Declaration of Jason Johnson in Support of Plaintiff's Opening Claim Construction Brief. Document filed by Gilead Sciences, Inc., Case No. 1:12-cv-06351-RJS (Filed: Oct. 25, 2013), 25 pages.
Exhibit B to Declaration of Jason Johnson in Support of Plaintiff's Opening Claim Construction Brief. Document filed by Gilead Sciences, Inc., Case No. 1:12-cv-06351-RJS (Filed: Oct. 25, 2013), 9 pages.
Exhibit C to Declaration of Jason Johnson in Support of Plaintiff's Opening Claim Construction Brief. Document filed by Gilead Sciences, Inc., Case No. 1:12-cv-06351-RJS (Filed: Oct. 25, 2013), 3 pages.
Gilead Sciences, Inc. Q4 2012 Earnings Results Conference call and Webcast presentation (Feb. 4, 2013), 3 pages.
Gilead Sciences, Inc. Q2 2011 Earnings Results Conference call and Webcast presentation (Jul. 26, 2011), 4 pages.
Exhibit G to of Jason Johnson in Support of Plaintiff's Opening Claim Construction Brief. Document filed by Gilead Sciences, Inc., Case No. 1:12-cv-06351-RJS (Filed: Oct. 25, 2013), 2 page.
Declaration of Amy Patick in Support of Gilead's Claim Construction Document filed by Gilead Sciences, Inc.,. Case No. 1:12-cv-06351-RJS (Filed:Oct. 25, 2013), 13 pages.
Exhibit 1 to Declaration of Amy Patick. Document filed by Gilead Sciences, Inc.,. Case No. 1:12-cv-06351-RJS (Filed:Oct. 25, 2013), 15 pages.
Defendant Cipla Limited's Answer and Separate Defenses to Plaintiff's Second Amended Complaint. Case No. 1:12-cv-06351-RJS (Filed: Nov. 1, 2013), 16 pages.
Defendant CIPLA's Reply to Plaintiff's Opening Claim Construction Brief. Document filed by CIPLA Limited. Case No. 1:12-cv-06351-RJS (Filed: Nov. 22, 2013), 15 pages.
Second Declaration of Aaron M. Johnson in Support of Defendant Cipla's Reply to Plaintiff's Opening Claim Construction Brief. Document filed by CIPLA Limited, Case No. 1:12-cv-06351-RJS (Filed: Nov. 22, 2013), 2 pages.
Honess, R.W. and Watson, D. H.; "Unity and Diversity in the Herpesviruses," *J. Gen. Virol.* (1977), 37:15-37.
Chang, C., et al, "Expression of the precore region of an avian hepatitis B virus is not required for viral replication," *J. Virol.* 1987, 61(10): 3322.
Plantiff's Rebuttal Claim Construction Brief. Document filed by Gilead Sciences, Inc., Case No. 1:12-cv-06351-RJS (Filed: Nov. 22, 2013), 10 pages.
Declaration of Jason Johnson in Support of Plantiff's Rebuttal Claim Construction Brief. Document filed by Gilead Sciences, Inc., (Case No. 1:12-cv-06351-RJS (Filed: Nov. 22, 2013), 2 pages.
Exhibit A to Declaration of Jason Johnson in Support of Plantiff's Rebuttal Claim Construction Brief. Document filed by Gilead Sciences, Inc., Case No. 1:12-cv-06351-RJS (Filed: Nov. 22, 2013), 5 pages.
Letter addressed to Judge Richard J. Sullivan from Christopher P. Borello dated Jul. 28, 2014, Document filed by Gilead Sciences, Inc., Case No. 1:12-cv-06351-RJS (Filed: Jul. 28, 2014), 1 page.
Order on Stipulation for Dismissal Case No. 1:12-cv-06351-RJS— (Dated: Jul. 29, 2014).
Complaint for Patent Infringment. Filed by Gilead Sciences, Inc., Case No. 1:12-CV-06294-RJS (Filed: Aug. 16, 2012), 19 pages.
Plaintiff's Reply to Defendant's Counterclaims. Filed by Gilead Sciences, Inc., Case No. 1:12-CV-06294-RJS (Filed: Nov. 9, 2012), 9 pages.
Order: Filed in Associated Cases:1:12-cv-06294-RJS, 1:12-cv-07910-RJS (Dated: Jul. 23, 2013), 1 page.
Stipulation and Agreement Regarding U.S. Pat. No. 5,922,695, U.S. Pat. No. 5,935,946, U.S. Pat. No. 5,977,089 and U.S. Pat. No. 6,043,230: 1, Case No. 1:12-cv-06294-RJS, (Dated: Aug. 27, 2013), 4 pages.
Order Granting Motion to Dismiss, Case No. 1:12-cv-06294-RJS, (Dated: May 30, 2014), 1 page.
Order regarding Costs, Case No. 1:12-cv-06294-RJS, (Dated May 30, 2014), 4 pages.
Complaint for Patent Infringement. Filed by Gilead Sciences, Inc., Emory University, Case No. 1:14-cv-05352-RJS (Filed Jul. 16, 2014), 12 pages.
Lupin Limited's Answer, Separate Defenses, and Counterclaims to Plaintiff's Complaint. Filed by Lupin Limited.for Case No. 1:14-cv-05352-RJS (Dated: Aug. 22, 2014), 16 pages.
Letter addressed to Judge Richard J. Sullivan from David B. Bassett dated Sep. 16, 2014. Document filed by Emory University, Gilead Sciences, Inc.,Case No. 1:14-cv-05352-RJS (Filed Sep. 16, 2014), 1 page.
Order on Stipulation for Dismissal: Case No. 1:12-cv-06293-RJS (Dated: Sep. 16, 2014), 2 pages.
Complaint for Patent Infringement. Filed by Emory University, Gilead Sciences, Inc., Case No. 1:14-cv-03928-RJS (Filed: Jun. 2, 2014), 18 pages.
Letter addressed to Judge Richard J. Sullivan from Colleen Tracy dated Jun. 27, 2014. Document filed by Emory University, Gilead Sciences, Inc., Case No. 1:14-cv-03928-RJS (Filed: Jun. 27, 2014), 2 pages.
Notice of Voluntary Dismissal Pursuant to F.R.C.P. 41(a)(1)(A)(i) Case No. 1:14-cv-03928-RJS (Dated: Jun. 27, 2014), 1 page.
Complaint for Patent Infringement. Filed by Emory University, Gilead Sciences, Inc., Case No. 1:12-CV-06350 (Filed: Aug. 20, 2012), 14 pages.
Exhibit A to Complaint against CIPLA Limited filed by Emory University, Gilead Sciences, Inc. (mro), Case No. 1:12-CV-06350-RJS (Filed: Aug. 20, 2012),—27 pages.
Exhibit B to Complaint against CIPLA Limited filed by Emory University, Gilead Sciences, Inc. (mro), Case No. 1:12-CV-06350-RJS (Filed: Aug. 20, 2012),—19 pages.
Cipla Limited's Answer and Separate Defences to Plaitiffs' Complaint. Filed by Cipla Limited, Case No. 1:12-CV-06350-RJS (Filed: Dec. 10, 2012), 10 pages.
Letter addressed to Judge Richard J. Sullivan from Christopher P. Borello dated Jul. 28, 2014. Document filed by Emory University, Gilead Sciences, Inc., 1:12-cv-06350-RJS (Dated: Jul. 28, 2014), 1 page.
Attachment to Letter addressed to Judge Richard J. Sullivan from Christopher P. Borello dated Jul. 28, 2014 re: Settlement. Document filed by Emory University, Gilead Sciences, Inc.,.Case No. 1:12-cv-06350-RJS (Dated: Jul. 28, 2014), 2 pages.
Order on Stipulation for Dismissal. Case No. 1:12-cv-06350-RJS (Dated: Jul. 29, 2014), 2 pages.
Declaration of Dr. Jonathan A V Coates in the matter Australian patent application 2011253996 in the name of Gilead Sciences, Inc. and in the matter of Opposition by Alphapharm, Jun. 2, 2015, 22 pages.
Appendix 1 to Complaint Filed by Gilead Sciences, Inc. and Emory University, Case No. 1:14-cv-00099-IMK (Filed: Jun. 10, 2014), 19 pages.
Amended Complaint for Patent Infringement. Filed by Gilead Sciences, Inc. and Emory University, Case No. 1:14-cv-00099-IMK (Filed: Jun. 27, 2014), 18 pages.
Answer, Defenses, and Counterclaims of Mylan Pharmaceuticals Inc. and Mylan Inc., Filed by Mylan Inc., Mylan Pharmaceuticals Inc., Case No. 1:14-cv-00099-IMK (Filed Aug. 12, 2014), 36 pages.
Plaintiff's Answer to Defendants' Counterclaims. Filed by Gilead Sciences, Inc. and Emory University, Case No. 1:14-cv-00099-IMK (Filed: Sep. 2, 2014), 10 pages.
Amended Answer, Defenses, and Counterclaims of Mylan Pharmaceuticals Inc and Mylan Inc., Filed by Mylan Inc., Mylan Pharmaceuticals Inc., Case No. 1:14-cv-00099-IMK (Filed: Sep. 2, 2014), 36 pages.
Stipulation Concerning Defendants Amended Answer, Defenses and Counterclaims, Case No. 1:14-cv-00099-IMK (Filed: Oct. 2, 2014), 2 pages.
Stipulation Regarding Mylan Inc., Filed by Mylan Inc., Case No. 1:14-cv-00099-IMK (Filed: Dec. 15, 2014), 3 pages.
Order Granting Plaintiffs Motion to Amend the Complaint 92 : The Court Grants the motion and Directs the Clerk to file the second

(56) References Cited

OTHER PUBLICATIONS amended complaint. Signed by District Judge Irene M. Keeley on Jan. 22, 2015. (jss) Case No. 1:14-cv-00099-IMK (Dated: Jan. 22, 2015), 1 page.
Second Amended Complaint for Patent Infringement against Mylan Inc. and Mylan Pharmaceuticals Inc. filed by Gilead Sciences, Inc. and Emory University.(JSS) Case No. 1:14-cv-00099-IMK (Filed: Jan. 22, 2015), 21 pages.
Answer, Defenses, and Counterclaims of Mylan Pharmaceuticals Inc. and Mylan Inc. to plaintiffs' second amended complaint, Filed by Mylan Inc., Mylan Pharmaceuticals Inc., Case No. 1:14-cv-00099-IMK (Filed: Feb. 9, 2015), 51 pages.
Joint Stipulation Regarding Claim Construction. Case No. 1:14-cv-00099-IMK (Filed: Feb. 19, 2015), 4 pages.
Gilead's Opening Brief in Support of Its Proposed Claim Constructions for U.S. Pat. No. 8,592,397 and U.S. Pat. No. 8,716,264. Case No. 1:14-cv-00099-IMK (Filed: Feb. 19, 2015), 27 pages.
Declaration of David B. Bassett in Support of Gilead's Opening Brief in Support of Its Proposed Claim Construction. Case No. 1:14-cv-00099-IMK (Filed: Feb. 19, 2015), 134 pages.
Declaration of Patrick J. Sinko, Ph.D., R.Ph., in Support of Gilead's Opening Brief in Support of Its Proposed Claim Construction. Case No. 1:14-cv-00099-IMK (Filed: Feb. 19, 2015), 171 pages.
Declaration of Carlo-Federico Perno, M.D. Ph.D. In Support of Gilead'S Claim Construction., Case No. 1:14-cv-00099-IMK (Filed: Feb. 19, 2015), 14 pages.
Exhibit 1 Declaration of Carlo-Federico Perno, M.D. Ph.D. in Support of Gilead's Claim Construction. Case No. 1:14-cv-00099-IMK (Filed: Feb. 19, 2015), 42 pages.
Exhibit 2 Declaration of Carlo-Federico Perno, M.D. Ph.D. in Support of Gilead's Claim Construction.Case No. 1:14-cv-00099-IMK (Filed: Feb. 19, 2015), 2 pages.
Exhibit 3 Declaration of Carlo-Federico Perno, M.D. Ph.D. in Support of Gilead's Claim Construction. Case No. 1:14-cv-00099-IMK (Filed: Feb. 19, 2015), 3 pages.
Muma, R. D., et al, "Zidovudine adherence among individuals with HIV infection." AIDS Care. 1995;7(4):439-47.
Richman, D.D., "Antiretroviral drug resistance: mechanisms, pathogenesis, clinical significance." *Antiviral Chemotherapy 4*, 383-395 J. Mills, Ed., Plenum Press, New York, 1996.
Johnson, V., "Combination therapy for HIV-1 infection-overview: preclinical and clinical analysis of antiretroviral combinations" *Antiviral Research* 29 (1996) 35-39.
Akanbi, M.O., et al, "Combination nucleoside/nucleotide reverse transcriptase inhibitors for treatment of HIV infection" *Expert Opin Pharmacother*. Jan. 2012;13(1):65-79.
De Clercq, E., "Anti-HIV drugs: 25 compounds approved within 25 years after the discovery of HIV" *Int J Antimicrob Agents*. Apr 2009;33(4):307-20.
Heffernan, J.M. and Wahl, L. M., "Natural variation in HIV infection: Monte Carlo estimates that include CD8 effector cells" *Journal of Theoretical Biology* 243 (2006) 191-204.
Ho, D. D., "Viral Counts Count in HIV Infection," Science vol. 272, 1124-1125, May 24, 1996.
Mellors, J. W., et al, "Prognosis in HIV-1 Infection Predicted by the Quantity of Virus in Plasma" *Science*,vol. 272, 1167-1170, May 24, 1996.
Plaintiffs' Motion to Strike Mylan's Third Separate Defense. Document filed by Gilead Sciences, Inc. and Emory University, Case No. 1:14-cv-00099-IMK (Filed: Mar. 2, 2015), 3 pages.
Declaration of David Bassett in support of Plaintiffs' Motion to Strike Mylan's Third Separate Defense. Document filed by Gilead Sciences, Inc. and Emory University, Case No. 1:14-cv-00099-IMK (Filed: Mar. 2, 2015), 12 pages.
Memorandum in Support of Plaintiffs' Motion to Strike Mylan's Third Separate Defense. Document filed by Gilead Sciences, Inc. and Emory University, Case No. 1:14-cv-00099-IMK (Filed: Mar. 2, 2015), 15 pages.
Plaintiffs' Answer to Defendant Mylan Pharmaceuticals Inc.'s Amended Counter Claims. Document filed by Gilead Sciences, Inc. and Emory University, Case No. 1:14-cv-00099-IMK (Filed: Mar. 2, 2015), 12 pages.
Defendants Mylan Inc. and Mylan Pharmaceuticals Inc.'s Answering Claim Construction Brief in Support of Their Proposed Claim Constructions for U.S. Pat. No. 8,592,397 and U.S. Pat. No. 8,716,264. Document filed by Mylan Inc., Mylan Pharmaceuticals Inc., Case No. 1:14-cv-00099-IMK (Filed: Mar. 12, 2015), 28 pages.
Declaration of Karen M. Cassidy in Support of Defendants Mylan Inc. and Mylan Pharmaceuticals Inc.'s Answering Claim Construction Brief in Support of Their Proposed Claim Constructions for U.S. Pat. No. 8,592,397 and U.S. Pat. No. 8,716,264. Document filed by Mylan Inc., Mylan Pharmaceuticals Inc., Case No. 1:14-cv-00099-IMK (Filed: Mar. 12, 2015), 199 pages.
Declaration of Choloe Lynne Thio, M.D. in Support of Defendants Mylan Inc. and Mylan Pharmaceuticals Inc.'s Answering Claim Construction Brief in Support of Their Proposed Claim Constructions for U.S. Pat. No. 8,592,397 and U.S. Pat. No. 8,716,264. Document filed by Mylan Inc., Mylan Pharmaceuticals Inc., Case No. 1:14-cv-00099-IMK (Filed: Mar. 12, 2015), 184 pages.
Declaration of Frank Chrzanowski, Ph.D. in Support of Defendants Mylan Inc. and Mylan Pharmaceuticals Inc.'s Answering Claim Construction Brief in Support of Their Proposed Claim Constructions for U.S. Pat. No. 8,592,397 and U.S. Pat. No. 8,716,264. Document filed by Mylan Inc., Mylan Pharmaceuticals Inc., Case No. 1:14-cv-00099-IMK (Filed: Mar. 12, 2015), 32 pages.
Gilead's Motion to Defer Consideration of Mylan's Indefiniteness Argument or, Alternatively, for Leave to File a Reply. Case No. 1:14-cv-00099-IMK (Filed: Mar. 19, 2015), 8 pages.
Declaration of David B. Bassett in Support of Gilead's Motion to Defer Consideration of Mylan's Indefiniteness Argument or, Alternatively, for Leave to File a Reply., Case No. 1:14-cv-00099-IMK (Filed: Mar. 19, 2015), 30 pages.
Mylan Inc.'s and Mylan Pharmaceuticals Inc.'s Response to Plaintiffs' Motion to Strike, Case No. 1:14-cv-00099-IMK (Filed: Mar. 19, 2015), 3 pages.
Motion Requesting Expedited Briefing for Gilead's Motion to Defer Consideration of Mylan's Indefiniteness Argument or, Alternatively, for Leave to File a Reply., Case No. 1:14-cv-00099-IMK (Filed: Mar. 19, 2015), 3 pages.
Defendants Mylan Inc. and Mylan Pharmaceuticals Inc.'s Response to Gilead's Motion to Defer Consideration of Mylan's Indefiniteness Argument or, Alternatively, for Leave to File a Reply. Case No. 1:14-cv-00099-IMK (Filed: Mar. 26, 2015), 9 pages.
Declaration of William O. Adams in Support of Defendants Mylan Inc. and Mylan Pharmaceuticals Inc.'s Response to Gilead's Motion to Defer Consideration of Mylan's Indefiniteness Argument or, Alternatively, for Leave to File a Reply. Document filed by Mylan Inc., Mylan Pharmaceuticals Inc., Case No. 1:14-cv-00099-IMK (Filed: Mar. 26, 2015), 20 pages.
Reply Memorandum in Support of Gilead's Motion to Defer Consideration of Mylan's Indefiniteness Argument. Document filed by Emory University and Gilead Sciences, Inc., Case No. 1:14-cv-00099-IMK (Filed: Mar. 30, 2015), 6 pages.
Joint Stipulation Regarding Claim Construction. Signed by District Judge Irene M. Keeley on Mar. 31, 2015. (jss), Case No. 1:14-cv-00099-IMK (Filed: Mar. 31, 2015), 4 pages.
Petition for Inter Partes Review of U.S. Pat. No. 5,922,695, for Case No. IPR2014-00885, filed Jun. 3, 2014, 75 pages.
Corrected Petition for Inter Partes Review of U.S. Pat. No. 5,922,695, for Case No. IPR2014-00885, filed Jun. 24, 2014, 74 pages.
Patent Owner Initial Disclosures Under 37 C.F.R. 42.8 for Case No. IPR2014-00885, filed Jun. 25, 2014, 6 pages.
Gilead's Preliminary Patent Owner Response Under 37 C.F.R. 42.107, for Case No. IPR2014-00885, filed Sep. 18, 2014, 69 pages.
Moyle, Graeme, and Brian Gazzard, "Current Knowledge and Future Prospects for the Use of HIV Protease Inhibitors," 51(5):701-712, Drugs, May 1996.

(56) References Cited

OTHER PUBLICATIONS

Danner, et al., "A Short-Term Study of the Safety, Pharmacokinetics, and Efficacy of Ritonavir, and Inhibitor of HIV-1 Protease," 333:1528-1533, The New England Journal of Medicine, Dec. 1995.
Link, Derek, "The Collapse of Early Intervention at the Ninth International AIDS Conference," 7(6) Treatment Issues, 1993.
Bechtel-Boenning, Christine, "State of the Art Antiviral Treatment of HIV Infection," 31(1):1-13, NIH Nursing Clinics of North America, Mar. 1996.
Leary, Warren E., "F.D.A. Panel Urges Fast Action on Approving a New AIDS Drug," N.Y. Times, Nov. 8, 1995.
HIV/AIDS Historical Time Line 1995-1999, FDA, 6 pages.
Vistide® (cidofovir injection) Package Insert, 2 pages.
Lacy et al., "Evaluation of the Subchronic Toxicity of an Oral Prodrug of the Anti-HIV Nucleotide Analog (9-2-Phosphonylmethoxyethyl)Adenine (PMEA)," 15(1) at 179 Abstract 958, Abstracts of the 34th Annual Meeting of the Society of Toxicology, 1995.
Lalezari et al., "(S)-1-[3-Hydroxy-2-(Phosphonylmethoxy)propyl] cytosine (Cidofovir): Results of Phase I/II Study of a Novel Antiviral Nucleotide Analogue," 171(4):788-796, The Journal of Infectious Diseases, 1995.
Foscavir® (foscarnet sodium) Package Insert, 2 pages.
Lee, William A. and John C. Martin, "Perspectives on the development of acyclic nucleotide analogs as antiviral drugs", 71:254-259, Antiviral Research, 2006.
Park et al., "Acyclovir Permeation Enhancement Across Intestinal and Nasal Mucosae by Bile Salt-Acylcarnitine Mixed Micelles," 9(10):1262-1267, Pharmaceutical Research, 1992.
Fix et al., "Acylcarnitines: drug absorption-enhancing agents in the gastrointestinal tract," 251:G332-G340, Am. J. Physiol., 1986.
Fleisher et al., "Improved oral drug delivery: solubility limitations overcome by the use of prodrugs," 19:115-130, Advanced Drug Delivery Reviews, 1996.
Negi et al., "Studies on Orally Active Cephalosporins: Synthesis and Structure-Activity Relationships of New 3-Substituted Carbamoyloxymethyl Cephalosporins," 47(12):1507-1525, The Journal of Antibiotics, 1994.
Samara et al., "Pharmacokinetic Analysis of Diethylcarbonate Prodrugs of Ibuprofen and Naproxen," 16:201-210, Biopharmaceutics & Drug Disposition, 1995.
World Health Organization Model List of Essential Medicines, 18$^{th}$ Ed. (2013), 47 pages.
Institution Decision Case No. IPR2014-00885, filed Dec. 9, 2014, 23 pages.
Mylan's Updated Exhibit List, Case No. IPR2014-00885, dated Jan. 7, 2015, 9 pages.
Mylan's Request for Rehearing Under 37 C.F.R. 42.71(d), Case No. IPR2014-00885, dated Jan. 8, 2015, 17 pages.
*Gilead Sciences, Inc. v. Teva Pharmaceuticals USA, Inc. et al.*, 10cv-07196-RJS (S. Dist. NY (Foley Square)) (consolidation of 08-cv-10838 ; 12-cv-06351; 12-cv-06294; 12-cv-07910), 1618 pages.
Fischl, M.A., et al., "The Efficacy of Azidothymidine (AZT) in the Treatment of Patients with AIDS and AIDS Related Complex," New England J. Med. 317(4):185-191 (1987).
Richman, D. et al., "The Toxicity of Azidothymidine (AZT) in the Treatment of Patients with AIDS and AIDS Related Complex," New England J. Med. 317:192-7 (1987).
Larder, B.A., Darby, G. and Richman, D., "HIV with reduced sensitivity to zidovudine (AZT) isolated during prolonged therapy," Science 243(4899):1731-1734 (1989).
Kieburtz, KD, et al "Extended follow-up of peripheral neuropathy in patients with AIDS and AIDS related complex treated with dideoxyinosine," J. Acquir. Immune Defic. Syndr. 5:60-64 (1992).
Allan, J.D., et al. "Long term follow-up of didanosine administered orally twice daily to patients with advanced human immunodeficiency virus infection and hematologic intolerance of zidovudine," Clin. Infect. Dis. 16(S1):S46-S51 (1993).

Simpson, D.M. and Tagliati, M., "Nucleoside Analogue Associated Peripheral Neuropathy in Human Immunodeficiency Virus Infection," J. Acquir. Immune Defic. Syndr. and Human Ritrovirology 9:153-161 (1995).
Van Leeuwen, R., et al., "Evaluation of Safety & Efficacy of 3TC Lamivudine in Patients with Asymptomatic or Mildly Symptomatic Human Immunodeficiency Virus Infection: A Phase I/II Study," J. Infect. Dis. 171:1166-71 (1995).
Beck, EJ., et al. "Survival and the use and costs of hospital services for London AIDS patients treated with AZT," Int. J. STD AIDS 7:507-512 (1996).
Boucher, C., et al., "High level Resistance to ( ) Enantiomeric 2'-Deoxy3'-Thiacytidine In Vitro is Due to One Amino Acid Substitution in the Catalytic Site of Human Immunodeficiency Virus Type 1 Reverse Transcriptase," Antimicro. Agents Chemother. 37:2231-2234 (1993).
Mayers, D., "Rational Approaches to Resistance: Nucleoside Analogues," AIDS 10(S1):S9-S13 (1996).
Cleland, A. Watson, HG, Robertson, P., Ludlum, CA and Brown, HA, "Evolution of Zidovudine Resistance-Associated Genotypes in Human Immunodeficiency Virus Type 1-Infected Patients," AIDS 12:6-18 (1996).
Anderson, BD, Shirasaka, T, Kojima E, Yarchoan, R and Mitsuya H, "Identification of drug related genotypic changes in HIV1 from serum using the selective polymerase chain reaction," Antiviral Res. 25:245-258 (1994).
Volberding, P., "The Need for Additional Options in the Treatment of Human Immunodeficiency Virus Infection," J. Infect. Diseases 171(S2):150-154 (1995).
Holy, A., Rosenberg, I., Dvorakova, H. and Declercq, E., "Synthesis and Evaluation of Acyclic Nucleotide Analogs," Nucleosides & Nucleotides 7:667-670 (1988).
Holy, Antonin; Rosenberg, Ivan "9-(Phosphonomethoxyalkyl) adenines, method for their preparation and their use," Eur. Pat. Appl. (1986), EP 206459 A2, 25 pages.
Srinivas, R., Robbins, B., Connelly,M, Gong, Y., Bischofberger, B., Fridland, A., "Metabolism and in Vitro Antiretroviral Activities of is (Pivaloyloxymethyl) Prodrugs of Acyclic Nucleoside Phosphonates," Antimicro. Agents Chemother. 37:2247-2250 (1993).
Heijtink, R.A., et al., "Inhibitory effects of acyclic nucleoside phosphonates on human hepatitis B virus and duck hepatitis B virus infections in tissue culture," Antimicrobial. Agents Chemotherap. 38(9):2180-2182 (1994).
Tsai, C., et al., "Prevention of SIV Infection in Macaques by (R)-9-(2-Phosphonylmethoxypropyl) adenine," Science 270(5239):1197-1199 (1995).
Cohen, J., "New Drug Shows Promise in Monkeys," Science 270:1121-1122 (1995).
Gong, Y., Marshall, D., Srinivas, R., Fridland, A., "Susceptibilities of zidovudine-resistant variants of human immunodeficiency virus type 1 to inhibition by acyclic nucleoside phosphonates," Antimicrobial Agents Chemother. 38(7):1683-1687 (1994).
Examiner's Amendment and Notice of Allowability for U.S. Appl. No. 08/900,746 (dated Apr. 14, 1998), 5 pages.
Kubo, et al. "Nonpeptide angiotensin II receptor antagonists. Synthesis and biological activity of Potential Prodrugs of Benzimidazole-7-carboxylic acids." J Med Chem. 1993 vol. 36, Issue No. 15, pp. 2343-2349.
Balzarini, et al. "Differential Antiherpesvirus and Antiretrovirus Effects of the (S) and (R) Enantiomers of Acyclic Nucleoside Phosphonates: Potent and Selective In Vitro and In Vivo Antiretrovirus Activities of (R)-9-(2-Phosphonomethoxypropyl)-2,6-Diaminopurine" Antimicrobial Agents and Chemotherapy, 1993, vol. 37, No. 2, p. 332-338.
James, John S. "AIDS Treatment News, PMPA in Perspective" AIDS Treatment News Issue No. 236, Dec. 1, 1995.
Editorials, "Carnitine Deficiency" Lancet 335:631-33 (1990).
Islam, I., Hinshaw, R., Chong, K-T., Kato,A., Borchardt, R. and Fisher, J.F. "Synthesis and Antiviral Activity of [2-[[4-[3-[(1-Methylethyl)amino]-2-Pyridyl]-Piperazinyl]Carbonyl]-1H-Indol-5-yl] (BHAP) Acylsphingosine HIV Reverse Transcriptase Inhibitors," Bioorg. Chem. 23:499-511 (1995).

(56) References Cited

OTHER PUBLICATIONS

De Clercq, E., "Antiviral Therapy for Human Immunodeficiency Virus Infections," Clin. Microbiol. Rev. 8(2):200-239 (1995).
Bundgaard, H., "Design of prodrugs" (1985), pp. 4-5, 1 page.
Holme, E. et al., "Carnitine deficiency induced by pivampicillin and pivmecillinam therapy" Lancet 2(8661):469-73 (1989).
"FDA's Policy Satement for the Development of New Stereoisomeric Drugs", Chirality, vol. 4, Issue 5, pp. 338-340, 1992.
Bighley, L.D., et al. "Salt forms of drugs and absorption" in Encyclopedia of Pharm. Tech., Eds. J. Swarbrick and J.C. Boylan, vol. 13 (Marcel Dekker, Inc., New York) (1996), 49 pages.
Gould, Phillip L. "Salt selection for basic drugs", International Journal for Pharmaceutics, (1986) vol. 33, pp. 201-217.
Bisoprolol Fumarate Label (Final Printed Labeling, May 1, 1992), 4 pages.
Bischofberger, N, et al. "Bis(POC)PMPA, an orally bioavailable prodrug of the antiretroviral agent PMPA" Conf. on Retroviruses and Opportunistic Infections 4th:104 (abstract No. 214) (Jan. 22-26, 1997).
Expert Declaration of J. Allen McCutchan, M.D., M.Sc. (dated May 29, 2014), 64 pages.
Expert Declaration of Jed F. Fisher Ph.D. (dated Jun. 3, 2014), 99 pages.
Bordwell, F.G. "Equilibrium Acidities in Dimethyl Sulfoxide Solution" Acc. Chem. Res. (1988) vol. 21, pp. 456-463.
Miyazaki, T., Yanagida, S., Itoh, A., and Okahara, M., "Synthesis and Alkali-cation Complexing Properties of 12-Crown-4 Derivatives", The Chemical Society of Japan, Bull. Chem. Soc. Jpn., (1982) vol. 55, pp. 2005-2009.
Petition for Inter Partes Review of U.S. Pat. No. 5,935,946 for Case No. IPR2014-00886, filed Jun. 4, 2014, 75 pages.
Corrected Petition for Inter Partes Review of U.S. Pat. No. 5,922,695, for Case No. IPR2014-00886, filed Jun. 24, 2014, 74 pages.
Related Matters for Case No. IPR2014-00886, filed Jun. 25, 2014, 6 pages.
Patent Owner Preliminary Response for Case No. IPR2014-00886, filed Sep. 18, 2014, 70 pages.
Institution Decision Case No. IPR2014-00886, filed Dec. 17, 2014, 21 pages.
Mylan's Updated Exhibit List, Case No. IPR2014-00886, dated Jan. 7, 2015, 9 pages.
Request for Rehearing IPR2014-00886, dated Jan. 16, 2015, 15 pages.
Physician's Desk Reference (51 ed. 1997), 28 pages.
Famvir® Package Insert, 16 pages, (Apr. 2013).
Hepsera® Package Insert, 29 pages (Nov. 2012).
Bastin et al., "Salt Selection and Optimisation Procedures for Pharmaceutical New Chemical Entities," Organic Process Research and Development, 4:427-435, 2000.
Van Westrenen et al., "The synthesis of polyhydroxycarboxylates. Part 6. N-Alkylation of amino compounds by a Michael-type addition with maleate," Recl. Trav. Chim. Pays-Bas, 109:474-478, 1990.
Stahl and Basel, Characterization and Improvement of the Stability Behaviour of Drug Substances in Stability Testing in the EC, Japan and the USA 56 (Dr. Wolfgang Grimm and Dr. Kurt Krummen, eds., 45-65 (1993).
Petition for Inter Partes Review of U.S. Pat. No. 5,977,089, for Case No. IPR2014-00887, filed Jun. 4, 2014, 64 pages.
Corrected Petition for Inter Partes Review of U.S. Pat. No. 5,977,089, for Case No. IPR2014-00887, filed Jun. 24, 2014, 63 pages.
Related Matters for Case No. IPR2014-00887, filed Jun. 25, 2014, 6 pages.
Patent Owner Preliminary Response for Case No. IPR2014-00887, filed Sep. 18, 2014, 69 pages.
Institution Decision Case No. IPR2014-00887, filed Dec. 9, 2014, 17 pages.
Mylan's Updated Exhibit List, Case No. IPR2014-00887, dated Jan. 7, 2015, 9 pages.
Rehearing Request, Case No. IPR2014-00887, dated Jan. 8, 2015, 17 pages.
Petition for Inter Partes Review of U.S. Pat. No. 6,043,230, for Case No. IPR2014-00888, filed Jun. 4, 2014, 65 pages.
Corrected Petition for Inter Partes Review of U.S. Pat. No. 6,043,230, for Case No. IPR2014-00888, filed Jun. 24, 2014, 64 pages.
Related Matters for Case No. IPR2014-00888, filed Jun. 25, 2014, 6 pages.
Patent Owner Preliminary Response for Case No. IPR2014-00888, filed Sep. 18, 2014, 67 pages.
Institution Decision Case No. IPR2014-00888, filed Dec. 17, 2014, 20 pages.
Mylan's Updated Exhibit List, Case No. IPR2014-00888, dated Jan. 7, 2015, 9 pages.
Rehearing Request, Case No. IPR2014-00888, dated Jan. 8, 2015, 17 pages.
Notice of Opposition file by Alphapharm Pty Ltd in the Australian Patent Office for Application No. 2011253996, dated Nov. 28, 2014 1 page.
Coffin JM Hughes SH, Varmus HE, editors, "Retroviruses," Cold Spring Harbor (NY) : Cold Spring Harbor Laboratory Press 1997, 4 pages.
White et al., "Molecular Mechanisms of Resistance to Human Immunodeficiency Virus Type 1 with Reverse Transcriptase Mutations K65R and K65R M184V and Their Effects on Enzyme Function and Viral Replication Capacity," Antimicrobial Agents and Chemotherapy, 46(11):2437-3446 (Nov. 2002).
Viread insert, 2001, NDA 21-356, 20 pages.
Epivir Approval Package Mar. 23 ,1999, 22 pages.
Whitney 2002, "The M184V Mutation in Reverse Transcriptase Can Delay Reversion of Attenuated Variants of Simian Immunodrficiency Virus," Journal of Vrology vol. 76 (17) p. 8958-8962.
Retrovir Product information (2001), 23 pages.
Jemsek, Poor Virologic Responses and Early Emergence of Resistance in Treatment Naive, HIV-Infected Patients Receiving a Once Daily Triple Nucleoside Regimen of Didanosine, Lamivudine, and Tenefoir DF, Program Abstr. Conf, Ertrovir, Oppor Infect 11th 2004 San Francisco Calf, Feb. 8-11, 2004. Abstract 51, 1 page.
Farthing, "Early Virologic Failure in a Pilot Study Evaluating the Efficacy of Abacavir, Lamivudine and Tenofovir in the Treatment Naive Hiv-Infected Patients," The 2nd IAS Conference on HIV Pathogenesis and Treatment Abstract No. 43, Jul. 2003, 1 page.
Kagan, "Increasing prevalence of HIV-1 reverse transcriptase mutation K65R correlates with tenofovir utilization," 2004, AntiViral Therapy vol. 9 pp. 827-828.
Fisher, "The safety and efficacy of adefovir dipivoxil in patients with advanced HIV disease: a randomized, placebocontrolled trial," AIDS 15:1695-1700 (2001).
Cihiar, "Human Renal Organic Anion Transporter 1 (HOAT1) Role in the Nephrotoxicity of Antlvlral Nucleotide Analogs," Nucleosides, Nucleotides & Nucleic Acids, 20(4-7):641-648 (2001).
Charpentier, "Evolution of the K65R, K103N and M184V/I reverse transcriptase mutations prevalence in HIV-1 infected patients experiencing virologic failure between 2005 and 2010," Abstract CROI 2012, 1 page.
Grant and Hackh's "Chemical Dictionary" 5th ed. R. Grant (editors) 1987, 7 pages.
Foye's Principles of Medicinal Chemistry 5th ed. 2002, 4 pages.
Center for drug evaluation and research 21-356 Chemistry Review (viread)—12 pages.
Thoithi et al., "Investigation of the kinetics of degradation of hexopyranosylated cytosine nucleosides using liquid chromatography" Nucleosides ,Nucleotides & Nucleic Acids (2003).
Calculating the pH of an aquesou solution of TDF, 1 page.
Handbook of Pharmaceutical Excipients, Fourth Edition, edited by Rowe, Sheskey, and Weller, "Lactose" and "Water," 17 pages (Nov. 2002).

(56) References Cited

OTHER PUBLICATIONS

Kashuba, "Antiretroviral-Drug Concentrations in Semen: Implications for Sexual Transmission of Human Immunodeficiency Virus Type 1," Antimicrobial Agents and Chemotherapy 43(8):1817-1826 (1999).
The Emtriva Label, 19 pages.
Chemistry Reviews for NDA 21-752 Truvada, 27 pages.
Clinical pharmacology section of the ANCOBON, 6 pages (Mar. 2013).
Proloprim, 3 pages.
Ich, Stability Testing of New Drug Substances and Products 2003, 98 pages.
Reynolds et al. "Available Guidance and Best Practices for Conducting Forced Degradation Studies" Pharm Technol 2002, 9 pages.
Carstensen, Jens T. Advances Pharmaceutical Solids, 2001, p. 273, 3 pages.
Novak, "Prevalence of Antiretroviral Drug Resistance Mutations in Chronically HIV-Infected, Treatment-Naïve Patients: Implications for Routine Resistance Screening before Initiation of Antiretroviral Therapy," Clin. Infect Dis. Feb. 1, 2005;40(3) 486-74.
Grant et al., "Preexposure Chemoprophylaxis for HIV Prevention in Men Who Have Sex with Men," New England Journal of Medicine 363:27, 2587-2599 (2010).
Time Magazine, Dec. 9, 2010, "AIDS Drugs Lower the Risk of HIV Infection," by Alice Park, 1 page.
EMEA (European Medicine Agency) Scientific Discussion on Truvada, 28 pages (2005).
EMEA (European Medicine Agency) Scientific Discussion on Emtriva (2005), 30 pages.
Pischetsrieder, "Formation of an Aminoreductone during the Maillard Reaction of Lactose with Nr-Acetyllysine or Proteins," J. Agric. Food Chem. 1998, 46, 928-931.
Bharate, "Interactions and incompatibilities of pharmaceutical excipients with active pharmaceutical ingredients: a comprehensive review ," J. Excipients and Food Chem. 1 (3) (2010), 24 pages.
Novak expert Opinion relating to opposition proceedings being conducted in Israel against Gilead Sciences, Inc. ("the Applicant"), concerning Israel patent application No. IL 169243 ("the Patent Application"), 40 pages.
Second Expert Opinion Prof Richard M.Novak relating to opposition proceedings being conducted in Israel against Gilead Sciences, Inc. ("the Applicant"), concerning Israel patent application No. IL 169243, Apr. 9, 2014, 50 pages.
Expert Opinion Prof. Joseph Marian Fortunak relating to opposition proceedings being conducted in Israel against Gilead Sciences, Inc. ("the Applicant"), concerning Israel patent application No. IL 169243, Sep. 20, 2012, 30 pages.
Expert Opinion of Dr. G. Patrick Stahly filed in the Israeli Patent Office in opposition proceedings initiated by Teva Pharmaceutical Industries Ltd. against Israeli Patent Application No. 169,243, filed by GileadSciences Inc., 27 pages (undated).
Truvada Summary of Product Characteristics, 35 pages (Stahly Exhibit).
Shapiro and Klein "The Deamination of Cytidine and Cytosine by Acidic Buffer Solutions. Mutagenic Implications," *Biochemistry*, 5(7): 2358-2362 ( 1966).
Notari, "A Mechanism for the Hydrolytic Deamination of Cytosine Arabinoside in Aqueous Buffer," *Journal of Pharmaceutical Science*, vol. 56, No. 7, Jul. 1967, 804-809.
Notari, "Intermolecular and Intramolecular Catalysis in Deamination of Cytosine Nucleosides," *Journal of Pharmaceutical Science*, vol. 59, No. 1, Jan. 1970, 28-32.
Lonnberg, "Competition between the hydrolysis and Deamination of cytidine and its 5-substituted deirivatives in aqueous acid," Nucleic Acid Research, vol. 13, Nov. 1985, 2451-2456.
Dong, "Modeling of Autocatalytic Hydrolysis of Adefovir Dipivoxil in Solid Formulation" Journal of the Pharmaceutical Society of Japan, 131(4), 643-654 (2011).

Wong, "Major Degradation Product Identified in Several Pharmaceutical Formulations against the Common Cold," *Anal. Chem.*, 2006, 78, 7891-7895.
Aulton, *Pharmaceutics the Science of Dosage Form Design* (1988), 618.
Augsburger, "Tablet Formulation," *Encyclopedia of Pharmaceutical Technology* ($3^{rd}$ . ed.), 3646, 13 pages (2007).
Armstrong, "Tablet Manufacture by Direct Compression," Encyclopedia of Pharmaceutical Technology (3rd. ed.), 3673-3683 (2007).
Chan, "Excipients: Powders and Solid Dosage Forms," Encyclopedia of Pharmaceutical Technology (3rd. ed.), 1646-1655 (2007).
Airaksinen, "Role of Water in the Physical Stability of Solid Dosage Formulations," *Journal of Pharmaceutical Sciences*, vol. 94, No. 10, 2147-2165 (2005).
Ahlneck and Zografi, "The molecular basis of moisture effects on the physical and chemical stability of drugs in the solid state," *International Journal of Pharmaceutics*, 62 (1990) 87-95.
Kaupp, "Solid-state reactions, dynamics in molecular crystals," *Current Opinion in Solid State & Material Science*, 6 (2002) 131-138.
Byrn, "Chemical reactivity in solid-state pharmaceuticals: formulation implications," *Advanced Drug Deliveries Reviews* 48, 115-136 ( 2001).
Li, "The Solid State Michael Addition of Indole to 4-Arylidene-3-methyl-5 pyrazolone," *J. Heterocyclic. Chem.*, 36, 697-701 (1999).
Frantz, "The Trouble with Making Combination Drugs," News & Analysis section of *Nature Review Drug Discovery*, vol. 5, 881-882 (2006).
Summary of Preformulation Report for GS-4331 fumarate salt,1 page (1997).
Flemming, "Compaction of lactose drug mixtures: Quantification of the extent of incompatibility by FT-Raman spectroscopy," *European Journal of Pharmaceutics and Biopharmaceutics* 68, 802-810 (2007).
Desai, "Preformulation compatibility studies of etamsylate and fluconazole drugs with lactose by DSC," *Journal of Thermal Analysis*, vol. 71, 651-658 (2003).
Gokhale, "Glycosylation of Aromatic Amines I: Characterization of Reaction Products and Kinetic Scheme," *AAPS PharmaSciTech*, vol. 10, No. 2, 317-328 (2009).
Gallo, et al., "Frequent Detection and Isolation of Cytopathic Retroviruses (HTL V-III) from Patients with AIDS and at Risk for AIDS," *Science, New Series*, vol. 224, No. 4648 (May 4, 1984), 500-503.
Expert Opinion of Prof. Robert R. Redfield in opposition proceedings initiated by Teva Pharmaceutical Industries Ltd. against Israeli Patent Application No. 169,243, filed by Gilead Sciences Inc., 38 pages (undated).
Redfield, "Frequent Transmission of HTLV-III Among Spouses of Patients with AIDS-Related Complex and AIDS", *JAMA* 1985; 253(11):1571-1573.
Redfield, "The Walter Reed Staging Classification for HTLV III, LAV Infection", *New England Journal of Medicine* 1986; 314: 131-132.
Baeten et al., "Antiretroviral Prophylaxis for HIV Prevention in Heterosexual Men and Women," New England Journal of Medicine 367:5, 399-410 (2012).
Thigpen et al., "Antiretroviral Preexposure Prophylaxis for Heterosexual HIV Transmission in Botswana," New England Journal of Medicine 367:5, 423-434 (2012).
Highlights of Prescribing Information for TRUVADA, 45 pages, Jul. 2004.
Grossman, et al., "Drug-Resistant HIV Infection among Drug-Naïve Patients in Israel," Journal of Clinical Infectious Disease 40, 294-302 (2005).
Bazmi, "In Vitro Selection of Mutations in the Human Immunodeficiency Virus Type 1 Reverse Transcriptase That Decrease Susceptibility to β-D-Dioxolane-Guanosine and Suppress Resistance to 39-Azido-39-Deoxythymidine," Antimicrobial Agents and Chemotherapy, 44(7):1783-1788 (2000).

(56) References Cited

OTHER PUBLICATIONS

Roge, "Genotypic and phenotypic changes in antiretroviral-naive patients experiencing failure on randomised treatment with abacavir, didanosine and stavudine," Antiviral Therapy, 7, S125 (2002), 1 page.
Dart Virology Group and Trial Team, "Virological response to a triple nucleoside/nucleotide analogue regimen over 48 weeks in HIV-1-infected adults in Africa," AIDS 20(10), 1391-1399 (2006).
Rey, "Virologic Response of Zidovudine, Lamivudine, and Tenofovir Disoproxil Fumarate Combination in Antiretroviral-Naive HIV-1-Infected Patients," *J. AIDS* 43(5), 530-534 (2006).
Kirkland, "Response to Lamivudine-Zidovudine plus Abacavir Twice Daily in Antiretroviral-Naive, Incarcerated Patients with HIV Infection Taking Directly Observed Treatment," Clinical Infectious Diseases, 34, 511-518 (2002).
Little, "Antiretroviral-Drug Resistance Among Patients Recently Infected With HIV," New England Journal of Medicine, 347(6), 385-394 (2002).
Rubio,"Increase in the frequency of mutation at codon 215 associated with zidovudine resistance in HIV-1-infected antiviral-naive patients from 1989 to 1996," AIDS, 11(9), 1184-1186 (1997).
Winston, "The prevalence and determinants of the K65R mutation in HIV-1 reverse transcriptase in tenofovir-naive patients," *AIDS*, 16(15), 2087-2089 (2002).
Pillay, "HIV Type 1 Subtype C Drug Resistance among Pediatric and Adult South African Patients Failing Antiretroviral Therapy,"*AIDS Research Human Retroviruses*, 24, 1449-1454 (2008).
Loemba, "Genetic Divergence of Human Immunodeficiency Virus Type 1 Ethiopian Clade C Reverse Transcriptase (RT) and Rapid Development of Resistance against Nonnucleoside Inhibitors of RT," *Antimicrobial Agents and Chemotherapy*, 46(7), 2087-2094 (2002).
Lambert, "Prevalence of pre-existing resistance-associated mutations to rilpivirine, emtricitabine and tenofovir in antiretroviral-naïve patients infected with B and non-B subtype HIV-1 viruses," *Journal of Antimicrobial Chemotherapy* (2013), 6 pages.
Arion, "The K65R Mutation Confers Increased DNA Polymerase Processivity to HIV-1 Reverse Transcriptase ," *J. Biological Chemistry*, 271(33):19860-19864 (1996).
Miller, "Human Immunodeficiency Virus Type 1 Reverse Transcriptase Expressing the K70E Mutation Exhibits a Decrease in Specific Activity and Processivity," Molecular Pharmacology, 54, 291-297 (1998).
The FDA's press release dated Jul. 2, 2002 reporting the new approved dosing for EPIVIR (3TC), titled "New Dosing approved for Epivir (lamivudine)," 1 page.
Raune, "Pharmacodynamic effects of zidovudine 600 mg once daily versus zidovudine 300 mg twice daily in therapy-naïve HIVinfected patients (COD20002)," Late Breaker Poster Exhibition: *The XIV International AIDS Conference* (2002), 1 page.
FDA Press Release Zerit XR, Dec. 31, 2002, titled "Approval of ZERIT® XR, a new formulation that allows once-a-day dosing," 1 page.
FDA Videx EC Approval Letter dated Oct. 31, 2000, 3 pages.
Callender, "Pharmacokinetics of Oral Zidovudine Entrapped in Biodegradable Nanospheres in Rabbits," *Antimicrobial Agents and Chemotherapy* 43(4), 972-974 (1999).
Cohen, "Week 48 Analysis of Once-Daily (QD) Trizivir (TZV) and Tenofovir DF (TDF) in Antiretroviral Naïve Subjects (COL40263)," *45th Interscience Conference on Antimicrobial Agents and Chemotherapy* Poster H-521, 1 page.
Elion, "Once-Daily Abacavir/Lamivudine/Zidovudine plus Tenofovir for the Treatment of HIV-1 Infection in Antiretroviral-Naïve Subjects: A 48-Week Pilot Study," *HIV Clinical Trials*, 7(6), 324-333 (2006).
Meier, "Cidofovir-induced End-Stage Renal Failure," Nephrology Dialysis Transplantation, 17, 148-149 (2002).
Verhelst, "Fanconi Syndrome and Renal Failure Induced by Tenofovir: A First Case Report," American Journal of Kidney Diseases, 40(6), 1331-1333 (2002).
Coca, S., and Perazella, M., " Rapid Communication: Acute Renal Failure Associated with Tenofovir: Evidence of Drug-Induced Nephrotoxicity," American Journal of Medical Science 324(6), 342-344 (2002).
Bowonwatanuwong, "A Randomised, Open Label Study to Investigate Abacavir ( ABC) and Lamivudine (3TC) as Once Daily (QD) Components of a Triple Combination Regimen (EPV40001).," 1st IAS Conference, Buenos Aires, Argentina, Jul. 8-11, 2001, 1 page.
Statement in Response by Applicant in opposition proceedings initiated by Teva Pharmaceutical Industries Ltd. against Israeli Patent Application No. 169,243, filed by Gilead Sciences Inc., 27 pages (undated).
Memorandum Opinion and Order Granting Plaintiffs' Motion to Defer Consideration of Mylan's Indefiniteness Argument [DKT. No. 119], CV No. 1:14CV99, signed Apr. 6, 2015.
Statement concerning Request for Intervention for Case No. 3k:26-27, Turkish Patent No. TR 2008 067, dated Apr. 13, 2015, 25 pages.
İlko İlaç San. ve Tic. A.Ş .'s Invalidation Petition for Turkish Patent No. 2008/06970 filed Sep. 19, 2014, 41 pages.
Gilead Sciences, Inc.'s Response to İlko İlaç San. ve Tic. A.Ş .'s Invalidation Petition for Turkish Patent No. 2008/06970 filed Dec. 31, 2014, 36 pages.
İlko İlaç San. Ve Tic. A.Ş .'s Second Invalidation Petition for Turkish Patent No. 2008/06970 field Feb. 26, 2015 (Translation), 8 pages.
Plaintiffs' Response to Defendants' Pretrial Memrorandum filed by Bristol-Meyers, Squibb Company, Merck, Sharp &Dohme Corp., Case No. 1:10-cv-01851-RJS, (Filed May 24, 2013), 19 pages.
Defendants' Memorandum of Law in Oppositon to Plaintiffs' Opening Pretrial Brief filed by Teva Pharmaceutical Industries, Ltd., Teva Pharmaceuticals USA, Inc., Case No. 1:10-cv-01851-RJS, (Filed May 24, 2013), 18 pages.
Stipulation and Order of Dismissal, Case No. 1:10-cv-01851-RJS (Dated Aug. 16, 2013), 2 pages.
Affidavit of Calvin J. Cohen, M.D. filed by Emory University, Gilead Sciences, Inc., Case No. Case: 1:08-cv-10838-RJS (Filed Sep. 9, 2013), 41 pages.
Affidavit of Paul A. Bartlett, Ph.D. filed by Emory University, Gilead Sciences, Inc.,Case No. 1:08-cv-10838-RJS (Filed Sep. 9, 2013), 39 pages.
Affidavit of Carlo-Federico Perno, M.D., Ph.D. filed by Emory University, Gilead Sciences, Inc.,Case No. 1:08-cv-10838-RJS (Filed Sep. 9, 2013), 50 pages.
Affidavit of Dennis C. Liotta, Ph.D. filed by Emory University, Gilead Sciences, Inc.,Case No. 1:08-cv-10838-RJS (Filed Sep. 9, 2013), 31 pages.
Affidavit of Judi Weissinger, Ph.D. filed by Emory University, Gilead Sciences, Inc.,Case No. 1:08-cv-10838-RJS (Filed Sep. 9, 2013), 13 pages.
Affidavit of Stephen G. Davies, Ph.D. filed by Emory University, Gilead Sciences, Inc.,Case No. 1:08-cv-10838-RJS (Filed Sep. 9, 2013), 42 pages.
Affidavit of Daniel C. Smith, Ph.D. filed by Emory University, Gilead Sciences, Inc.,Case No. 1:08-cv-10838-RJS (Filed Sep. 9, 2013), 31 pages.
Affidavit of James Meyers filed by Emory University, Gilead Sciences, Inc.,Case No. 1:08-cv-10838-RJS (Filed Sep. 9, 2013), 15 pages.
Plaintiffs' Pretrial Memorandum filed by Emory University, Gilead Sciences, Inc.,Case No. 1:08-cv-10838-RJS (Filed Sep. 9, 2013), 60 pages.
Plaintiffs' Proposed Findings of Fact and Conclusions of Law, filed by Emory University, Gilead Sciences, Inc.,Case No. 1:08-cv-10838-RJS (Filed Sep. 9, 2013), 85 pages.
Declaration of Harry Boghigian filed by Teva Pharmaceutical Industries Limited, Teva Pharmaceuticals USA, Inc., Case No. 1:08-cv-10838-RJS (Filed Sep. 9, 2013), 17 pages.

(56) References Cited

OTHER PUBLICATIONS

Declaration of Stanley Roberts, Ph.D., filed by Teva Pharmaceutical Industries Limited, Teva Pharmaceuticals USA, Inc., Case No. 1:08-cv-10838-RJS (Filed Sep. 9, 2013), 78 pages.
Defendants' Pretrial Memorandum filed by Teva Pharmaceutical Industries Limited, Teva Pharmaceuticals USA, Inc., Case No. 1:08-cv-10838-RJS (Filed Sep. 9, 2013), 47 pages.
Defendants' Proposed Findings of Fact and Conclusions of Law filed by Teva Pharmaceutical Industries Limited, Teva Pharmaceuticals USA, Inc., Case No. 1:08-cv-10838-RJS (Filed Sep. 9, 2013), 68 pages.
Defendants' Memorandum of Law in Opposition to Plantiffs' Pretrial Memorandum filed by Teva Pharmaceutical Industries Limited, Teva Pharmaceuticals USA, Inc., Case No. 1:08-cv-10838-RJS (Filed Sep. 23, 2013), 31 pages.
Plaintiffs' Opposition to Teva's Pretrial Memorandum, filed by Emory University, Gilead Sciences, Inc. Case No. 1:08-cv-10838-RJS (Filed Sep. 23, 2013), 41 pages.
Amendend Declaration of Stanley Roberts, Ph.D. filed by Teva Pharmaceutical Industries Limited, Teva Pharmaceuticals USA, Inc., Case No. 1:08-cv-10838-RJS (Filed Oct. 4, 2013), 77 pages.
Transcript of Proceedings regarding Trial held on Oct. 8, 2013 before Judge Richard J. Sullivan, Case No. 1:08-cv-10838-RJS (Dated Oct. 21, 2013), 222 pages.
Transcript of Proceedings regarding Trial held on Oct. 9, 2013 before Judge Richard J. Sullivan, Case No. 1:08-cv-10838-RJS (Dated Oct. 21, 2013), 220 pages.
Transcript of Proceedings regarding Trial held on Oct. 10, 2013 before Judge Richard J. Sullivan, Case No. 1:08-cv-10838-RJS (Dated Oct. 21, 2013), 38 pages.
Transcript of Proceedings regarding Trial held on Oct. 28, 2013 before Judge Richard J. Sullivan, Case No. 1:08-cv-10838-RJS (Dated Nov. 7, 2013), 67 pages.
Stipulated Statement of Corrections to Trial Transcript, October 8-10, 28, 2013 filed by Emory University, Gilead Sciences, Inc. Case No. 1:08-cv-10838-RJS (Filed Dec. 4, 2013), 42 pages.
Plaintiffs' Post-Trial Brief filed by Emory University, Gilead Sciences, Inc. Case No. 1:08-cv-10838-RJS (Filed Dec. 4, 2013), 43 pages.
Defendants' Post-Trial Memorandum filed by Teva Pharmaceutical Industries Limited, Teva Pharmaceuticals USA, Inc., Case No. 1:08-cv-10838-RJS (Filed Dec. 4, 2013), 43 pages.
Defendants' Revised Proposed Findings of Fact and Conclusions of Law filed by Teva Pharmaceutical Industries Limited, Teva Pharmaceuticals USA, Inc., Case No. 1:08-cv-10838-RJS (Filed Dec. 4, 2013), 102 pages.
Plaintiffs' Proposed Findings of Fact and Conclusions of Law filed by Emory University, Gilead Sciences, Inc. Case No. 1:08-cv-10838-RJS (Dec. 5, 2013), 111 Pages.
Plaintiffs' Notice of PTX, A, B, and C (exhibits) in Support of Post-trial Memorandum regarding Post Trial Memorandum filed by Emory University, Gilead Sciences, Inc. Case No. 1:08-cv-10838-RJS, (Filed Dec. 5, 2013), 81 pages.
Plaintiffs' Opposition to Defendants' Post-Trial Memorandum filed by Emory University, Gilead Sciences, Inc. Case No. 1:08-cv-10838-RJS (Filed Dec. 18, 2013), 22 pages.
Defendants' Post-Trial Reply Memorandum filed by Teva Pharmaceutical Industries Limited, Teva Pharmaceuticals USA, Inc., Case No. 1:08-cv-10838-RJS (Filed Dec. 18, 2013), 20 pages.
Stipulation of Dismissal, Case No. 1:08-cv-10838-RJS (Dated Jan. 29, 2014), 3 pages.
Order, Case No. 1:08-cv-10838-RJS (Dated Feb. 13, 2014), 1 page.
Order on Stipulation for Dismissal, Case No. 1:08-cv-10838_RJS (Dated Apr. 30, 2014), 2 pages.
Rudnic, E., Remington 20th Edition, Chapter 45, pp. 996-1035, (2000).
Declaration of Andrew David Carr in the matter Australian patent application 2011253996 in the name of Gilead Sciences, Inc. and in the matter of Opposition by Alphapharm, Jun. 2, 2015, 62 pages.

Declaration of Helen Grimes in the matter Australian patent application 2011253996 in the name of Gilead Sciences, Inc. and in the matter of Opposition by Alphapharm, Jun. 2, 2015, 61 pages.
Statement of Grounds and Particulars filed by Alphapharm Pty Ltd in the Australian Patent Office for Application No. 2011253996, dated Mar. 17, 2015, 12 pages.
Australian Product Information for EMTRIVA (emtricitabine) Capsules, Apr. 2014, 22 pages.
Australian Product Information for Viread® (tenofovir disoproxil fumarate) 300 mg Tablets, Oct. 2013, 44 pages.
Australian Product Information for 3TC® Tablets and Oral Solution , Feb. 2015, 26 pages.
Australian Product Information for REYATAZ® (atazanavir sulfate), Dec. 2014, 52 pages.
Australian Product Information for STOCRIN® (efavirenz), Mar. 2015, 29 pages.
Australian Product Information for KALETRA, Jan. 30, 2015, 39 pages.
Abstracts of the 10th Conference on Retroviruses and Opportunistic Infections Feb. 10-14, 2003, p. 10, Abstract 564b (A-564b), 5 pages.
Braunwald et al, Harrison's Principles of Internal Medicine (McGraw-Hill, 15th ed, 2001),pp. 1852-1913 (Harrison's).
Cadman et al., "Looking Down the Drugline Pipeline," GMHC Treat Issues 12(3):5-9 (1998).
Memorandum Opinion and Order Construing Patent Claims, signed by Judge Irene M. Keeley, Case No. 1:14-cv-00099-IMK (dated: May 12, 2015), 44 pages.
Plaintiffs' Motion to Compel Defendants to Produce Documents, Case No. 1:14-cv-00099-IMK (Filed: May 28, 2015), 9 pages.
Decision Denying Petitioner'S Request for Rehearing for Case PTAB-IPR2014-00885, dated Aug. 3, 2015, 15 pages.
Decision Denying Petitioner'S Request for Rehearing for Case PTAB-IPR2014-00887, dated Aug. 3, 2015, 13 pages.
Decision Denying Petitioner'S Request for Rehearing for Case PTAB-IPR-2014-00888, dated Aug. 3, 2015, 15 pages.
Joint Motion to Dismiss and Stipulation by Mylan Inc., Mylan Pharmaceuticals Inc., Case No. 1:14-cv-00099-IMF-JSK (Dated: Oct. 30, 2015), 3 pages.
Order on Stipulation for Dismissal: Ordered, adjudged and decreed that all claims, counterclaims or causes of action asserted in this suit by and between Gilead, Emory and Mylan are dismissed with prejudice. Signed by District Judge Irene M. Keeley on Nov. 2, 2015. (jss), Case No. 1:14-cv-00099-IMF-JSK (Entered: Nov. 2, 2015), 2 pages.
Report to USPTO on the filing or determination of an action regarding re 232 Order/Stipulation on Motion to Dismiss. (jss) Case No. 1:14-cv-00099-IMF-JSK (Entered: Nov. 5, 2015), 1 page.
"Institute of Human Virology Hosts Prominent AIDS Researchers During 16$^{th}$ Annual InternationalMeeting," Sep. 11, 2014, Business Wire, retrieved from the Internet on Nov. 3, 2015 http://somvweb.som.umaryland.edu/absolutenm/templates/?a=2879&z=41, 2 pages.
The Telegraph, "Inventor of Tamiflu profits from swine flu pandemic" Jul. 27, 2009, 2 pages.
Gallant, "Efficacy and Safety of Tenofovir DF vs stavudine in combination therapy in Antiretroviral-Naïve Patients," JAMA 292(2):191-201( Jul. 14, 2004).
Gallant "Early Virologic Nonresponse to Tenofovir, Abacavir, and Lamivudine in HIV-Infected Antiretroviral-Naive Subjects," Dec. 1, 2005 JID:192:1921-1930.
"Birth of a Notion: From the Lab to the Marketplace; Technology Transfer at Emory," Oct. 31, 1996, retrieved from the Internet on Nov. 3, 2015 at http://www.whsc.emory.edu/_pubs/em/1996fall/tech_transfer.html, 6 pages.
Medical Review 21-752: tenofovir and emtricitabine, Jul. 26, 2004, 26 pages.
Gilead's Poster 616—10th Conference on Retroviruses and Opportunistic Infections. (CROI) Feb. 10-14, 2003, 1 page.
Stone, "Human Immunodeficiency Virus Type 1 Reverse Transcriptase Mutation Selection during In Vitro Exposure to Tenofovir Alone or Combined with Abacavir or Lamivudine," Antimicrobial Agents and Chemotherapy vol. 48 No. 4, Apr. 2004, p. 1413-1415.

(56) References Cited

OTHER PUBLICATIONS

ADIS R&D Profile, "Emtricitabine," Drugs R&D Jan. 2003; 4(1): 42-48.
Theory and Practice of Industrial Pharmacy, 3rd Edition, Lachman et al., Eds., Lea & Febiger, pp. 293-294 (1986).
EMEA Scientific Discussion for Viread®, 43 pages (2004).
Rudnic and Schwartz, "Oral Solid Dosage Forms" in "Remington: The science and Practice of Pharmacy", 2000, Eds Gennaro et al., p. 858-871.
Declaration of Dr. Reza Oliyai, dated Sep. 17, 2015, 2 pages.
Order Granting Motion to Withdraw for PTAB-IPR2014-00885, dated Nov. 19, 2015, 3 pages.
Order Granting Motion to Withdraw for PTAB-IPR2014-0086, dated Nov. 19, 2015, 4 pages.
Order Granting Motion to Withdraw for PTAB-IPR2014-0087, dated Nov. 19, 2015, 3 pages.
Order Granting Motion to Withdraw for PTAB-IPR2014-0088, dated Nov. 19, 2015, 4 pages.
Decision Denying Petitioner's Request for Rehearing of Decision Denying Insitution of Inter Partes Review for PTAB-IPR2014-00886, dated Nov. 19, 2015, 12 pages.
Extended Search Report issued by the European Patent Office for Application No. 15154733.8, dated Nov. 9, 2015.
Notification Prior to Refusal of the Patent Application No. 188016 issued by the Israeli Patent Office, dated Dec. 8, 2015, 3 pages (includes translation).
Yuan et al, "Effect of Carbonate Salts on the Kinetics of Acid-Catalyzed Dimerization of Adefovir Dipivoxil," Pharmaceutical Research 17(19):1098-1103 (2000).
Reza Oliyai e al., "Kinectic Studies of the Degradation of Oxycarbonyloxymethyl Prodrug of Adefovir and Tenofovir in Solution," Nucleosides, Nucleotides & Nucleic Acids 20 (4-7):1295-1298 (2001).
Augustijns, P et al., High Speed HPLC Determination of bis(pivaloyloxymethyl)-PMEA and Its Degradation Products Mono(POM)-PMEA and PMEA J. Liq. Chrom. & Rel. Technol. vol. 19, No. 14, 2271-2283 (1996).
Rowe, Raymond et al., Handbook of Pharmaceutical Excipients London UK Science and Practice, 4$^{th}$ Ed., pp. 289-293 and 568-570 (2003).
Truvada® Prescribing Information, 2004, 51 pages.
Press Release, Bristol-Myers Squibb and Gilead Sciences Establish U.S. Joint Venture to Develop and Commercialize Fixed-Dose Combination of Three HIV Medicines, Dec. 20, 2004, 4 pages.
Chiarello, Kaylynn, "Big Pharma Companies Team Up to Develop Once-Daily Triple-Combination HIV Drug," Pharmaceutical Science & Technology News, p. 4 (2005).
FDA, International Conference on Harmonisation Draft Revised Guidance on Impurities in New Drug Products, Fed. Reg. vol. 65, No. 139, pp. 44791-44797 (2000).
FDA, International Conference on Harmonisation Draft Revised Guidance on Q1A(R) Stability Testing of New Drug Substances and Products, Fed. Reg. vol. 65, No. 78, pp. 21446-21453 (2000).
Pre-Formulation Report, Compatibility of Tenofovir Disoproxyl Fumarate with surfactants, 2 pages.
Akers, M., "Preformulation Testing of Solid Oral Dosage Form Drugs Methodoloty, Management, and Evaluation," Canadian Journal of Pharmaceutical Sciences 11(1):1-10 (1976).
Monkhouse, "Stability Aspects of preformulation and formulation of soild pharmaceuticals," Drug Dev Ind Pharm., 10 (8&9):1373-1412 (1984).
Lachman, Leon et al, "The Theory and Practice of Industrial Pharmacy," 3rd Edition, Philadelphia, USA, Lea and Febiger, pp. 190-194 (1986).
Overgaard et al., "Patents' Evaluation of Shape, Size and Colour of Solid Dosage Forms," Pharm World Sci, 2nd Ed, 23(5):185-188 (2001).
International Conference on Harmonisation of Technical Requirements for Registration of Pharmaceuticals for Human Use, ICH Harmonised Tripartite Guideline, Pharmaceutical Development Q8, Current Step 4 version, pp. 1-7 (2005).
Notice of Opposition against EP2386294, European Application No. 11167101.2,, filed by Accord Healthcare Ltd, Dec. 4, 2015, 24 pages.
Notice of Opposition against EP2386294, European Application No. 11167101.2,, filed by Hetero Drugs Ltd, dated Dec. 4, 2015, 12 pages.
Notice of Opposition against EP2386294, European Application No. 11167101.2,, filed by Keltie, 12 pages Dec. 4, 2015.
Notice of Opposition against EP2386294, European Application No. 11167101.2,, filed by Sandoz, 20 pages, dated Dec. 4, 2015.
Notice of Opposition against EP2386294, European Application No. 11167101.2, filed by Strawman Limited, Dec. 4, 2015, 32 pages.
Staszewski, S., J. Gallant, A. Pozniak, J. M. A. H. Suleiman, E. Dejesus, E. Koenig, S. Coleman et al. "Efficacy and safety of tenofovir disoproxil fumarate (TDF) versus stavudine (d4T) when used in combination with lamivudine (3TC) and efavirenz (EFV) in HIV-1 infected patients naive to antiretroviral therapy (ART): 48-week interim results." Oral 17, 14th International AIDS Conference, Jul. 7-12, 2002 (poster), 1 page.
Staszewski, S., J. Gallant, A. Pozniak, J. M. A. H. Suleiman, E. Dejesus, E. Koenig, S. Coleman et al. "Efficacy and safety of tenofovir disoproxil fumarate (TDF) versus stavudine (d4T) when used in combination with lamivudine (3TC) and efavirenz (EFV) in HIV-1 infected patients naive to antiretroviral therapy (ART): 48-week interim results of Study GS-99-903" Oral 17, 14th International AIDS Conference, Jul. 7-12, 2002 (presentation), 23 pages.
Clinical Study Report for Efavirenz Emtricitabine Tenofovir Disoproxil Fumarate, dated Jul. 28, 2005, 322 pages.
Final Clinical Study Report for Efavirenz Emtricitabine Tenofovir Disoproxil Fumarate, dated Nov. 28, 2006, 342 pages.
Office Action issued by the United States Patent and Trademark Office for U.S. Appl. No. 14/523,783, dated Sep. 17, 2015, 13 pages.
Gao, et al., "Investigation of Human Pharmacoscintigraphic Behavior of Two Tablets and a Capsule Formulation of a High Dose, Poorly Water Soluble/Highly Permeable Drug (Efavirenz)," Journal of Pharmaceutical Sciences, 96(11):2970-2977 (2007).
Extended European Search Report issued by the European Patent Office for Application No. 15190214.5, dated Apr. 15, 2016, 11 pages.
Hughes, B., "Tapping into Combination Pills for HIV," News & Analysis, Nature Reviews, Drug Discovery, vol. 8, 439-440 (2009).
Notice of Allowance and Examiner Interview Summary issued by the United States Patent and Trademark Office for U.S. Appl. No. 14/523,758, dataed May 20, 2016, 12 pages.
Efavirenz/Emtricitabine/Tenofovir Disoproxil Fumarate Final CSR GS-US-177-0103 Final CSR GS-US-77-0103, dated Jan. 17, 2006, 328 pages.
Efavirenz/Emtricitabine/Tenofovir Disoproxil Fumarate Final CSR GS-US-177-0104, dated Nov. 30, 2006, 306 pages.
U.S. Pat. No. 5,922,695C1 (Ex Parte Reexamination Certificate) to Murty N. Arimilli, Kenneth C. Cundy, Joseph P. Dougherty, Choung U. Kim, Reza Oliyai and Valentino J. Stella, issued on Oct. 14, 2008 (Mylan's Updated Exhibit List Jan. 7, 2015).
U.S. Pat. No. 5,922,695 Prosecution File History (U.S. Appl. No. 08/900,746, filed Jul. 25, 1997).
U.S. Pat. No. 5,922,695 Reexamination File History (Reexamination Request No. 90/008,555, filed Apr. 30, 2007).
U.S. Pat. No. 5,977,089C1 (Ex Parte Reexamination Certificate) to Murty N. Arimilli, Kenneth C. Cundy, Joseph P. Dougherty, Choung U. Kim, Reza Oliyai and Valentino J. Stella, issued on Nov. 25, 2008.
U.S. Pat. No. 5,977,089 Reexamination File History (Reexamination Request No. 90/008,550, filed Apr. 30, 2007).
U.S. Pat. No. 6,043,230 (Ex Parte Reexamination Certificate) to Murty N. Arimilli, Kenneth C. Cundy, Joseph P. Dougherty, Choung U. Kim, Reza Oliyai and Valentino J. Stella, issued on Oct. 14, 2008.
U.S. Pat. No. 6,043,230 Prosecution File History (U.S. Appl. No. 09/314,606, filed May 19, 1999).

(56) References Cited

OTHER PUBLICATIONS

U.S. Pat. No. 6,043,230 Reexamination File History (Reexamination Request No. 90/008,549, filed Apr. 30, 2007).
U.S. Pat. No. 5,935,946C1 (Ex Parte Reexamination Certificate) to John D. Munger, Jr., John C. Rohloff and Lisa M. Schultze, issued on Oct. 14, 2008.
U.S. Pat. No. 5,935,946 Prosecution File History (U.S. Appl. No. 08/900,752), filed Jul. 25, 1997.
U.S. Pat. No. 5,935,946 Reexamination File History (Reexamination Request No. 90/008,556, filed Apr. 30, 2007).

* cited by examiner

UNITARY PHARMACEUTICAL DOSAGE FORM

BACKGROUND OF THE INVENTION

This application relates to products for the treatment of viral infections, in particular HIV infections, using the known antiviral compounds efavirenz (tradename Sustiva, also known as EFV), emtricitabine (tradename Emtriva, also known as FTC) and tenofovir DF (disoproxil fumarate, also known as TDF) (tradename Viread, sold in combination with emtricitabine under the tradename Truvada).

The Truvada product is produced by wet granulation of emtricitabine and tenofovir DF (WO 04/64845), which under the circumstances produces a chemically stable dosage form. This product does not contain efavirenz.

HIV therapy using efavirenz as well as emtricitabine and tenofovir DF has been considered desirable (hereafter "triple combination"; see WO 04/64845). Manufacturing a commercially viable triple combination product, however, would require that the final product meet stringent FDA requirements for bioequivalence to the commercial products, Viread (tenofovir disoproxil fumarate), Emtriva (emtricitabine), and Sustiva (efavirenz), and that the tablet be of suitable size for patients to easily swallow.

Initial efforts to simply combine the three drugs (active pharmaceutical intermediates, or APIs) into a unitary, essentially homogeneous composition manufactured by wet granulation failed to produce a chemically stable tablet. The tenofovir DF in this combination tablet was highly unstable and rapidly degraded in stability studies. The efavirenz formulation was unexpectedly incompatible with tenofovir DF, a result now attributed to the surfactant (sodium lauryl sulfate) found in the efavirenz portion of the formulation.

Another attempt was made to produce the triple combination, this time using a dry granulation of the three part combination and omitting the surfactant. This resulted in a tablet that failed to achieve bioequivalence with respect to efavirenz in human clinical trials. The peak efavirenz concentration in the blood stream and total drug exposure (Cmax and AUC) were both below the parameters determined for the commercial comparator, Sustiva (efavirenz) tablets. The inventors concluded that at least the surfactant in the triple combination (efavirenz/emtricitabine/tenofovir disoproxil fumarate) tablets was necessary to achieve bioequivalence to Sustiva.

Next, combination tablets were manufactured by wet granulating the efavirenz component with the surfactant and other excipients, separately manufacturing the Truvada component using dry granulation, mixing the granulates together, compressing the mixture into tablets, and then film-coating the tablets. Unexpectedly, this approach also failed to produce the desired bioequivalence in between the commercial product, Sustiva (efavirenz), and clinical trial material (i.e., proposed commercial triple combination product). A novel and inventive step was needed to overcome the shortcomings of more straight-forward approaches to a triple combination dosage form.

Copending U.S. Ser. No. 60/771,353 (filed of even date and expressly incorporated herein by reference) is directed to solving another obstacle encountered in the preparation of the triple combination dosage form, that of reducing the size of the combined product. While the prior art reports the successful manufacture of chemically stable Truvada preparations (WO04/64845), these preparations contain relatively low proportions of excipient to API. Increasing the proportion of excipients and wet granulating the three API combination unexpectedly resulted in a preparation in which the tenofovir DF was highly unstable. As reported in U.S. Ser. No. 60/771,353, it was believed that use of sufficient water to accomplish the wet granulation of efavirenz (which has relatively low solubility in comparison to emtricitabine and tenofovir DF) caused the latter two APIs to dissolve into a eutectic mixture. The eutectic mixture dried during granulation to form a glassy or amorphous product in which the tenofovir DF is chemically unstable in comparison to the crystalline API. Supplying enough excipient to ameliorate the effect of the excess water was not consistent with the objective of obtaining a triple combination oral dosage form of manageable proportions.

As described further in U.S. Ser. No. 60/771,353, this obstacle was overcome by dry granulating the emtricitabine and tenofovir DF composition, i.e., granulating the composition without contacting same with a destabilizing amount of liquid water. Omitting water (particularly, liquid water) or reducing the presence of water to an insubstantial amount eliminates the disadvantageous formation of a eutectic mixture and enhances the stability of the resulting pharmaceutical product.

Despite the advantages conferred by dry granulation of the emtricitabine/tenofovir DF component, it was still necessary to overcome the unexpected incompatibility of tenofovir DF and the surfactant used in the Sustiva formulation.

SUMMARY OF THE INVENTION

In accordance with this invention, the stability and bioequivalence objectives for the triple combination product have been achieved by providing a multicomponent dosage form, one component comprising tenofovir DF and, optionally, emtricitabine, and the other comprising at least efavirenz. Another embodiment of the invention is a dosage form comprising a tenofovir DF component and a surfactant component not in destabilizing contact with the tenofovir DF component.

DETAILED DESCRIPTION OF THE INVENTION

The dosage form of this invention comprises efavirenz, emtricitabine and tenofovir DF. As noted, tenofovir DF and efavirenz are in separate components. Emtricitabine generally is included in the tenofovir DF component, but in other embodiments the emtricitabine is present in its own component, or is mixed with the efavirenz component. Its disposition is not critical to the practice of this invention. All that is necessary is that emtricitabine be present in the dosage form and that the tenofovir DF component be substantially separated from the surfactant in the efavirenz component. Any method, additive, process feature or configuration that suitably minimizes the contact of surfactant with tenofovir DF is suitable in the practice of this invention.

The term "component" means a physically discrete unit or compartment which is associated physically with and in contact with other components. This does not mean that the units or compartments are physically not in contact. In fact, it generally is preferred that they are in physical contact and form a unitary device, article or composition. The degree of association is only that which is needed to facilitate the oral consumption of the composition as a single dosage form. This invention does not include, for example, patient packs with the Sustiva and Truvada products in separate wells or containers, or other associations which are essentially packaging solutions alone (although, of course, the compositions of this invention optionally are packed or packaged in any conventional fashion suitable under the circumstances).

Typically, the components of the dosage form of this invention conveniently are organized in multiple layers, ordinarily a bilayer as shown in the exemplified embodiment. However, if emtricitabine is present in its own component then the dosage form will constitute at least a trilayer structure. There need not be a single component for each drug (for example, the dosage forms optionally include 2 layers for each of the components, for a total of 6). Thus, the dosage unit includes laminates of many components. There do not need to be equal numbers of each component, e.g., layers, for each drug or drug combination so long as the total dosage of all components in sum is the desired amount.

Other means for spatially organizing the components are suitable so long as the desired degree of separation of tenofovir DF and surfactant is accomplished. For example, rather than forming planar layers along the axis of a tablet, the components optionally are organized in an annular fashion, with each ring or cylinder containing a separate component. Another alternative is to employ a press coating process to associate the components.

The components generally are in direct contact with one another, i.e., no barrier or protective layer is present between them. In other embodiments, a barrier is introduced between the incompatible components. A suitable example of this embodiment of the invention would be a multi-compartment capsule in which the incompatible components are distributed into separate compartments. Alternatively, a tablet is optionally provided that contains one encapsulated component disbursed or distributed within the incompatible component. In general, intimate, direct admixture of the incompatible components is undesirable unless means are provided to protect the tenofovir DF component from surfactant.

In typical embodiments the components of the dosage form of this invention are spatially organized so as to not place the tenofovir DF component into destabilizing contact with the surfactant in the efavirenz component. "Destabilizing" means any contact between tenofovir DF and the surfactant that is capable causing pharmaceutically unacceptable degradation of tenofovir DF. A stabilizing configuration is any spatial organization of the tenofovir DF and efavirenz components that does not result in the generation of a "pharmaceutically unacceptable amount" of any one of the following degradation products. A destabilizing contact is a spatial organization that results in the generation of any of the following degradation products in a "pharmaceutically unacceptable amount".

The spatial geometry and conditions of the permitted contact between tenofovir DF and surfactant-containing component are essentially unlimited. This spatial geometry is termed a "stabilizing configuration" or, stated differently, is a configuration that does not contain a "destabilizing contact" as defined below. There are many ways in which the central observation of this invention (that is, that sodium lauryl sulfate destabilizes tenofovir DF) can be harnessed to prevent the generation of pharmaceutically unacceptable levels of degradation of tenofovir DF.

In addition, when emtricitabine is present in the tenofovir DF component, the permitted contact also that which does not produce pharmaceutically unacceptable amounts of emtricitabine degradation product.

"Degradation" of tenofovir DF is the generation—in pharmaceutically unacceptable amounts—of at least one of the degradation products mono-POC PMPA, dimer or mixed dimer. "Degradation" of FTC is defined as the generation—in pharmaceutically unacceptable amounts, of FTU. These degradation products are shown below.

Mono-POC PMPA

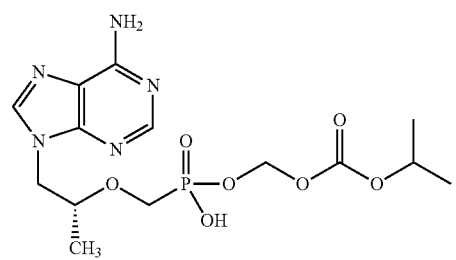

mono-POC PMPA

Dimeric Degradation Products

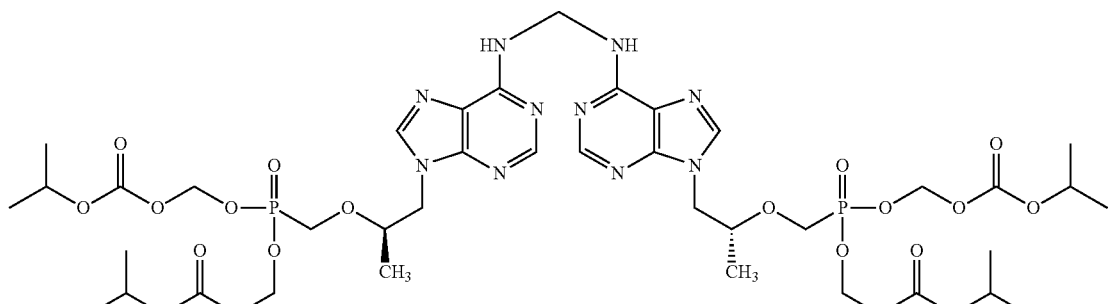

Dimer

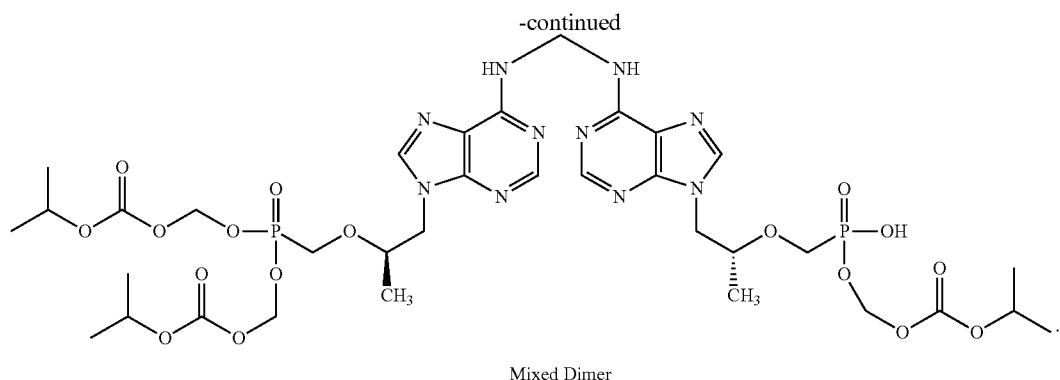

Mixed Dimer

FTU has the Structure

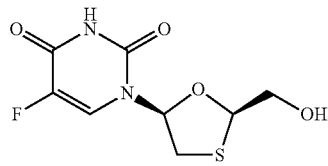 [SMILES: O=c1[nH]c(=O)n([C@@H]2CS[C@H](CO)O2)cc1F]

A "pharmaceutically unacceptable amount" is defined as the following amounts of each degradation product. Degradation products optionally are assayed in either an absolute or incremental amount. The absolute or total amount of degradation product is simply the amount found in the test article. The incremental amount is the additional amount of degradation product appearing in the product over that which was present (if any) in the API starting material. Moreover, the amount of degradation product optionally is measured at two points in time. One is at the time of release into the marketplace. The other is after exposure to storage conditions under the conditions described below, i.e., the shelf life as set forth below.

Total Amounts at Release (First Commercial Sale)

No more than about 3%, ordinarily about 1.5%, of mono-POC PMPA,

No more than about 1%, ordinarily about 0.5% of Dimer,

No more than about 0.5%, ordinarily about 0.25% of Mixed Dimer.

Less than about 0.5%, ordinarily about 0.2% of FTU

Total Amounts at Shelf Life (Storage at 25° C./60% RH for 24 Mo.)

No more than about 10%, ordinarily about 5% of mono-POC PMPA,

No more than about 2%, ordinarily about 1% of Dimer,

No more than about 2%, ordinarily about 1% of Mixed Dimer.

No more than about 4%, ordinarily about 2% of FTU

Incremental Amounts at Release (First Commercial Sale)

No more than about 2%, ordinarily about 0.5%, of mono-POC PMPA,

No more than about 0.6%, ordinarily about 0.1% of Dimer,

No more than about 0.3%, ordinarily about 0.05% of Mixed Dimer.

Less than about 0.4%, ordinarily about 0.1% of FTU

Incremental Amounts at Shelf Life (Storage at 25° C./60% RH for 24 Mo.)

No more than about 9%, ordinarily about 4% of mono-POC PMPA,

No more than about 1.6%, ordinarily about 0.6% of Dimer,

No more than about 1.8%, ordinarily about 0.8% of Mixed Dimer.

No more than about 3.9%, ordinarily about 1.9% of FTU.

The percentage of degradation products is the amount of degradation product as measured by HPLC retention time comparison. In the HPLC retention time comparison, the retention time of the main peaks observed in the tablets is required to be within 2% of the retention time of the main peaks in the a reference standard preparation containing efavirenz, emtricitabine, and tenofovir DF in an assay which has been shown to be specific for efavirenz, emtricitabine, and tenofovir DF. The percentage is determined by dividing the total amount of tenofovir DF plus the three degradation products into the amount of individual degradation product as determined by the HPLC assay.

These parameters are employed to evaluate whether a test composition has met the requirements of a stabilizing contact. For example, a triple combination dosage form optionally is designed as a shaped article comprising slugs of compressed granules of the tenofovir DF component dispersed within a matrix of the efavirenz component. A variety of slug sizes might be used in making the composition. This constellation of potential products then would be tested, or stored under the conditions above and then tested, to assay the generation of tenofovir DF and/or FTC degradation products. If the resulting product upon release did not contain more than the specified approximate limits of any one or more of the 4 contaminants listed under any of the 4 assay paradigms above, then the contact would be considered stabilizing. Of course, the artisan may adopt more stringent standards, but this will be a matter of choice and shall not limit the scope of this invention.

In preferred embodiments the emtricitabine and tenofovir DF are combined and this component is prepared by dry granulation (U.S. Ser. No. 60/771,353). In preferred embodiments, a composition comprising dry granulated tenofovir DF and emtricitabine is employed in one component of the dosage forms of this invention.

Dry granulation is a well-known pharmaceutical manufacturing process per se. In general, API is combined with excipients and lubricant excipient and then compressed to form a mass. This mass typically is then comminuted or milled, then sieved to obtain the desired size of particle. The granular product is compressed into tablets, filled into capsules or otherwise formed into a unitary dosage form in conventional fashion.

Compression into a mass is accomplished by conventional equipment. Typically, the API and excipients are passed through a roller apparatus for compaction. However, other means for compacting the API mixture, e.g., compaction into slugs (or "slugging"), optionally are used.

A dry granulation process is one in which a dry composition of the API and selected excipient(s) is compressed to form a mass, which is comminuted or milled if necessary, and then optionally sieved to produce the desired size granules. Compression into a mass is accomplished by conventional equipment. Typically, the API and excipients are passed through a roller apparatus for compaction. However, other means for compacting the API mixture, e.g., compaction into slugs (or "slugging"), can be used.

A composition comprising dry granulated emtricitabine and tenofovir DF is the product of a dry granulation process. This composition essentially retains the crystalline APIs and is substantially free of dried eutectic emtricitabine/tenofovir DF. It typically will contain less than about 15% by weight dried eutectic mixture, ordinarily less than about 10% and generally less than about 5%.

The dry granulation process is conducted in the absence of a destabilizing amount of water, "destabilizing" being that amount of liquid water that is capable causing pharmaceutically unacceptable degradation of tenofovir DF and/or FTC as defined herein. If the dosage form of this invention includes a dry granulated emtricitabine/tenofovir DF component, then the amount of permitted degradation product in the final dosage form is still the same as that which is set forth above, i.e., the amount of water exposure and contact, together or alone, are not to result in degradation products failing to meet the standards described above. It is an option, of course, to test the dry granulates for their level of degradation product first, and if they pass, then to formulate them into the dosage form of this invention and then determine if the contact results in any increase in degradation products that takes the resulting dosage form outside the parameters established.

Bound, entrained or absorbed water are commonly present in excipients. This water will not significantly adversely affect the stability of tenofovir DF and thus is not excluded from the dry granulates optionally used in the dosage form of this invention. In general, liquid water (added or generated in situ) from any source, e.g., chemical reactions, condensation, entrained ice, or the like is to be excluded from the granulation. However, minor amounts of liquid water optionally are added during granulation. These amounts typically would be less than about 5% by weight, ordinarily less than about 1% by weight, however the water is generated or supplied. Water is present in the final granulation product up to about 10% by weight (Karl Fischer), but preferably is less, as low as 0.1% by weight. However, permitted quantities of water may vary depending upon other factors in the granulation, e.g., excipient type, temperature and so forth. For example, if a hygroscopic excipient is included this will convert added water into a bound form. All that is necessary is that the water not result in degradation of tenofovir DF and/or emtricitabine in the final product. In general, water is excluded both from the pregranulation stage (preparation of the composition to be used directly in the granulation) as well as during the granulation process itself.

Absence of water or "dry" does not mean the absence of liquid. Granulations with organic solvents are also feasible provided that destabilizing amounts of water are excluded.

Dry granulation results in a product that contains minimal amounts of water. The amount of water in the product granulate or dosage forms made therefrom are measured by loss on drying (LOD) or by the Karl Fischer method. The LOD of compositions of this invention are about 15%, about 10%, about 5% or typically less than about 3% by weight. The Karl Fischer water is about from 0.1 to 10% by weight, usually less than about 5% by weight, or less than about 2%. The amount of water in the final preparations, as opposed to the granulates, is a function of granulate water as well as minor amounts of water used during subsequent process steps such as coating. These amounts of water added in later steps than granulation generally will not affect the stability of the emtricitabine/tenofovir DF APIs, and therefore are subject to considerable permitted variation.

The manufacturing process described below is directed to the preparation of a triple combination tablet containing efavirenz, emtricitabine and tenofovir DF. In this particular embodiment the last two drugs are emplaced in a portion of the tablet which is separate from, but in contact with, the portion of the tablet containing efavirenz. It will be understood, however, that the emtricitabine and tenofovir DF component of the tablet, which is an embodiment of this invention, optionally is manufactured as a stand-alone product and not necessarily in assembly with an efavirenz component. In this option, the emtricitabine/tenofovir DF dry granulation intermediate described below is simply compressed into tablets or conventionally processed into other conventional unitary dosage forms such as capsules, cachets, suppositories, or the like.

The dosage forms of this invention are stored in containers, preferably under desiccant such as silica gel in amounts generally sufficient to maintain the RH over the dosage forms at under about 10%, preferably under about 5%.

Materials

The quantitative compositions of the efavirenz powder blend, FTC/TDF powder blend, and film-coated bi-layer EFV/FTC/TDF tablets are listed in Table 1, Table 2, and Table 3, respectively. The quantities of efavirenz, emtricitabine, and tenofovir DF were adjusted for drug content factors (DCF) if the value was less than 0.99 with a concomitant reduction to the quantity of microcrystalline cellulose in each granulation.

TABLE 1

Quantitative composition of efavirenz powder blend

| Ingredient | % w/w of Total | Unit Formula (mg/tablet) |
|---|---|---|
| Efavirenz | 38.71 | 600.0 |
| Microcrystalline Cellulose, NF/EP | 11.52 | 178.6 |
| Hydroxypropyl cellulose, NF/EP | 2.48 | 38.4 |
| Sodium Lauryl Sulfate, USP/EP | 0.77 | 12.0 |
| Croscarmellose Sodium, NF/EP | 3.87 | 48.0 |
| Magnesium Stearate, NF/EP | 0.58 | 9.6 |
| Total for Tablet Core | 57.94 | 898.0 |

TABLE 2

Quantitative composition of FTC/TDF powder blend

| Ingredient | % w/w of Total | Unit Formula (mg/tablet) |
|---|---|---|
| Emtricitabine | 12.90 | 200.0 |
| Tenofovir Disoproxil Fumarate | 19.35 | 300.0 |
| Microcrystalline Cellulose, NF/EP | 5.77 | 89.5 |

TABLE 2-continued

Quantitative composition of FTC/TDF powder blend

| Ingredient | % w/w of Total | Unit Formula (mg/tablet) |
|---|---|---|
| Croscarmellose Sodium, NF/EP[a] | 3.10 | 48.0 |
| Magnesium Stearate, NF/EP[a] | 0.94 | 14.5 |
| Total for Tablet Core | 42.06 | 652.0 |

[a]To be incorporated into both the intragranular and extragranular portions of the formulation during the manufacturing process.

TABLE 3

Quantitative composition of film-coated bi-layer EFV/FTC/TDF Tablets

| Ingredient | % w/w of Total | Unit Formula (mg/tablet) |
|---|---|---|
| Efavirenz Powder Blend | 57.94 | 898.0 |
| FTC/TDF Powder Blend | 42.06 | 652.0 |
| Total for Tablet Cores | 100.00 | 1550.0 |
| Opadry II Pink | 3.00 | 46.5 |
| Purified Water, USP/EP[a] | | |
| Total for Film-Coated Tablets | | 1596.5 |

[a]Water removed during film-coating process.

The excipients were all compendial grade materials:
Efavirenz Wet Granulation

Efavirenz was wet granulated using a Niro-Fielder PMA-400 equipment train. Efavirenz, microcrystalline cellulose and sodium lauryl sulfate (Table 1) were added to the PMA-400 and blended for 3 minutes. Croscarmellose sodium and hydroxyl propyl cellulose (Table 1) were added to the pre-mix and blended for an additional 2 minutes. Purified water was added to form a suitable granulation followed by additional wet massing after water addition. Table 4 lists the summary of granulation parameters used for two representative lots and sub parts. All sub parts used a water to efavirenz ratio of 1.30 except for AB509 Mix C which used a 1.25 ratio of water to efavirenz.

TABLE 4

Efavirenz wet granulation process parameter summary

| Process | Parameter | AB507 | | | AB509 | | |
|---|---|---|---|---|---|---|---|
| | | Mix A | Mix B | Mix C | Mix A | Mix B | Mix C |
| Granulation | Total Water Added (kg) | 33.57 | 33.56 | 33.56 | 33.56 | 33.56 | 32.18 |
| | Ratio of Water: EFV | 1.30 | 1.30 | 1.30 | 1.30 | 1.30 | 1.25 |
| | Total Addition Time (Min:Sec) | 9:36 | 9:29 | 9:24 | 9:17 | 9:32 | 9:02 |
| | Final Impeller Power (% Load) | 10.4 | 9.8 | 8.5 | 11.3 | 11.3 | 9.9 |
| Wet Massing | Total Time (Min:Sec) | 4:00 | 3:00 | 3:00 | 2:00 | 1:15 | 2:00 |
| | Final Impeller Power (% Load) | 11.6 | 12.0 | 11.7 | 18.0 | 17.7 | 10.5 |
| Drying* | Inlet Temperature (° C.) | | 70 | | | 70 | |
| | Time (Hr:Min) | | 1:45 | | | 1:51 | |
| | Final Outlet Temp. (° C.) | | 50 | | | 50 | |
| | Final LOD (%) | | 0.3 | | | 0.8 | |

*Mixes A, B, and C for each lot were combined before drying

In general, the wet granules were milled, then dried to an LOD less than or equal to 1.5%. The dried granules were milled and blended with magnesium stearate (Table 1).

The bulk density, particle size, and moisture content by LOD of the efavirenz granulations are listed in the first three lines of Table 5 (the B lot numbers are efavirenz products, the C lot numbers are emtricitabine/tenofovir DF). Particle size was determined by sifting 10-gram samples through 3-inch diameter screens using a sonic sifter (Model L3P, ATM Corporation, Milwaukee, Wis., USA). The following US Standard Mesh sizes (openings) were used: #20 (850 μm), #30 (600 μm), #40 (425 μm), #60 (250 μm), #80 (180 μm), and #250 (63 μm). The agitation and pulse were set at 7 and the sifting time was 5 minutes. The amount of powder retained on the sieves and the fines collector was determined by calculating the difference in weight before and after sifting. The geometric mean particle size was calculated by logarithmic weighting of the sieved distribution.

Bulk density was determined by filling a 100-mL graduated cylinder with sample and calculating the difference in weight between the empty and full graduated cylinder per unit volume.

Moisture content measurements by loss on drying (LOD) were performed by heating a 2.5 g sample at 85° C. for 15 minutes using a heat lamp/balance system (Model LP16/PM400, Mettler-Toledo, Columbus, Ohio, USA).

The granulations had similar bulk densities (0.54 to 0.56 g/mL) and similar geometric mean particle size distributions (215 to 268 μm). The LOD values of the final blend were consistent from 0.98 to 1.80%. The individual sieve distributions for the efavirenz granulations are listed in Table 6.

TABLE 5

Summary of efavirenz powder blend and emtricitabine/tenofovir DF powder blend physical properties

| Gilead Lot Number | Geometric Mean Diameter Particle Size (μm) | Bulk Density (g/mL) | LOD (%) |
|---|---|---|---|
| AB507 | 247 | 0.56 | 1.80 |
| AB508 | 215 | 0.55 | 1.08 |

TABLE 5-continued

Summary of efavirenz powder blend and emtricitabine/tenofovir DF powder blend physical properties

| Gilead Lot Number | Geometric Mean Diameter Particle Size (μm) | Bulk Density (g/mL) | LOD (%) |
|---|---|---|---|
| AB509 | 268 | 0.54 | 0.98 |
| AC507 | 330 | 0.60 | 0.91 |
| AC508 | 344 | 0.60 | 1.02 |
| AC509 | 343 | 0.59 | 0.99 |

TABLE 6

Particle size distribution for efavirenz and FTC/TDF powder blends

| Gilead Lot Number | % Weight Retained on Screen* U.S. Standard Screen Size (mesh opening) | | | | | | |
|---|---|---|---|---|---|---|---|
| | 20 (>850 μm) | 30 (600 μm) | 40 (425 μm) | 60 (250 μm) | 80 (180 μm) | 230 (63 μm) | pan (<63 μm) |
| AB507 | 5.9 | 10.9 | 16.2 | 22.2 | 11.4 | 22.6 | 10.9 |
| AB508 | 6.1 | 10.4 | 15.8 | 20.0 | 9.0 | 20.8 | 17.9 |
| AB509 | 9.6 | 13.3 | 17.4 | 20.1 | 8.9 | 17.2 | 13.3 |
| AC507 | 22.0 | 19.8 | 15.2 | 11.2 | 4.6 | 10.5 | 16.6 |
| AC508 | 22.1 | 20.1 | 15.4 | 11.6 | 5.1 | 10.6 | 14.9 |
| AC509 | 22.4 | 19.7 | 15.3 | 11.7 | 4.8 | 11.1 | 14.8 |

Emtricitabine/Tenofovir DF Dry Granulation

Emtricitabine, microcrystalline cellulose, tenofovir DF, and croscarmellose (Table 2) were blended in a 650 L tote bin using a Gallay blender for 10 minutes. Magnesium stearate (Table 2) was added and blended for an additional 5 minutes. This pre-blend was then transferred to a 320-L Matcon bin fitted with a cone valve discharging station to assist with material transfer into the roller compactor hopper.

The pre-blend was roller compacted using a Gerteis Macro-Pactor model 250/25/3 with 250 mm diameter by 50 mm wide smooth rolls. The roll gap thickness (2 mm), roll speed (10 rpm), compaction force (4 kN/cm), oscillating mill speed (75 rpm clockwise and counterclockwise), and oscillating mill screen opening (1.25 mm) were kept constant for all batches. The oscillating mill angle of rotation was also the same for all lots at 150° clockwise and 140° counterclockwise.

There was no material handling issues among all three batches while feeding into the roller compactor. The entire roller compaction process proceeded without any apparent sign of heat accumulation on the equipment, product build-up, or melting. The granulations then were blended with extragranular croscarmellose sodium (34% of total amount) and magnesium stearate (47% of total amount).

The particle size, bulk density, and LOD of the emtricitabine/tenofovir DF dry granulations were all similar for the three batches and are listed in Table 5 (bottom 3 compartments). The geometric particle sizes were very similar at from 330 to 344 μm. Bulk densities ranged from 0.59 to 0.60 g/mL. The final blend LOD values were consistent from 0.91 to 1.02%. The final powder blends have remarkably consistent physical properties.

The efavirenz and tenofovir DF granulations each have geometric mean particle sizes that optionally range about from 100 to 600 μm, bulk densities optionally ranging about from 0.1 to 1 g/mL and LOD values optionally ranging about from 0.1 to 10% by weight.

Final Blends

The mass of efavirenz granulation and extragranular magnesium stearate were adjusted appropriately based on the yield of emtricitabine/tenofovir DF dry granulation. Efavirenz granulation and emtricitabine/tenofovir DF dry granulation were blended in a 3 cubic foot V-blender for 10 minutes. Magnesium stearate was added and blended an additional 5 minutes. Samples of the final powder blend were taken from 10 different locations after blending and analyzed for blend uniformity. The efavirenz and emtricitabine/tenofovir DF final powder blends showed acceptable blend uniformity and homogeneity for all three active ingredients indicating the robustness of the formulation regardless of the particle size or bulk density of emtricitabine/tenofovir DF dry granulations and efavirenz granulations. The granulations and blending procedure would be satisfactory for the formulation on a larger scale.

Tablet Core Compression

Efavirenz/emtricitabine/tenofovir DF final powder blend was compressed into tablet cores using a Stokes Genesis Model 757, 41 station bilayer tablet press equipped plain-faced upper/embossed "123" lower, capsule-shaped (20.0 mm×10.4 mm) punches. The target mass of the tablet cores was 1550 mg. Samples of the core tablets were taken from a minimum of 20 equally spaced locations during the compression run and analyzed for content uniformity. In general, all powder blends compressed satisfactory on the rotary tablet press with respect to tablet hardness, friability, tablet thickness, tablet appearance, and tablet weight variation. The compression operation was performed at a rate of approximately 500 tablets/minute (12 rpm press speed) or approximately 0.8 kg/minute to deliver satisfactory tablet weight uniformity.

Tablet Film-Coating

Suitable film coatings are selected by routine screening of commercially available preparations. This activity is well within the skill of the ordinary artisan. Each lot of tablet cores was divided into two coating sub-lots that were film coated in a 48-inch Thomas Engineering COMPU-LAB coating pan using a dual-nozzle spraying system. All the tablet cores were film-coated using a 15% w/w aqueous coating suspension Opadry II Pink, which was used within 24 hours of preparation. All tablet cores were coated to a target weight gain of 3.0% using a target spray rate of 180 g/min, which corresponds to a normalized spray rate of 1.5 to 2.3 g/min/kg tablets.

HPLC Assay for Degradation Products

Efavirenz/emtricitabine/tenofovir DF tablets (EFV/FTC/TDF tablets) are assayed by HPLC for EFV, FTC, and TDF using external reference standards. The degradation products of EFV, FTC, and TDF are determined by area normalization with the application of relative response factors, as appropriate. The identity of EFV, FTC, and TDF are confirmed by comparison of their retention times with those of the reference standards.

Standard and Sample Solution Preparation
Standard and Sample Solvent
25 mM Phosphate Buffer, pH 3

Weigh and transfer 3.4 g of potassium phosphate monobasic, anhydrous into a 1 L volumetric flask. Add about 800 mL of water and mix until dissolved. Adjust the pH to 3.0±0.1 with phosphoric acid, then dilute to volume with water.

Sample Solvent (40:30:30 25 mM Phosphate Buffer, pH 3:Acetonitrile:Methanol)

Combine 400 mL of 25 mM Phosphate Buffer, pH 3, 300 mL of acetonitrile, and 300 mL of methanol and mix. Allow to equilibrate to ambient temperature.

50:50 Acetonitrile:Methanol

Combine 500 mL of acetonitrile and 500 mL of methanol and mix. Allow to equilibrate to ambient temperature.

Standard Solution

Accurately weigh approximately 60 mg of EFV reference standard, 20 mg of FTC reference standard, and 30 mg of TDF reference standard and transfer into a 100 mL volumetric flask. Add approximately 80 mL of sample solvent (40:30:30) to the flask and mix or sonicate until dissolved. Dilute to volume with sample solvent (40:30:30) and mix well. The final concentration of each component is approximately 0.6 mg/mL of EFV, 0.2 mg/mL of FTC, and 0.3 mg/mL of TDF.

System Suitability Test Solutions
Sensitivity Check Standard

Prepare a 10 μg/mL FTU stock solution by accurately weighing out approximately 10 mg of the FTU authentic substance into a 100 mL volumetric flask. Add sample solvent (40:30:30) to approximately 80% of volume and mix or sonicate until dissolved. Dilute to volume with sample solvent (40:30:30) and mix well. Pipet 10 mL of this solution into a 100 mL volumetric flask. Dilute to volume with sample solvent (40:30:30) and mix well.

Prepare the sensitivity check standard containing 0.2 mg/mL of FTC and 0.2 μg/mL of FTU (0.10% relative to FTC). Accurately weigh out 20 mg FTC into a 100 mL volumetric flask. Using a Class A pipet, transfer 2.0 mL of the FTU stock solution into the same flask. Add additional sample solvent (40:30:30) to the flask and mix or sonicate until dissolved. Dilute to volume with sample solvent (40:30:30) and mix well. Alternately, 2.0 mL of the 10 μg/mL FTU stock solution may be added to the standard solution prior to diluting to volume.

Sample Preparation for EFV/FTC/TDF Tablets

The strength and degradation product content of EFV/FTC/TDF tablets is determined by the analysis of a composite solution prepared from ten tablets. The final concentration of each component in the sample solution is approximately 0.6 mg/mL of EFV, 0.2 mg/mL of FTC, and 0.3 mg/mL of TDF.

a) Place ten tablets into a 1 L volumetric flask and add 400 mL 25 mM phosphate buffer, pH 3 to the volumetric flask.
b) Mix by stirring vigorously for about 75 minutes.
c) Add 50:50 acetonitrile:methanol to the flask to approximately 2 cm below the volume mark.
d) Equilibrate the solution to ambient temperature by mixing for an hour. Dilute to volume with 50:50 acetonitrile:methanol. Mix well by inverting the flask or stirring with a magnetic stir bar.
e) Using a 0.45 μm syringe filter with a syringe, filter approximately 10 mL of step (d) for the next dilution. Discard the first 2 mL of filtrate.
f) Using a Class A pipet, transfer 5.0 mL of the filtrate from step (e) into a 50 mL volumetric flask and dilute to volume with sample solvent (40:30:30). Mix well.

Chromatography

1. An HPLC equipped with a UV detector and an electronic data acquisition system is used.
2. An HPLC column, 4.6 mm i.d. by 250 mm long, packed with C12 reversed phase, 4 μm particle size, 80 Å pore size material is used.
3. Mobile phase buffer: Prepare a 20 mM ammonium acetate buffer, pH 4.6; adjust pH with acetic acid as needed.
4. Mobile phase gradient: Elute with Mobile Phase Buffer:acetonitrile from 99:1 to 1:99 over 67 minutes.
5. Peak detection: UV at 262 nm
6. Injection volume: 10 μL.

Under the stated chromatographic conditions, the retention times of the FTC, TDF and EFV peaks are typically 11, 33, and 50 minutes, respectively.

Injection Sequence

Inject the sample solvent at least twice as a blank to ensure that the column is equilibrated and to identify any potential artifact peaks.

Inject the sensitivity check standard or standard solution containing approximately 0.10% FTU to measure the sensitivity of detection.

Inject five replicates of standard solution 1 (R1), followed by a single injection of standard solution 2 (R2). Calculate the theoretical plates and tailing factors from the standard solution injections.

For identity, strength, and degradation product determination, perform duplicate injections of the sample solution.

All sample solutions must be bracketed by standard solution injections. Generally, not more than ten sample solution injections between bracketing standard injections is recommended.

System Suitability
Theoretical Plates and Tailing Factor

Calculate the number of theoretical plates (N) and the tailing factors (T) for the EFV, FTC, and TDF peaks from the Standard Solution chromatogram. The formulas for N and T determination are defined in the current United States Pharmacopeia. The values of these parameters must conform to the criteria: $N \leq 40{,}000$ and $0.8 \leq T \geq 2.0$.

Sensitivity Check

The sensitivity check will utilize the FTU peak in the sensitivity check standard present at approximately 0.10%. Calculate the area percent of the FTU peak with the appropriate RRF (listed in Table 2) applied for the sensitivity check standard using the calculation for percent individual degradation product. Compare this result to the theoretical percent of FTU for the sensitivity check standard as follows:

$$\text{Sensitivity} = \frac{FTU_{Determined}}{FTU_{Theoretical}}$$

Where:
FTU$_{Determined}$=area percent of FTU determined for the sensitivity check standard or standard solution
FTU$_{Theoretical}$=theoretical area percent of FTU for the sensitivity check standard or standard solution
The sensitivity must be between 0.70-1.30.
Evaluation and Calculations
Identification of Degradation Products Employ the appropriate detection parameters (such as peak threshold, minimum peak area, etc.) to allow detection of peaks present at 0.05% or less. Identify the impurities and degradation products of EFV, FTC, and TDF present in the chromatograms of the sample solution injections by noting the relative retention times (RRT) of the observed secondary peaks, discounting any peaks not related to the sample. Only degradation products are quantified. Calculate the average of the results from all sample solution injections to the nearest 0.01%. In cases where the degradation product was not detected or was below the threshold of integration in one injection and/or sample, use only the quantified results in the calculation (i.e., do not treat as a zero value).

$$RRT = \frac{\text{retention time of the secondary peak}}{\text{retention time of the tenofovir disoproxil peak}}$$

The RRTs and the relative response factor (RRF) values of the potential impurities and degradation products for EFV are shown in Table 1, and the degradation products are shown in bold-face. The impurities and degradation products for FTC are shown in Table 2, and the degradation products are in bold-face. The impurities and degradation products for TDF are shown in Table 3, and the degradation products are in bold face.

As the RRT may vary, the identity of impurities and degradation products may be confirmed by comparison to authentic substances (or to impurity and degradation product peaks in the reference standard), if required.

Degradation Product Content Determination
Quantification of FTC Degradation Products Determine the level of each degradation product of FTC observed in the chromatograms of the sample solution injections using the following formula:

$$\text{Degradation Product (\%)} = \frac{1}{TPA} \times RRF \times 100$$

Where:
I=Area of the degradation product peak
TPA=Total peak area (area of FTC and all related degradation products, excluding impurities and artifacts), corrected by RRF
RRF=Relative response factor with respect to FTC
8.4.3 Quantification of TDF Degradation Products Determine the level of each degradation product of TDF observed in the chromatograms of the sample solution injections using the following formula:

$$\text{Degradation Product (\%)} = \frac{1}{TPA} \times RRF \times 100$$

Where:
I=Area of the degradation product peak or unassigned peak
TPA=Total peak area (area of the TDF main peak, all related degradation products, and all unassigned peaks, excluding impurities and artifacts), corrected by RRF
RRF=Relative response factor with respect to TDF
Results and Reporting
Degradation Product Content Report individually the average of the results for each degradation product observed to the nearest 0.01%. Report the total degradation product content of EFV, FTC, and TDF respectively to the nearest 0.1%, as the sum of the average levels of all degradation product peaks observed. For degradation products found at levels less than 0.05%, report their levels as trace and do not include their levels in the calculation of total degradation product content.

REFERENCES

United States Pharmacopeia <621>
Pharmacopeial Forum 26(4) 2000

TABLE 1

EFV related impurities and degradation products

| EFV Related Compound | Approximate RRT[a] | RRF[b] |
|---|---|---|
| SD-573[c] | 1.46 | 0.5 |
| SR-695[d] | 1.50 | |
| EFV | 1.50 | |
| SP-234 | 1.57 | |
| SW-965 | 1.60 | |
| SE-563 | 1.73 | |
| SM-097[c] | 1.83 | 0.5 |

[a]Approximate RRTs, and the values are relative to the TDF peak
[b]RRFs for EFV related degradation products are relative to EFV
[c]EFV related degradation products
[d]SR-695 elutes before EFV (approximately 0.1 min separation)
Degradation products are marked in bold face

TABLE 2

FTC related degradation product

| FTC Related Compound | Approximate RRT[a] | RRF[b] |
|---|---|---|
| FTC | 0.33 | |
| FTU[c] | 0.38 | 0.7 |

[a]Approximate RRTs, and the values are relative to the TDF peak
[b]RRFs for FTC related degradation products are relative to FTC
[c]FTC related degradation products

TABLE 3

Tenofovir DF related degradation products

| TDF Related Compound | Approximate RRT[a] | RRF[b] |
|---|---|---|
| mono-POC PMPA[c] | 0.47 | 0.6 |
| Mixed Dimer[c] | 0.98 | 1.0 |
| TDF | 1.00 | |
| Dimer[c] | 1.34 | 0.9 |

[a]Approximate RRTs, and the values are relative to the TDF peak
[b]RRFs for TDF related degradation products are relative to TDF
[c]TDF related degradation products

What is claimed:

1. A unitary dosage form comprising tenofovir DF in a first compartment and a surfactant and efavirenz in a second compartment, wherein the first and second compartments are not in a direct admixture, and further comprising emtricitabine.

2. The unitary dosage form of claim 1 wherein there is no barrier layer between the first component and the second component.

3. The unitary dosage form of claim 1 wherein there is a barrier layer between the first component and the second component.

4. The unitary dosage form of claim 1 wherein the compartments are layers.

5. The unitary dosage form of claim 1 which is suitable for oral administration.

6. The unitary dosage form of claim 4 which is a bilayer tablet weighing less than about 2.5 grams.

7. The unitary dosage form of claim 1 wherein the second compartment is produced by high shear wet granulation.

8. The unitary dosage form of claim 1 wherein the surfactant is sodium lauryl sulfate.

9. The unitary dosage form of claim 1 wherein the first compartment is produced by dry granulation.

10. The unitary dosage form of claim 1 wherein the total amount of efavirenz, emtricitabine and tenofovir DF is greater than about 60% by weight of the unitary dosage form.

11. The unitary dosage form of claim 1 which further comprises magnesium stearate, croscarmellose sodium, microcrystalline cellulose and hydroxypropyl cellulose.

12. The unitary dosage form of claim 11 wherein the approximate percentages by weight of efavirenz, tenofovir DF, emtricitabine, magnesium stearate, croscarmellose sodium, microcrystalline cellulose, sodium lauryl sulfate, and hydroxypropyl cellulose are, respectively, about 39, about 19, about 13, about 2, about 7, about 17, about 1 and about 2.

13. The unitary dosage form of claim 5 wherein efavirenz, emtricitabine and tenofovir DF are provided to a patient upon oral administration at substantially the same AUC and $C_{max}$ as the FDA approved products Truvada and Sustiva.

14. The unitary dosage form of claim 1 which weighs about from 1200 mg to 2300 mg (including any film coating that is optionally present).

15. The unitary dosage form of claim 4 wherein the layers are oriented horizontally along an axis of the tablet.

16. A container comprising the unitary dosage form of claim 1 and a desiccant.

17. The unitary dosage form of claim 1 wherein the total amount of efavirenz, emtricitabine and tenofovir DF is about 70% by weight of the composition.

18. A method comprising administering to a patient in need of antiviral therapy the dosage form of claim 1, wherein the antiviral therapy is anti-HIV therapy.

19. The method of claim 18 wherein the dosage form is administered only once daily.

* * * * *

UNITED STATES PATENT AND TRADEMARK OFFICE
CERTIFICATE OF CORRECTION

PATENT NO.        : 9,545,414 B2  
APPLICATION NO.   : 14/640825  
DATED             : January 17, 2017  
INVENTOR(S)       : Dahl et al.

Page 1 of 1

It is certified that error appears in the above-identified patent and that said Letters Patent is hereby corrected as shown below:

In the Claims

At Claim 5, Column 17, Line 15, please replace "form of claim 1" with --form of claim 4--.

Signed and Sealed this
Eighteenth Day of April, 2017

Michelle K. Lee
*Director of the United States Patent and Trademark Office*